(12) United States Patent
Clark et al.

(10) Patent No.: US 10,905,490 B2
(45) Date of Patent: Feb. 2, 2021

(54) CRYOTHERAPEUTIC DEVICES FOR RENAL NEUROMODULATION AND ASSOCIATED SYSTEMS AND METHODS

(71) Applicant: Medtronic Ardian Luxembourg S.a.r.l., Luxembourg (LU)

(72) Inventors: Benjamin J. Clark, Santa Rosa, CA (US); David J. Hobbins, Galway (IE); Tim Huynh, Santa Rosa, CA (US); Grace Kelly, Galway (IE); Brian Kelly, Galway (IE)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 945 days.

(21) Appl. No.: 15/586,666

(22) Filed: May 4, 2017

(65) Prior Publication Data
US 2017/0296252 A1 Oct. 19, 2017

Related U.S. Application Data

(63) Continuation of application No. 14/397,476, filed as application No. PCT/US2013/028540 on Mar. 1, 2013, now abandoned.
(Continued)

(51) Int. Cl.
*A61B 18/02* (2006.01)
*A61B 90/00* (2016.01)
*A61B 18/00* (2006.01)

(52) U.S. Cl.
CPC ...... *A61B 18/02* (2013.01); *A61B 2018/0022* (2013.01); *A61B 2018/00404* (2013.01);
(Continued)

(58) Field of Classification Search
CPC .. A61B 2018/0005; A61B 2018/00011; A61B 2018/00023; A61B 2018/0022;
(Continued)

(56) References Cited

U.S. PATENT DOCUMENTS 3,125,096 A 3/1964 Antiles et al.
3,298,371 A 1/1967 Lee
(Continued)

FOREIGN PATENT DOCUMENTS

DE 4406451 A1 9/1995
DE 102005041601 4/2007
(Continued)

OTHER PUBLICATIONS

510K Summary of CryoGen Cryosurgery System, filed with FDA Jul. 3, 1997—approved Oct. 1, 1997, 1997, 5 pages.
(Continued)

*Primary Examiner* — Eun Hwa Kim

(57) ABSTRACT

Cryotherapeutic devices for renal neuromodulation and associated systems and methods are disclosed herein. A cryotherapeutic device configured in accordance with a particular embodiment of the present technology can include an elongated shaft having a distal portion and a supply lumen along at least a portion of the shaft. The shaft can be configured to locate the distal portion intravascularly at a treatment site proximate a renal artery or renal ostium. The supply lumen can be configured to receive a liquid refrigerant. The cryotherapeutic device can further include a cooling assembly at the distal portion of the shaft. The cooling assembly can include an applicator having a distributor in fluid communication with the supply lumen and a balloon configured to deliver cryotherapeutic cooling to nerves proximate the treatment site when the cooling assembly is in a deployed state.

16 Claims, 25 Drawing Sheets

Related U.S. Application Data

(60) Provisional application No. 61/639,852, filed on Apr. 27, 2012, provisional application No. 61/646,230, filed on May 11, 2012, provisional application No. 61/672,159, filed on Jul. 16, 2012.

(52) U.S. Cl.
CPC ............... *A61B 2018/00434* (2013.01); *A61B 2018/00511* (2013.01); *A61B 2018/00577* (2013.01); *A61B 2018/00791* (2013.01); *A61B 2018/00821* (2013.01); *A61B 2018/0212* (2013.01); *A61B 2018/0262* (2013.01); *A61B 2090/064* (2016.02)

(58) Field of Classification Search
CPC .. A61B 2018/0262; A61B 2018/00285; A61B 2018/00404; A61B 2018/0212; A61B 18/02
See application file for complete search history.

(56) References Cited

U.S. PATENT DOCUMENTS

| | | |
|---|---|---|
| 3,901,241 A | 8/1975 | Allen, Jr. |
| 3,924,628 A | 12/1975 | Droegemueller et al. |
| 4,275,734 A | 6/1981 | Mitchiner |
| 4,483,341 A | 11/1984 | Witteles |
| 4,602,624 A | 7/1986 | Naples et al. |
| 4,649,936 A | 3/1987 | Ungar et al. |
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,108,390 A | 4/1992 | Potocky et al. |
| 5,190,539 A | 3/1993 | Fletcher et al. |
| 5,300,068 A | 4/1994 | Rosar et al. |
| 5,308,323 A | 5/1994 | Sogawa et al. |
| 5,334,181 A | 8/1994 | Rubinsky et al. |
| 5,342,301 A | 8/1994 | Saab |
| 5,358,514 A | 10/1994 | Schulman et al. |
| 5,368,591 A | 11/1994 | Lennox et al. |
| 5,417,355 A | 1/1995 | Bersin |
| 5,423,744 A | 6/1995 | Gencheff et al. |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,624,392 A | 4/1997 | Saab |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,807,391 A | 6/1998 | Dobak, III et al. |
| 5,837,003 A | 11/1998 | Ginsburg |
| 5,860,970 A | 1/1999 | Goddard et al. |
| 5,860,974 A | 1/1999 | Abele |
| 5,865,787 A | 2/1999 | Shapland et al. |
| 5,868,735 A | 2/1999 | Lafontaine |
| 5,893,885 A | 4/1999 | Webster et al. |
| 5,902,299 A | 5/1999 | Jayaraman |
| 5,944,710 A | 8/1999 | Dev et al. |
| 5,954,719 A | 9/1999 | Chen et al. |
| 5,971,979 A | 10/1999 | Joye et al. |
| 5,983,141 A | 11/1999 | Sluijter et al. |
| 6,004,269 A | 12/1999 | Crowley et al. |
| 6,009,877 A | 1/2000 | Edwards |
| 6,012,457 A | 1/2000 | Lesh |
| 6,024,740 A | 2/2000 | Lesh et al. |
| 6,024,752 A | 2/2000 | Horn et al. |
| 6,032,675 A | 3/2000 | Rubinsky |
| 6,036,687 A | 3/2000 | Laufer et al. |
| 6,056,744 A | 5/2000 | Edwards |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,991 A | 11/2000 | Schatzberger |
| 6,142,993 A | 11/2000 | Whayne et al. |
| 6,149,620 A | 11/2000 | Baker et al. |
| 6,161,048 A | 12/2000 | Sluijter et al. |
| 6,161,049 A | 12/2000 | Rudie et al. |
| 6,161,543 A | 12/2000 | Cox et al. |
| 6,164,283 A | 12/2000 | Lesh |
| 6,190,356 B1 | 2/2001 | Bersin |
| 6,219,577 B1 | 4/2001 | Brown, III et al. |
| 6,224,592 B1 | 5/2001 | Eggers et al. |
| 6,241,722 B1 | 5/2001 | Li |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,283,959 B1 | 9/2001 | Lalonde et al. |
| 6,290,696 B1 | 9/2001 | Lafontaine |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,355,029 B1 | 3/2002 | Joye et al. |
| 6,405,732 B1 | 6/2002 | Edwards et al. |
| 6,413,255 B1 | 7/2002 | Stern |
| 6,428,534 B1 | 8/2002 | Joye et al. |
| 6,432,102 B2 | 8/2002 | Joye et al. |
| 6,451,045 B1 | 9/2002 | Walker et al. |
| 6,468,297 B1 | 10/2002 | Williams et al. |
| 6,488,679 B1 | 12/2002 | Swanson et al. |
| 6,496,737 B2 | 12/2002 | Rudie et al. |
| 6,497,703 B1 | 12/2002 | Korteling et al. |
| 6,506,189 B1 | 1/2003 | Rittman, III et al. |
| 6,514,226 B1 | 2/2003 | Levin et al. |
| 6,514,245 B1 | 2/2003 | Williams et al. |
| 6,517,533 B1 | 2/2003 | Swaminathan |
| 6,522,926 B1 | 2/2003 | Kieval et al. |
| 6,527,739 B1 | 3/2003 | Bigus et al. |
| 6,527,765 B2 | 3/2003 | Kelman et al. |
| 6,537,271 B1 | 3/2003 | Murray et al. |
| 6,540,734 B1 | 4/2003 | Chiu et al. |
| 6,542,781 B1 | 4/2003 | Koblish et al. |
| 6,551,309 B1 | 4/2003 | LePivert |
| 6,562,034 B2 | 5/2003 | Edwards et al. |
| 6,575,933 B1 | 6/2003 | Wittenberger et al. |
| 6,602,247 B2 | 8/2003 | Joye et al. |
| 6,610,083 B2 | 8/2003 | Keller et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,648,879 B2 | 11/2003 | Lafontaine |
| 6,666,858 B2 | 12/2003 | Lafontaine |
| 6,685,732 B2 | 1/2004 | Werneth |
| 6,685,648 B2 | 2/2004 | Flaherty et al. |
| 6,706,037 B2 | 3/2004 | Zvuloni et al. |
| 6,709,431 B2 | 3/2004 | Lafontaine |
| 6,711,444 B2 | 3/2004 | Koblish |
| 6,736,835 B2 | 5/2004 | Pellegrino et al. |
| 6,752,805 B2 | 6/2004 | Maguire et al. |
| 6,755,823 B2 | 6/2004 | Lalonde |
| 6,786,900 B2 | 9/2004 | Joye et al. |
| 6,786,901 B2 | 9/2004 | Joye et al. |
| 6,807,444 B2 | 10/2004 | Tu et al. |
| 6,811,550 B2 | 11/2004 | Holland et al. |
| 6,824,543 B2 | 11/2004 | Lentz |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,875,209 B2 | 4/2005 | Zvuloni et al. |
| 6,885,888 B2 | 4/2005 | Rezai |
| 6,893,436 B2 | 5/2005 | Woodard et al. |
| 6,905,510 B2 | 6/2005 | Saab |
| 6,908,462 B2 | 6/2005 | Joye et al. |
| 6,917,834 B2 | 7/2005 | Koblish et al. |
| 6,923,808 B2 | 8/2005 | Taimisto |

(56) References Cited

U.S. PATENT DOCUMENTS

| | | |
|---|---|---|
| 6,929,639 B2 | 8/2005 | Tairnisto |
| 6,939,346 B2 | 9/2005 | Kannenberg et al. |
| 6,949,097 B2 | 9/2005 | Stewart et al. |
| 6,955,174 B2 | 10/2005 | Joye et al. |
| 6,972,015 B2 | 12/2005 | Joye et al. |
| 6,981,382 B2 | 1/2006 | Lentz et al. |
| 6,989,009 B2 | 1/2006 | Lafontaine |
| 7,022,120 B2 | 2/2006 | Yon et al. |
| 7,060,062 B2 | 6/2006 | Joye et al. |
| 7,081,112 B2 | 7/2006 | Joye et al. |
| 7,081,115 B2 | 7/2006 | Taimisto |
| 7,101,368 B2 | 9/2006 | Lafontaine |
| 7,149,574 B2 | 12/2006 | Yun et al. |
| 7,156,840 B2 | 1/2007 | Lentz et al. |
| 7,162,303 B2 | 1/2007 | Levin et al. |
| 7,172,589 B2 | 2/2007 | Lafontaine |
| 7,189,227 B2 | 3/2007 | Lafontaine |
| 7,221,979 B2 | 5/2007 | Zhou et al. |
| 7,288,089 B2 | 10/2007 | Yon et al. |
| 7,300,433 B2 | 11/2007 | Lane et al. |
| 7,306,590 B2 | 12/2007 | Swanson |
| 7,357,797 B2 | 4/2008 | Ryba |
| 7,381,200 B2 | 6/2008 | Katoh et al. |
| 7,387,126 B2 | 6/2008 | Cox et al. |
| 7,390,894 B2 | 6/2008 | Weinshilboum et al. |
| 7,449,018 B2 | 11/2008 | Kramer |
| 7,487,780 B2 | 2/2009 | Hooven |
| 7,556,624 B2 | 3/2009 | Littrup et al. |
| 7,604,631 B2 | 10/2009 | Reynolds |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,758,571 B2 | 1/2010 | Joye et al. |
| 7,717,948 B2 | 5/2010 | Demarais et al. |
| 7,778,703 B2 | 8/2010 | Gross et al. |
| 7,785,289 B2 | 8/2010 | Rios et al. |
| 7,861,725 B2 | 1/2011 | Swanson |
| 7,972,327 B2 | 7/2011 | Eberl et al. |
| 8,012,147 B2 | 9/2011 | Lafontaine |
| 8,062,289 B2 | 11/2011 | Babaev |
| 8,080,006 B2 | 12/2011 | Lafontaine et al. |
| 8,088,125 B2 | 1/2012 | Lafontaine |
| 8,123,741 B2 | 2/2012 | Marrouche et al. |
| 8,128,617 B2 | 3/2012 | Bencini et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,261 B2 | 5/2012 | Watson |
| 8,439,909 B2 | 5/2013 | Wang et al. |
| 8,473,067 B2 | 6/2013 | Ingle et al. |
| 8,475,441 B2 | 7/2013 | Babkin et al. |
| 8,480,664 B2 | 7/2013 | Ingle et al. |
| 8,663,211 B2 | 3/2014 | Fourkas et al. |
| 8,740,895 B2 | 6/2014 | Mayse et al. |
| 8,777,943 B2 | 6/2014 | Mayse et al. |
| 9,101,343 B2 | 8/2015 | Duong et al. |
| 9,402,676 B2 | 8/2016 | Babkin et al. |
| 2002/0045893 A1 | 4/2002 | Lane et al. |
| 2002/0120258 A1 | 8/2002 | Lalonde |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0036752 A1 | 2/2003 | Joye et al. |
| 2003/0050635 A1 | 3/2003 | Truckai et al. |
| 2003/0050681 A1 | 3/2003 | Pianca et al. |
| 2003/0060762 A1 | 3/2003 | Zvuloni et al. |
| 2003/0060858 A1 | 3/2003 | Kieval et al. |
| 2003/0074039 A1 | 4/2003 | Puskas |
| 2003/0088189 A1 | 5/2003 | Tu et al. |
| 2003/0088240 A1 | 5/2003 | Saadat |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0024392 A1 | 2/2004 | Lewis et al. |
| 2004/0215186 A1 | 10/2004 | Cornelius et al. |
| 2004/0243119 A1 | 12/2004 | Lane et al. |
| 2004/0267250 A1 | 12/2004 | Yon et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0209587 A1 | 9/2005 | Joye et al. |
| 2005/0228460 A1 | 10/2005 | Levin et al. |
| 2005/0240117 A1 | 10/2005 | Zvuloni et al. |
| 2006/0084962 A1 | 4/2006 | Joye et al. |
| 2006/0085054 A1 | 4/2006 | Zikorus et al. |
| 2006/0095029 A1 | 5/2006 | Young et al. |
| 2006/0206150 A1 | 9/2006 | Demarais et al. |
| 2006/0212027 A1 | 9/2006 | Marrouche et al. |
| 2006/0247611 A1 | 11/2006 | Abboud et al. |
| 2006/0271111 A1 | 11/2006 | Demarais et al. |
| 2007/0049924 A1 | 3/2007 | Rahn |
| 2007/0093710 A1 | 4/2007 | Maschke |
| 2007/0129720 A1 | 6/2007 | Demarais et al. |
| 2007/0185445 A1 | 8/2007 | Nahon et al. |
| 2007/0265687 A1 | 11/2007 | Deem et al. |
| 2007/0299433 A1* | 12/2007 | Williams ............... A61B 18/02 606/21 |
| 2008/0097251 A1 | 4/2008 | Babaev |
| 2008/0171974 A1 | 7/2008 | Lafontaine et al. |
| 2008/0208182 A1 | 8/2008 | Lafontaine et al. |
| 2008/0300584 A1 | 12/2008 | Lentz et al. |
| 2008/0306475 A1 | 12/2008 | Lentz et al. |
| 2008/0312644 A1 | 12/2008 | Fourkas et al. |
| 2008/0319513 A1 | 12/2008 | Pu et al. |
| 2009/0036948 A1 | 2/2009 | Levin et al. |
| 2009/0171333 A1 | 7/2009 | Hon |
| 2009/0182316 A1 | 7/2009 | Bencini |
| 2009/0182317 A1 | 7/2009 | Bencini |
| 2009/0209949 A1 | 8/2009 | Ingle et al. |
| 2009/0221955 A1 | 9/2009 | Babaev |
| 2009/0281533 A1 | 11/2009 | Ingle et al. |
| 2009/0287202 A1 | 11/2009 | Ingle et al. |
| 2009/0299355 A1 | 12/2009 | Bencini et al. |
| 2010/0049184 A1 | 2/2010 | George et al. |
| 2010/0069900 A1 | 3/2010 | Shirley et al. |
| 2010/0100087 A1 | 4/2010 | Mazzone et al. |
| 2010/0106148 A1 | 4/2010 | Joye et al. |
| 2010/0114269 A1 | 5/2010 | Wittenberger et al. |
| 2010/0125266 A1 | 5/2010 | Deem et al. |
| 2010/0130970 A1* | 5/2010 | Williams ........ A61M 25/10185 606/21 |
| 2010/0137860 A1 | 6/2010 | Demarais et al. |
| 2010/0137952 A1 | 6/2010 | Demarais et al. |
| 2010/0179526 A1 | 7/2010 | Lawrence |
| 2010/0179527 A1 | 7/2010 | Watson et al. |
| 2010/0191112 A1 | 7/2010 | Demarais et al. |
| 2010/0198203 A1 | 8/2010 | Kuck et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0234838 A1 | 9/2010 | Watson |
| 2010/0249766 A1 | 9/2010 | Saadat |
| 2010/0256621 A1 | 10/2010 | Babkin et al. |
| 2010/0280507 A1 | 11/2010 | Babkin et al. |
| 2011/0125143 A1 | 5/2011 | Gross et al. |
| 2011/0152855 A1 | 6/2011 | Mayse et al. |
| 2011/0257642 A1 | 10/2011 | Griggs, III |
| 2011/0263921 A1 | 10/2011 | Vrba et al. |
| 2011/0270238 A1 | 11/2011 | Rizq et al. |
| 2011/0282272 A1 | 11/2011 | Lafontaine |
| 2012/0029509 A1 | 2/2012 | Smith |
| 2012/0029511 A1 | 2/2012 | Smith et al. |
| 2012/0089047 A1* | 4/2012 | Ryba .................... A61B 18/02 600/554 |

(56) References Cited

U.S. PATENT DOCUMENTS

| | | | |
|---|---|---|---|
| 2012/0109021 A1 | 5/2012 | Hastings et al. | |
| 2012/0123261 A1 | 5/2012 | Jenson et al. | |
| 2012/0130289 A1 | 5/2012 | Demarais et al. | |
| 2012/0130345 A1 | 5/2012 | Levin et al. | |
| 2012/0130360 A1* | 5/2012 | Buckley | A61B 18/02 606/22 |
| 2012/0130368 A1 | 5/2012 | Jenson | |
| 2012/0136417 A1 | 5/2012 | Buckley et al. | |
| 2012/0136418 A1 | 5/2012 | Buckley et al. | |
| 2012/0143097 A1 | 6/2012 | Pike, Jr. | |
| 2012/0143177 A1 | 6/2012 | Avitall | |
| 2012/0150267 A1 | 6/2012 | Buckley et al. | |
| 2012/0172837 A1 | 7/2012 | Demarais et al. | |
| 2012/0245574 A1* | 9/2012 | Lalonde | A61B 18/02 606/21 |
| 2012/0253336 A1 | 10/2012 | Littrup et al. | |
| 2013/0090650 A1 | 4/2013 | Jenson et al. | |
| 2013/0123770 A1 | 5/2013 | Smith | |
| 2013/0184696 A1 | 7/2013 | Fourkas et al. | |
| 2014/0046313 A1 | 2/2014 | Pederson et al. | |
| 2014/0066914 A1 | 3/2014 | Lafontaine | |
| 2014/0276724 A1 | 9/2014 | Goshayeshgar | |
| 2014/0276728 A1 | 9/2014 | Goshayeshgar | |
| 2014/0276811 A1 | 9/2014 | Koblish et al. | |
| 2015/0105764 A1 | 4/2015 | Rizq et al. | |

FOREIGN PATENT DOCUMENTS

| | | |
|---|---|---|
| EP | 0655225 A1 | 5/1995 |
| EP | 0955012 A1 | 11/1999 |
| EP | 1129670 A1 | 9/2001 |
| EP | 1164963 A1 | 1/2002 |
| EP | 1389477 A1 | 2/2004 |
| EP | 1502533 A1 | 2/2005 |
| EP | 1559362 A2 | 8/2005 |
| EP | 2558016 A2 | 2/2013 |
| EP | 2598070 A1 | 6/2013 |
| EP | 2598071 A2 | 6/2013 |
| EP | 2608837 A2 | 7/2013 |
| GB | 1422535 A | 1/1976 |
| GB | 2283678 | 5/1995 |
| GB | 2289414 A | 11/1995 |
| SU | 718099 A1 | 2/1980 |
| SU | 1153901 A1 | 5/1985 |
| SU | 1329781 A2 | 8/1987 |
| SU | 1378835 A1 | 3/1988 |
| SU | 1771725 | 10/1992 |
| WO | WO-1994007446 A1 | 4/1994 |
| WO | WO-1995025472 A1 | 9/1995 |
| WO | WO-1995031142 A1 | 11/1995 |
| WO | WO-1997025011 | 7/1997 |
| WO | WO-1997036548 A1 | 10/1997 |
| WO | WO-1998042403 A1 | 10/1998 |
| WO | WO-1999000060 A1 | 1/1999 |
| WO | WO-1999005979 | 2/1999 |
| WO | WO-1999027862 A1 | 6/1999 |
| WO | WO-2000047118 | 8/2000 |
| WO | WO-2001022897 A1 | 4/2001 |
| WO | WO-2001064145 A1 | 9/2001 |
| WO | WO-2001070114 A1 | 9/2001 |
| WO | WO-2002000128 A2 | 1/2002 |
| WO | WO-2002004042 A2 | 1/2002 |
| WO | WO-2002007625 A2 | 1/2002 |
| WO | WO-2002007628 A2 | 1/2002 |
| WO | WO-2002013710 A1 | 2/2002 |
| WO | WO-2002015807 | 2/2002 |
| WO | WO-2002058576 A1 | 8/2002 |
| WO | WO-2003020334 A2 | 3/2003 |
| WO | WO-2003022167 | 3/2003 |
| WO | WO-2003061496 A1 | 7/2003 |
| WO | WO-2003/082080 | 10/2003 |
| WO | WO-2005030072 A1 | 4/2005 |
| WO | WO-2005038357 A2 | 4/2005 |
| WO | WO--2005041748 A2 | 5/2005 |
| WO | WO-2005/110528 A1 | 11/2005 |
| WO | WO-2006041881 A2 | 4/2006 |
| WO | WO-2006096272 A1 | 9/2006 |
| WO | WO-2006105121 A2 | 10/2006 |
| WO | WO-2006124177 A1 | 11/2006 |
| WO | WO-2007008954 A2 | 1/2007 |
| WO | WO-2007078997 A2 | 7/2007 |
| WO | WO-2008049084 A2 | 4/2008 |
| WO | WO-2008131037 A2 | 10/2008 |
| WO | WO-2011056684 A2 | 5/2011 |
| WO | WO-2011082278 A1 | 7/2011 |
| WO | WO-2011082279 A2 | 7/2011 |
| WO | WO-2012016135 A1 | 2/2012 |
| WO | WO-2012016137 A2 | 2/2012 |
| WO | WO-2012058430 A2 | 5/2012 |
| WO | WO-2013074683 A1 | 5/2013 |
| WO | WO-2013106859 A1 | 7/2013 |
| WO | WO-2013162700 | 10/2013 |
| WO | WO-2014/150204 A1 | 9/2014 |
| WO | WO-2014/158727 A1 | 10/2014 |
| WO | WO-2014/164445 A1 | 10/2014 |

OTHER PUBLICATIONS

CO2/Gas Composite Regulator, Sep. 26, 2011, 2 pages. <http://www.genuineinnovations.com/composite-regulator.html>.

CryoGen SS&E: HerOption Uterine Cryoblatin Therapy System, filed with FDA Aug. 15, 2000—approved Apr. 20, 2001,1999, 84 pages.

International Search Report and Written Opinion for International Application No. PCT/US2012/063411 dated Jun. 13, 2013, 13 pages.

Lura Harrison, PH.D, et al., "Cryosurgical Ablation of the A-V Node-His Bundle—A New Method for Producing A-V Block," Circulation, vol. 55, 1977 pp. 463-470.

Medical Grade Gas Dispenser, Sep. 6, 2011, 1 page, <http://www.abd-inc.com/Frame/904990-page1namepage904990.html?refresh=120542262133>.

Sesia G. et al., "The use of nitrous oxide as a freezing agent in cryosurgery of the prostate," International Surgery [Int Surg], vol. 53, 1970, pp. 82-90.

Special Order Only Thermal Dilution injector, Obsolete Product, Sep. 6, 2011, 1 page, <http://www,abd-inc,com/Frame-904990-page1namepage904990.html?refresh=1205442262133>.

Torre, Douglas, MD, "Alternate Cryogens for Cryosurgery," J. Derm. Surgery, Jun. 1975, pp. 56-58.

Voityna SV, "Cocatheter-tourniquet," Meditsinskaia Tekhnika [Med Tekh], vol. 6, 1976, pp. 47-48.

Search Report and Written Opinion dated Sep. 27, 2013 for PCT Application No. PCT/US2013/028540.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter,"Journal of the American College of Cardiology, 1999; 33; pp. 972-984.

Beale et al., "Minimally Invasive Treatment for Varicose Veins: A Review of Endovenous Laser Treatment and Radiofrequency Ablation". Lower Extremity Wounds 3(4), 2004, 10 pages.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.

Excerpt of Operator's Manual of Boston Scientific's EPT-1000 XP Cardiac Ablation Controller & Accessories, Version of Apr. 2003, (6 pages).

(56) References Cited

OTHER PUBLICATIONS

Excerpt of Operator's Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. 2465470, Granted Oct. 28, 2015, Date of Opposition Jul. 27, 2016, 34 pages.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Opposition to European Patent No. EP2092957, Granted Jan. 5, 2011, Date of Opposition Oct. 5, 2011, 26 pages.

Oz, Mehmet, Pressure Relief, TIME, Jan. 9, 2012, 2 pages. <www.time.com/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Pieper, et al., "Design and Implementation of a New Computerized System for Intraoperative Cardiac Mapping" Journal of Applied Physiology, 1991, vol. 71 (4), pp. 1529-1539.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.

Schneider, Peter A., "Endovascular Skills—Guidewire and Catheter Skills for Endovascular Surgery," Second Edition Revised and Expanded, 10 pages, (2003).

ThermoCool Irrigated Catheter and Integrated Ablation System, Biosense Webster (2006), 6 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

U.S. Appl. No. 11/363,867, filed Feb. 27, 2006, 70 pages.

U.S. Appl. No. 60/813,589, filed Dec. 29, 2005, 62 pgs.

U.S. Appl. No. 60/852,787, filed Oct. 18, 2006, 112 pgs.

Ureter, https://en.wikipedia.org/wiki/Ureter, Jun. 2016, 6 pgs.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, The American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

Schlaich, M.P. et al., "Renal Denervation as a Therapeutic Approach for Hypertension: Novel Implications for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16: 1 page.

Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

(56) References Cited

OTHER PUBLICATIONS

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n. I.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using Pet and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.
Dubuc, M., et al. "Feasibility of cardiac cryoablation using a transvenous steerable electrode catheter." J Intery Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gelfand, M., et al., "Treatment of renal failure and hypertension." U.S. Provisional Patent Application No. 60/442,970, filed Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery embolization with diluted hot contrast medium: an experimental study." J Vasc Intery Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S. J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D. L., et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.

(56) References Cited

OTHER PUBLICATIONS

Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, Renal Denervation and Symplicity HTN-3: "Dubium Sapientiae Initium" (Doubt Is the Beginning of Wisdom), Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

* cited by examiner

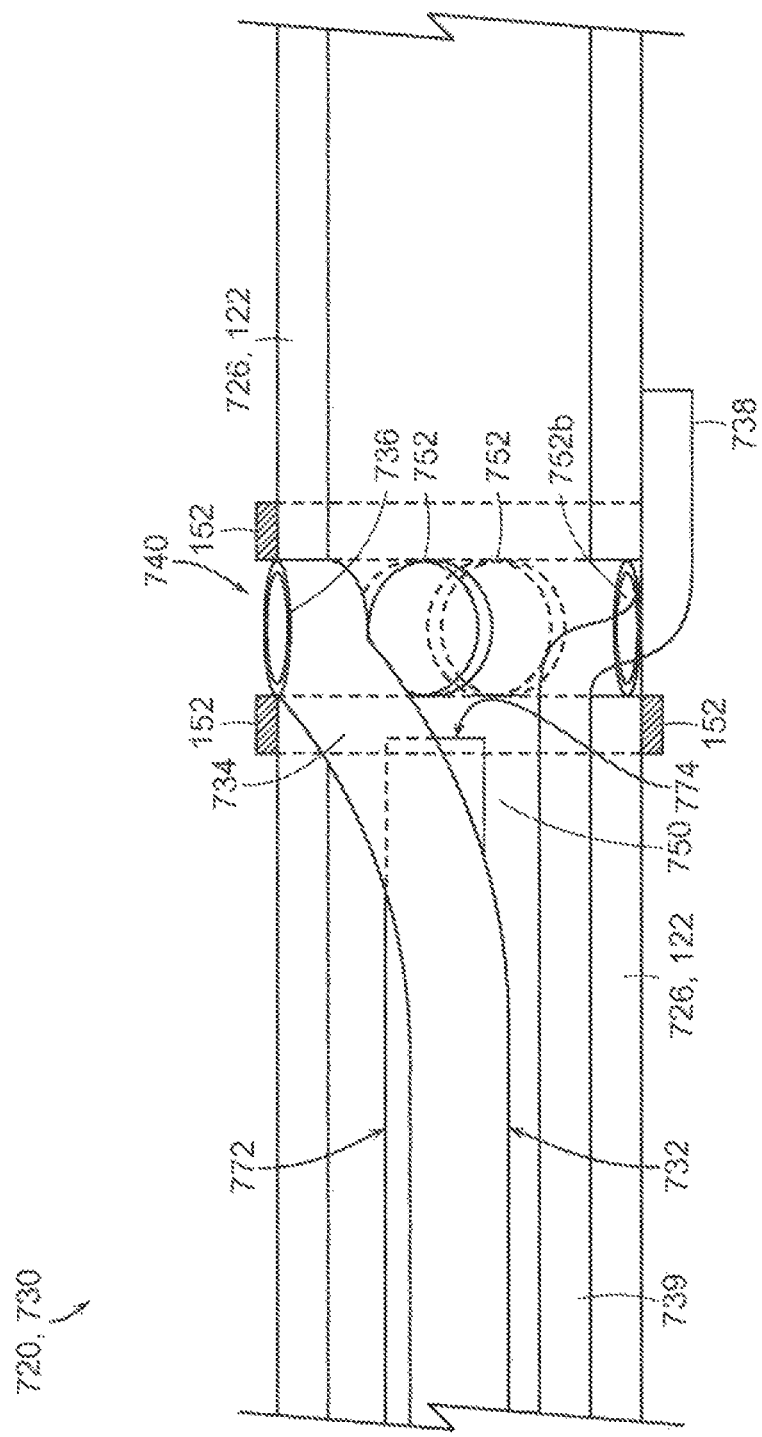

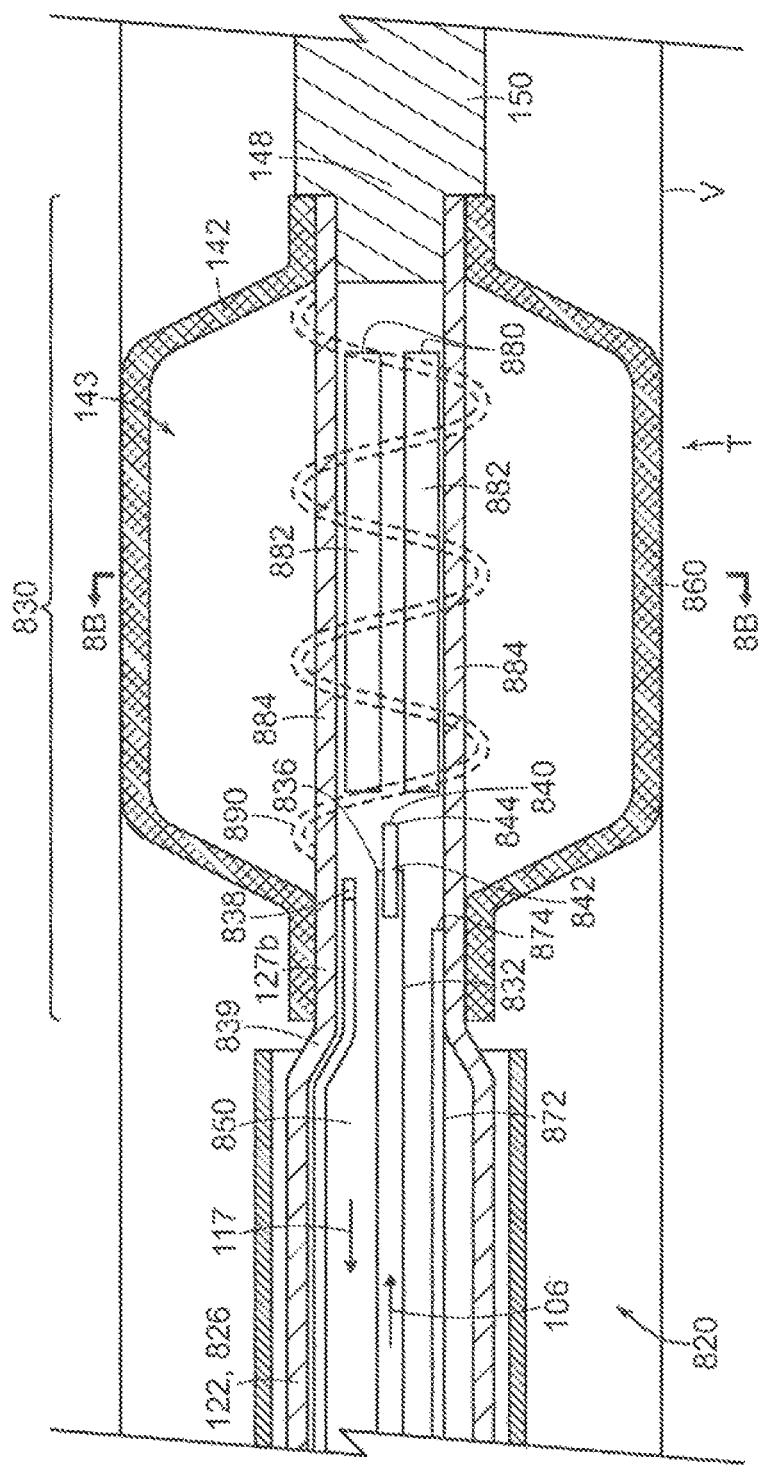

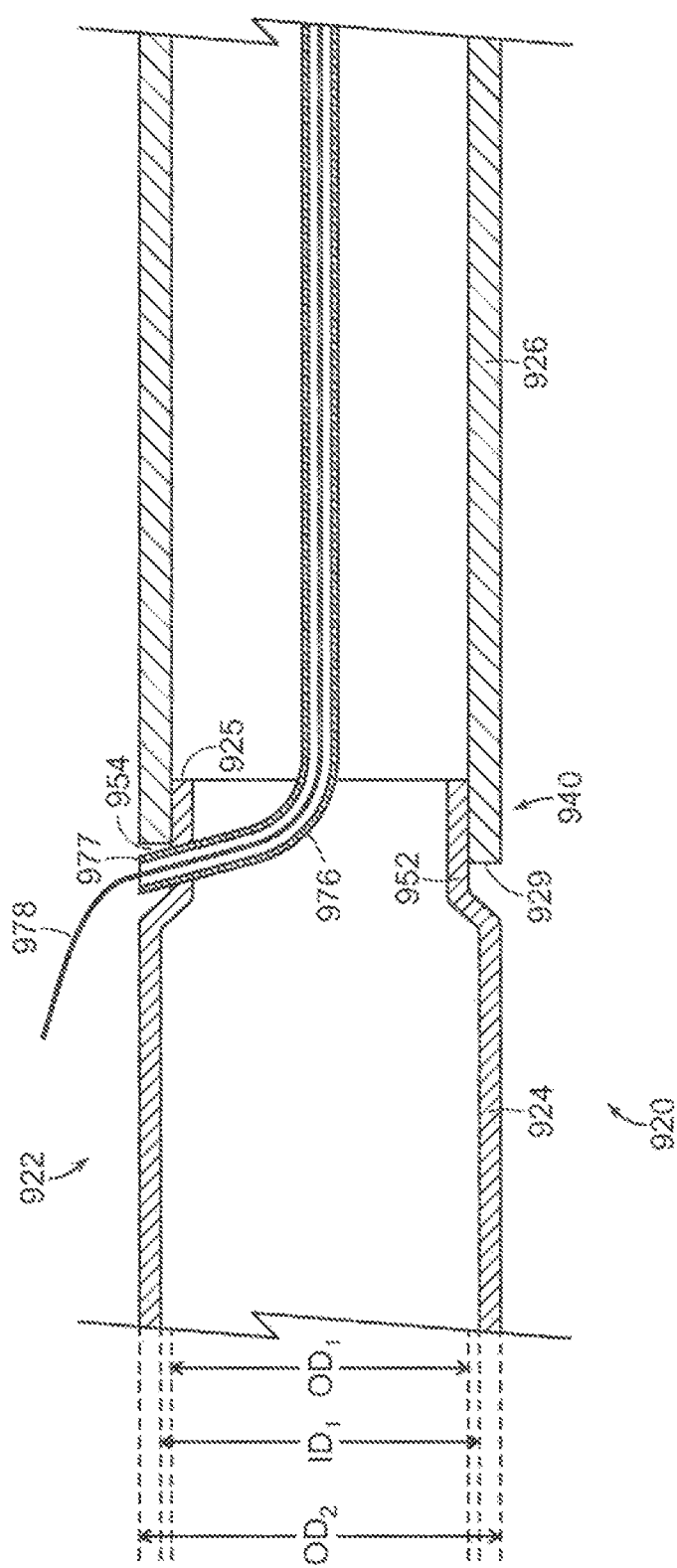

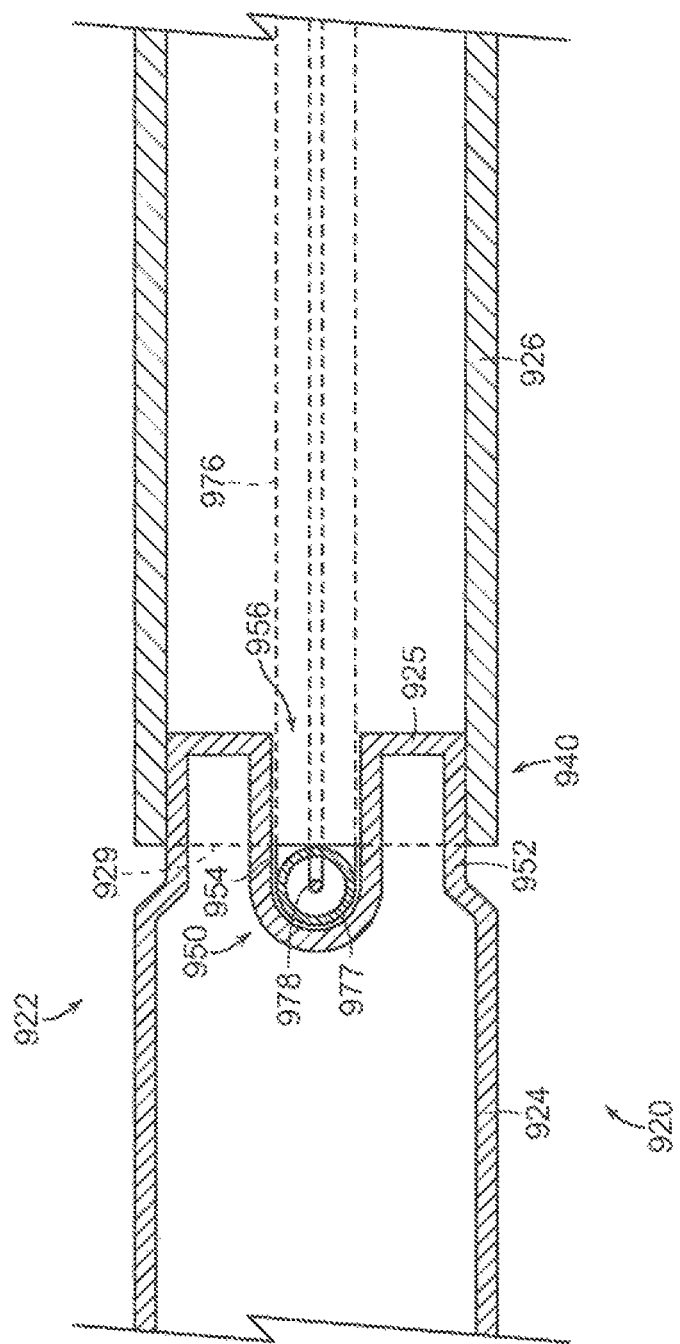

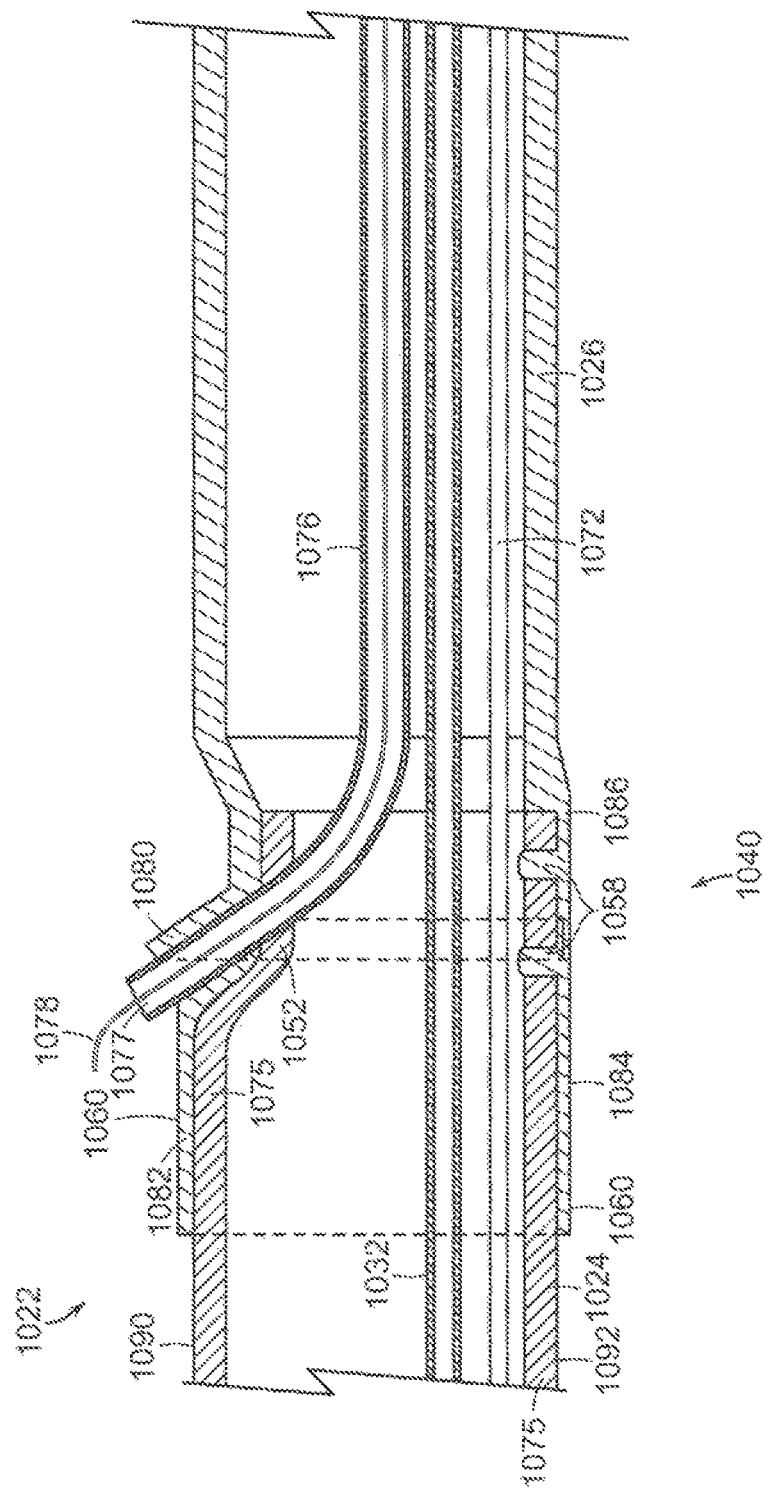

Arterial Vasculature

Venous Vasculature

CRYOTHERAPEUTIC DEVICES FOR RENAL NEUROMODULATION AND ASSOCIATED SYSTEMS AND METHODS

CROSS-REFERENCE TO RELATED APPLICATIONS

This application is a continuation of U.S. application Ser. No. 14/397,476, which is a U.S. National Stage application of International Application No. PCT/US2013/028540, which claims the benefit of the following applications:

(a) U.S. Provisional Application No. 61/672,159, filed Jul. 16, 2012;

(b) U.S. Provisional Application No. 61/646,230, filed May 11, 2012; and (c) U.S. Provisional Application No. 61/639,852, filed Apr. 27, 2012.

The foregoing applications are incorporated herein by reference in their entireties. As such, components and features of embodiments disclosed in these applications may be combined with various components and features disclosed in the present application.

ADDITIONAL APPLICATIONS INCORPORATED BY REFERENCE

U.S. patent application Ser. No. 13/279,330, filed Oct. 23, 2011, U.S. Provisional Application No. 61/545,052, filed Oct. 7, 2011, U.S. patent application Ser. No. 13/204,504, filed Aug. 5, 2011, PCT International Application No. PCT/US2011/46845, filed Aug. 5, 2011, and U.S. Provisional Application No. 61/371,110, filed Aug. 5, 2010, are incorporated herein by reference in their entireties. As such, components and features of embodiments disclosed in these applications may be combined with various components and features disclosed in the present application.

TECHNICAL FIELD

The present technology relates generally to cryotherapeutic devices. In particular, several embodiments are directed to cryotherapeutic devices for intravascular neuromodulation and associated systems and methods.

BACKGROUND

The primary function of the sympathetic nervous system (SNS) is the mobilization of hormonal and neuronal networks within the body, primarily in response to acute or chronic stress. The SNS fibers innervate tissue in almost every internal organ system of the human body for mediating physiological homeostasis for a variety of body functions. For example the SNS continuously and involuntarily counteracts the parasympathetic nervous system (PNS) by affecting, for example, dilation of pupils, cardiac output, blood pressure, and urinary output. Such regulation can have adaptive utility in maintaining homeostasis or in preparing the body for rapid response to environmental factors. Under normal circumstances, the SNS utilizes active coping strategies to respond to both internal (e.g., low blood sugar) and environmental (fight/flee a foe) threats. Chronic activation of the SNS, however, is a common maladaptive response that can drive the progression of many disease states. Renal sympathetic nerve activity has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension. Hypertension is also characterized by an increased rate of sympathetic-nerve firing, possibly modulated by afferent signaling from renal sensory nerves.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from renal sensory receptors in diseased kidneys are major contributors to initiating and sustaining elevated central sympathetic outflow with consequences for arterial pressure misregulation.

Sympathetic nerves to the kidneys terminate in the blood vessels, the juxtaglomerular apparatus, and the renal tubules. Stimulation of the renal sympathetic nerves can cause increased renin release, increased tubular sodium ($Na^+$) reabsorption, and a reduction of renal blood flow. These aspects of renal function are considerably stimulated (elevated) in disease states characterized by heightened sympathetic tone and likely contribute to increased blood pressure in hypertensive patients. The reduction of renal blood flow and glomerular filtration rate as a result of renal sympathetic efferent stimulation is likely a major contributor to the loss of renal function in cardio-renal syndrome (i.e., renal dysfunction as a progressive complication of chronic heart failure). Pharmacologic strategies to counteract the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Accordingly, there is a strong public-health need for alternative treatment strategies.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIG. 7B is an enlarged side view of the distal portion of FIG. 7A in accordance with an embodiment of the present technology.

FIGS. 8A and 8B are enlarged side and end cross-sectional views of a cryotherapeutic device configured in accordance with another embodiment of the present technology.

FIGS. 9A and 9B are enlarged cross-sectional and top plan views of proximal and distal portions of a cryotherapeutic device configured in accordance with yet another embodiment of the present technology.

FIGS. 10A and 10B are enlarged cross-sectional views of proximal and independent distal portions of a cryotherapeutic device configured in accordance with a further embodiment of the present technology.

DETAILED DESCRIPTION

Figure 1:
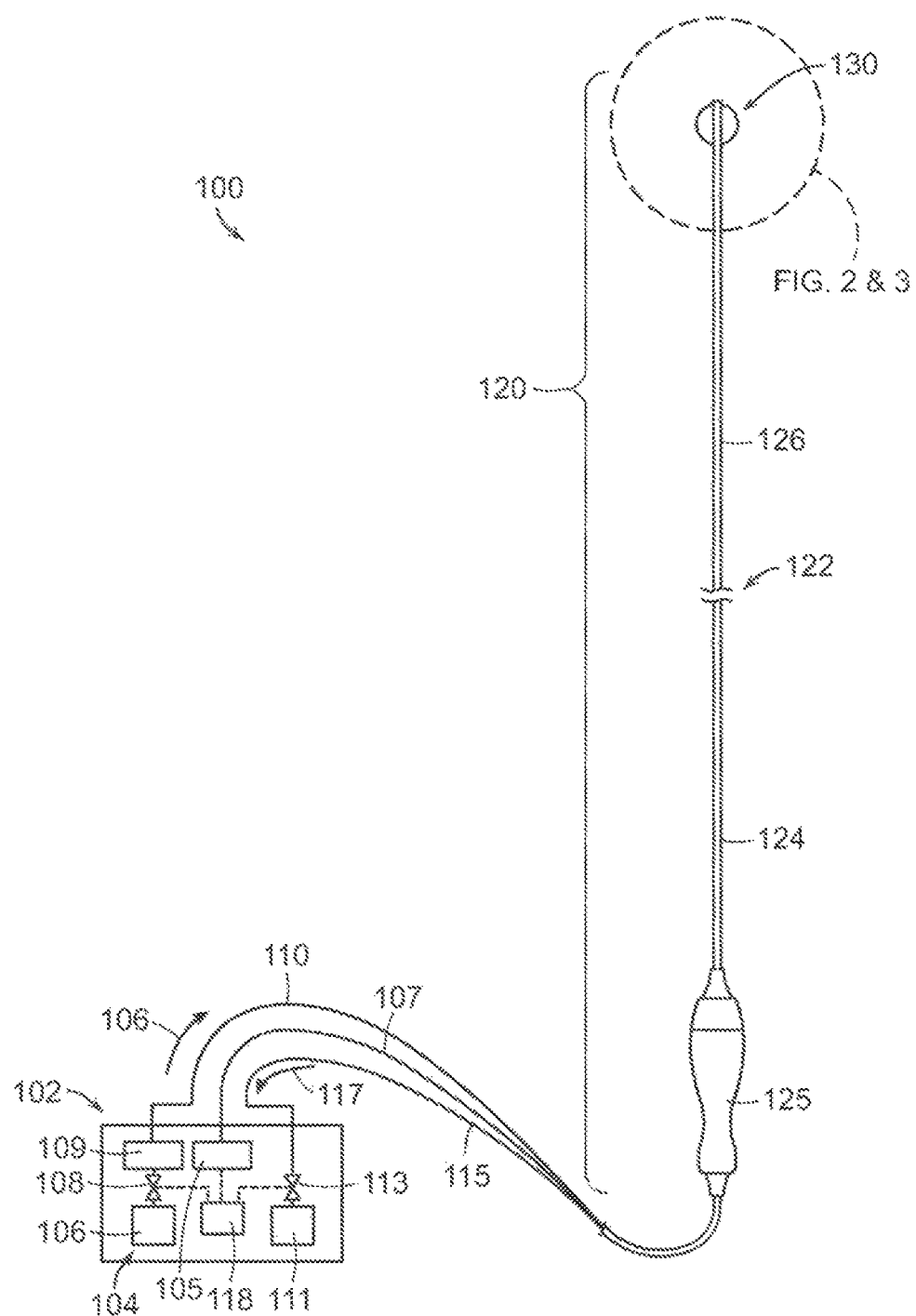
FIG. 1 illustrates a cryotherapeutic system in accordance with an embodiment of the present technology.

Specific details of several embodiments of the technology are described below with reference to FIGS. 1-16B. Although many of the embodiments are described below with respect to devices, systems, and methods for intravascular modulation of renal nerves using cryotherapeutic approaches, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-16B.

With regard to the terms "distal" and "proximal" within this description, unless otherwise specified, the terms can reference a relative position of the portions of a cryotherapeutic device and/or an associated delivery device with reference to an operator and/or a location in the vasculature. For example, proximal can refer to a position closer to the operator of the device or an incision into the vasculature, and distal can refer to a position that is more distant from the operator of the device or further from the incision along the vasculature. For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function. The headings provided herein are for convenience only.

Cryotherapy and Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic overstimulation such as hypertension, heart failure, acute myocardial infarction, metabolic syndrome, insulin resistance, diabetes, left ventricular hypertrophy, chronic and end stage renal disease, osteoporosis, inappropriate fluid retention in heart failure, cardio-renal syndrome, and sudden death. The reduction of afferent neural signals from the kidneys contributes to the systemic reduction of sympathetic tone/drive. Renal neuromodulation is expected to be useful in treating several conditions associated with systemic sympathetic overactivity or hyperactivity and can potentially benefit a variety of organs and bodily structures innervated by sympathetic nerves. For example, a reduction in central sympathetic drive may reduce insulin resistance that afflicts patients with metabolic syndrome and Type II diabetics. A more detailed description of pertinent patient anatomy and physiology is provided below.

Various techniques can be used to partially or completely incapacitate neural pathways, such as those innervating the kidneys. Cryotherapy, for example, includes cooling tissue at a target site in a manner that modulates neural function. The mechanisms of cryotherapeutic tissue damage include, for example, direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

Cryotherapy has certain characteristics that can be beneficial for intravascular renal neuromodulation. For example, rapidly cooling tissue provides an analgesic effect such that cryotherapies may be less painful than ablating tissue at high temperatures. Cryotherapies may thus require less analgesic medication to maintain patient comfort during a procedure compared to heat ablation procedures. Additionally, reducing pain mitigates patient movement and thereby increases operator success and reduces procedural complications. Cryotherapy also typically does not cause significant collagen tightening, and thus cryotherapy is not typically associated with vessel stenosis. Cryotherapies generally operate at temperatures that cause cryotherapeutic applicators to adhere to moist tissue. This can be beneficial because it promotes stable, consistent, and continued contact during treatment. The typical conditions of treatment can make this an attractive feature because, for example, a patient can move during treatment, a catheter associated with an applicator can move, and/or respiration can cause the kidneys to rise and fall and thereby move the renal arteries. In addition, blood flow is pulsatile and causes the renal arteries to pulse. Adhesion associated with cryotherapeutic cooling also can be advantageous when treating short renal arteries in which stable intravascular positioning can be more difficult to achieve.

Selected Embodiments of Renal Cryogenic Systems

Introductory examples of cryotherapeutic systems, system components and associated methods in accordance with embodiments of the present technology are described in this section with reference to FIGS. 1-5. Although this disclosure is primarily directed to cryotherapeutic system components for renal neuromodulation configured to be inside the vasculature, for purposes of introduction, FIGS. 1-5 are described in this section with emphasis on both cryotherapeutic-system components configured to be outside the vasculature and cryotherapeutic-system components configured to be inside the vasculature. It will be appreciated that specific elements, substructures, advantages, uses, and/or other features of the embodiments described with reference to FIGS. 1-5 can be suitably interchanged, substituted or otherwise configured with one another and/or with the embodiments described with reference to FIGS. 6-12E in accordance with additional embodiments of the present technology. Furthermore, suitable elements of the embodiments described with reference to FIGS. 1-5 can be used as stand-alone and/or self-contained devices.

FIG. 1 is a partially schematic diagram illustrating a cryotherapeutic system 100 configured in accordance with several embodiments of the present technology. The cryotherapeutic system 100 can include a console 102 and a cryotherapeutic device 120. The console 102 can include a supply container 104, a refrigerant 106 in the supply container 104, and a supply control valve 108 in fluid communication with the supply container 104. The supply container 104 can be, for example, a single-use cartridge or a larger container (e.g., a canister, tank, or other suitable container) that contains a sufficient volume of refrigerant 106 to perform multiple procedures. The larger supply containers, for example, can be refillable cylinders. The supply container 104 can be configured to retain the refrigerant 106 at a desired pressure. For example, in one embodiment, the supply container 104 can be configured to house liquid $N_2O$ at a pressure of 750 psi or greater, thereby allowing the $N_2O$ to be in a substantially liquid phase at about ambient temperatures. In other embodiments, the refrigerant 106 can include carbon dioxide, a hydrofluorocarbon ("HFC"; e.g., Freon®, R-410A, etc.), and/or other suitable refrigerant material in a compressed or condensed state that can be retained in the supply container 104 at a sufficiently high pressure to maintain the refrigerant 106 in at least a substantially liquid state at about ambient temperatures (e.g., approximately 210 psi for R-410A). In some embodiments, the cryotherapeutic system 100 can be configured to pre-cool the refrigerant 106, which can increase the cooling potential of the refrigerant 106. The console 102, for example, can include a pre-cooler 109. In other embodiments, the system 100 can include a pre-cooler along the supply line 110, at a handle at a proximal region of the system 100, or elsewhere coupled to the cryotherapeutic device 120. Pre-cooling is described, for example, in more detail in U.S. patent application Ser. No. 13/279,330, U.S. Provisional Application No. 61/639,852, and PCT International Application No. PCT/US2011/057504, the subject matter of which are incorporated herein by reference in their entireties.

The supply console 102 can include a supply line 110 for transporting refrigerant to the cryotherapeutic device 120 from the supply container 104 and/or other supply console 102 components. The supply control valve 108, which can be configured to operate manually or automatically, is coupled to the supply line 110 and suitable to control the flow of refrigerant 106 to the cryotherapeutic device 120. The console 102 can additionally include a pump 111 and/or a backpressure control valve 113, and an exhaust line 115. The exhaust line 115 can be configured to receive and transport exhausted refrigerant 117 from the cryotherapeutic device 120, and the back-pressure control valve 113 and/or pump 111 can be operatively coupled to the exhaust line 115. In one embodiment, the pump 111 can be a vacuum pump. In another embodiment (not shown), the pump 111 can be a DC power pump. The pump 111 can be configured to reduce the backpressure of evaporated refrigerant 117 and, in conjunction with increasing the flow rate of refrigerant 106 using the supply control valve 108, can increase the refrigeration potential of the refrigerant 106. In other embodiments, the exhausted refrigerant 117 can be exhausted to ambient pressure.

The console 102 can further include a controller 118 having, for example, a processor (not shown) or dedicated circuitry (not shown) to implement a computerized algorithm for executing a treatment procedure or a portion of a treatment procedure automatically. The console 102 may also include an optional user interface that receives user input and/or provides information to the user and/or circuitry for monitoring optional sensors (e.g., pressure or temperature) if present in the cryotherapeutic device 120. In one embodiment, the controller 118 operates the backpressure control valve 113 to control the amount of vacuum applied to the exhausted refrigerant 117 for controlling temperature in the cryotherapeutic device 120. In another embodiment, the controller 118 can govern the supply control valve 108 and/or the backpressure control valve 113 for increasing the backpressure of exhausted refrigerant 117, for example, to increase the boiling point of the refrigerant 106. In a specific example, a slight increase in backpressure from 1 atm to about 2 atm would raise the boiling point of $N_2O$ from about −88° C. to about −75° C.; an increase in backpressure to 3 atm would raise the boiling point to about −65° C.

As further shown in FIG. 1, the console 102 can also include a pressure transducer or sensor 105 (e.g., a PX209-100G5V pressure transducer made by Omega Engineering of Stamford, Conn.) coupled to a pressure line 107 to monitor pressure within a portion (e.g., an expansion chamber or balloon, not shown) of the cooling assembly 130 during a treatment procedure. In some embodiments, the pressure sensor 105 can be coupled to the controller 118 to serve as a feedback mechanism configured to control the supply control valve 108 and/or the backpressure control valve 113. In these embodiments, refrigerant flow to and/or from the cooling assembly 130 can be adjusted in response to a pressure sensed at the cooling assembly 130. For example, the pressure sensor 105 can be configured to indicate a pressure above a predetermined threshold value or range (e.g., a value or range of a burst pressure of a balloon, not shown, of the cooling assembly 130). In response, the controller 118 can decrease or terminate the flow of refrigerant 106 to the cryotherapeutic device 120 by at least partially closing the supply control valve 108. Similarly, the flow of refrigerant 106 to the cooling assembly 130 can be increased by reducing the back pressure of the exhausted refrigerant 117 in the exhaust line 115 (e.g., using the vacuum pump 111). In other embodiments, the pressure sensor 105 can be coupled directly to the supply control valve 108 and/or the backpressure control valve 113 to automatically regulate the valves 108 and 113 in response to a sensed pressure. The cryotherapeutic system 100 can be configured to verify that the pressure sensor 105 is calibrated properly before a treatment procedure. For example, the system 100 can automatically check the functionality of the pressure sensor 105 as the system 100 powers on by comparing a pressure reading from the pressure sensor 105 with the ambient pressure.

During cryotherapeutic treatments, the pressure sensor 105 (FIG. 1) can be configured to provide a signal indicating a change in pressure within the expansion chamber or balloon (not shown) of the cooling assembly 130 (via a pressure monitoring lumen, not shown, located at or near the cooling assembly 130). For example, the pressure sensor 105 can be configured to indicate a threshold pressure below the rupture pressure of the balloon to reduce the likelihood that the balloon bursts during cryotherapy. The balloon may have a burst pressure dependent at least in part on the material from which the balloon is made. Compliant materials (e.g., polyurethane), for example, typically have lower burst pressures (e.g., 80 psi, 100 psi, 200 psi, etc.) than non-compliant materials (e.g., nylon) that can have burst pressures of 300 psi or higher. The pressure sensor 105 can be configured to monitor a threshold pressure, which may be equal to a pressure value below the burst pressure that provides an adequate response time to react to the change in pressure before the balloon ruptures. In other embodiments, the pressure sensor 105 can be configured to indicate when the balloon operates outside its desired operating pressure (e.g., 20-60 psi).

As shown in FIG. 1, the cryotherapeutic device 120 includes an elongated shaft 122 that has a proximal portion 124, a handle 125 at a proximal region of the proximal portion 124, and a distal portion 126 extending distally relative to the proximal portion 124. The cryotherapeutic device 120 can further include a cooling assembly 130 at the distal portion 126 of the shaft 122. The shaft 122 can be configured to locate the distal portion 126 intravascularly at a treatment site proximate (e.g., in or near) a renal artery or renal ostium, and the cooling assembly 130 is configured to provide therapeutically-effective cryogenic renal neuromodulation.

Figure 2:
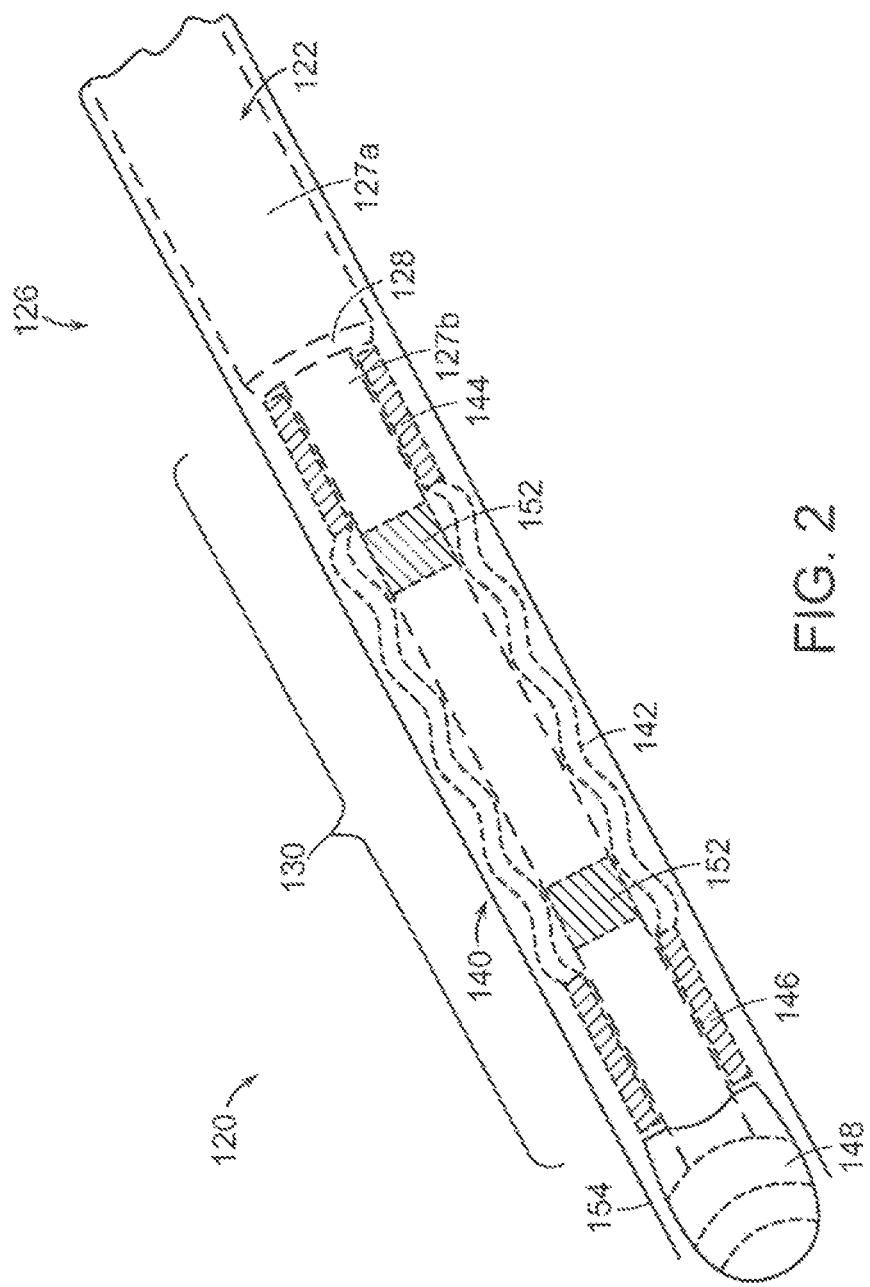
FIG. 2 is an isometric view illustrating an embodiment of a distal portion of a shaft and a cooling assembly in a delivery state (e.g., low-profile or collapsed configuration) in accordance with an embodiment of the present technology.
Figure 3:
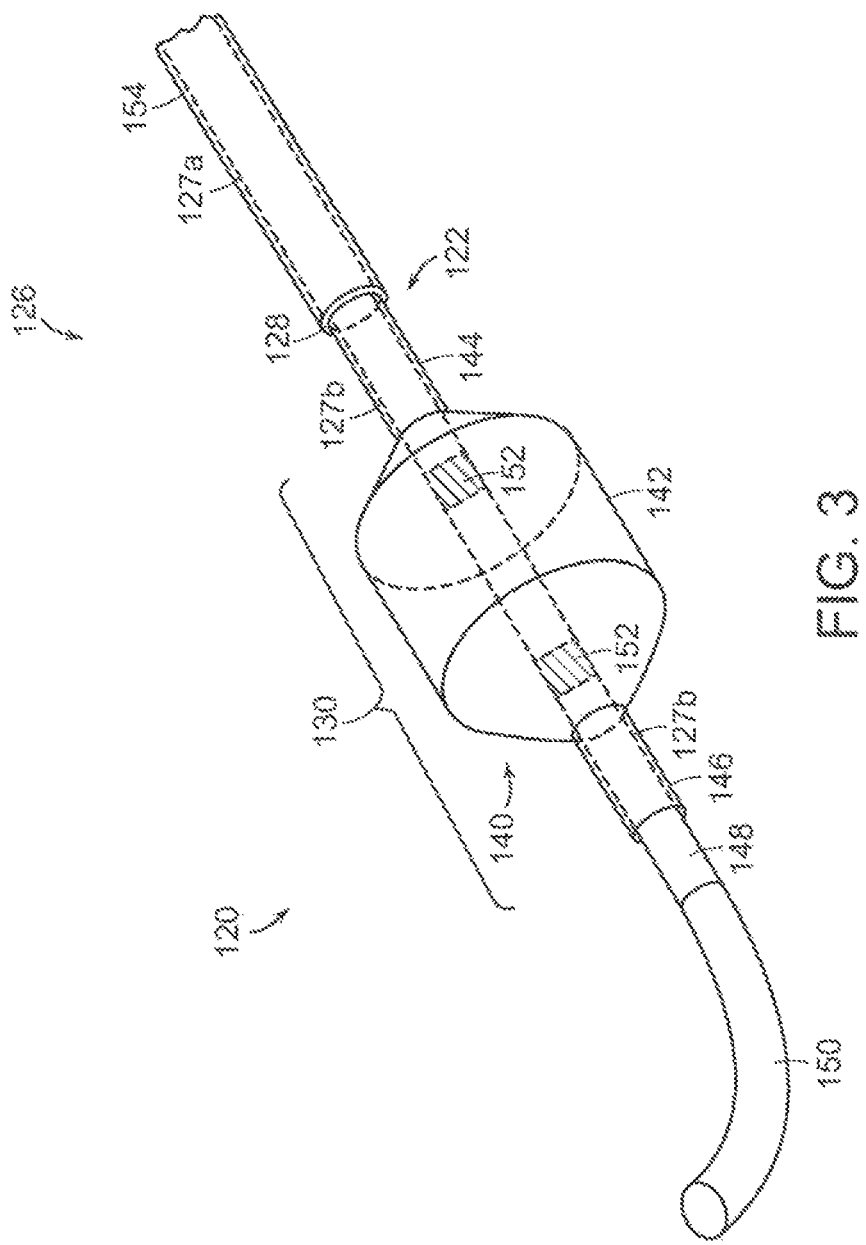
FIG. 3 is an isometric view illustrating an embodiment of a distal portion of a shaft and a cooling assembly in a deployed state (e.g., expanded configuration) in accordance with an embodiment of the present technology.

FIGS. 2-3 are isometric views illustrating embodiments of the distal portion 126 of the shaft 122 and the cooling assembly 130 in a delivery state (FIG. 2) and in a deployed state (e.g., expanded configuration, FIG. 3) in accordance with the present technology. Referring to FIGS. 2 and 3 together, the distal portion 126 of the shaft 122 can include a first zone 127a and a second zone 127b recessed inwardly relative to the first zone 127a. The first zone 127a can be demarcated from the second zone 127b by a step 128 (described in more detail below with respect to FIG. 6). The shaft 122 can be made from materials configured to provide flexibility, torqueability and pushability at one or more regions along the shaft 122. In one particular example, the shaft 122 is made from a stainless steel braid having embedded polymer (e.g., urethane) with varying durometers to alter flexibility at varying portions of the shaft 122. For a particular example, the proximal portion 124 of the shaft 122 (FIG. 1) can have a durometer of 75D, the first zone 127a of the distal portion 126 can have a durometer of 65D, and the second zone 127b can have a durometer of 55D. In another example, the shaft 122 could include an inner liner constructed, for example, with a polymer (e.g., urethane). In further embodiments, the shaft could be formed with other suitable materials, such as nylon, polyimide, braided polyimide or polyamide materials.

As shown, the cooling assembly 130 can include a cooling applicator 140 with expandable member 142 (e.g., balloon 142). The balloon 142 can have a proximal attachment region 144 attached to the second zone 127b of the distal portion 126 and a distal attachment region 146 attached to a distal connector 148. In one embodiment, the proximal attachment region 144 and distal attachment region 146 can be laser bonded to the second zone 127b, the distal connector 148 and/or other connector within the cooling assembly 130. In one embodiment the expandable member or balloon 142 can have a constant wall thickness. In other embodiments, the wall thickness can be different in different regions of the balloon 142. For example, the wall thickness at the proximal attachment region 144 and distal attachment region 146 may be greater than a wall thickness configured to contact a target site.

In one embodiment, the balloon 142 can be relatively short (e.g., 10 mm or less) to accommodate the length and tortuosity of a renal artery (e.g., between 4-6 cm) and can have a diameter in a deployed configuration large enough to contact a significant portion of the inner circumference of the renal artery (e.g., between 3-10 mm in diameter). In other embodiments (not shown), balloons can be configured to only partially occlude a renal artery or renal ostium. The balloon 142 can comprise a compliant material, a non-compliant material, and/or a combination of compliant and non-compliant materials. In various embodiments, for example, the balloon 142 can be made from polyurethane and/or other compliant or semi-compliant materials that can expand and conform to vessel walls to fully occlude vessels of varying sizes (e.g., vessels having an inner diameter from approximately 3 mm to approximately 10 mm, or in specific applications approximately 4 mm to approximately 8 mm). In other embodiments, the balloon 142 can be made from nylon and/or other non-compliant materials and sized to accommodate vessels within a certain size range. For example, a non-compliant nylon balloon can be sized to accommodate vessels having an inner diameter between approximately 3 mm and 6 mm, and a larger non-compliant nylon balloon can be sized to accommodate vessels having an inner diameter between approximately 7 mm and 10 mm.

The distal connector 148 can have a curved, bullet-like tip as shown in FIG. 2 or can be otherwise configured to provide an atraumatic tip 150 as shown in FIG. 3 that extends distally therefrom. The atraumatic tip 150 can serve as a fixed guide to facilitate navigation through the vasculature. The distal connector 148 can be attached to (e.g., by thermal bonding) or formed integrally with the atraumatic tip 150. For example, in one embodiment, the atraumatic tip 150 can have a proximal step down portion (not shown) instead of a separate distal connector 148 wherein the proximal step down portion has a diameter less than a diameter of the second zone 127b. In this embodiment, the proximal step down portion (not shown) is inserted into a distal end (not shown) of the second zone 127b and the attachment region 146 of the balloon 142 can be fixed over the distal end (not shown) of the second zone 127b.

If present, the atraumatic tip 150 can extend approximately 0.5 cm to 5 cm (e.g., approximately 1-2 cm) from the distal connector 148 and have an outer diameter between approximately 0.010 inch (0.254 mm) to approximately 0.050 inch (1.27 mm). In one embodiment, for example, the atraumatic tip 150 can have a length of approximately 2 cm and an outer diameter of at least 0.035 inch (0.889 mm; e.g., 0.038 inch (0.965 mm)). In other embodiments, the atraumatic tip 150 can have other suitable lengths and/or outer diameters. In some embodiments, the atraumatic tip 150 can be tapered having varying diameters and/or have varying cross-sectional arrangements (e.g., generally round, flat, etc.) along the length of the tip. In one arrangement, the atraumatic tip 150 can have a fixed shape that enables the atraumatic tip 150 to navigate through the vasculature to the target site by avoiding smaller arterial branches or adrenal arteries, for example. In other embodiments, the angle and/or rotational orientation of the atraumatic tip 150 can be adjusted by a control wire (e.g., a pull-wire) (not shown) that extends through at least a portion of the shaft 122. For example, a user can manipulate the control wire to deflect or otherwise move the atraumatic tip 150 to steer the distal portion 126 of the shaft 122 to the target site (i.e., avoid side branches, adrenal arteries, etc.). In other embodiments not shown, the atraumatic tip 150 can be defined by a distal end portion of a guide wire (not shown) that extends through the shaft 122 and beyond the distal connector 148.

The atraumatic tip 150 can be made from substantially smooth and flexible materials or structures such that it can gently contact and deflect off of vessel walls as the cryotherapeutic device 120 navigates the vasculature, and therefore avoids perforation and/or other trauma to the vessels through which it navigates. For example, the atraumatic tip 150 can be made from a flexible coil (e.g., a platinum coil) over a core or wire (e.g., a stainless steel wire). In other embodiments, the atraumatic tip 150 can be made from other deflectable and gentle materials and structures, such as a polymer material (e.g., Pebax® polymer, polyurethane, nylon, etc.), a polymer material over a metallic wire (e.g., a stainless steel wire), and/or other suitable materials. In one embodiment, the atraumatic tip 150 can have a polymer material over a metallic flat wire allowing the atraumatic tip to be shaped manually.

Referring to FIG. 3, the second zone 127b may be configured to extend axially through the expandable member (e.g., balloon) 142. In this embodiment, the second zone 127b can be configured to attach to the distal attachment region 146 of the balloon 142 and/or the distal connector 148 to provide additional support for and/or provide housing for additional components of the cooling assembly 130. In other embodiments, the second zone 127b or, more generally, the shaft 122, may terminate proximally to or within the balloon 142. In some embodiments, the cooling assembly 130 can include radiopaque markers 152 or markings for facilitating navigation of the cryotherapeutic device 120 through the vasculature using imaging techniques known in the art. FIG. 3 illustrates an embodiment where radiopaque markers 152 and/or radiopaque markings are applied to an outer surface at proximal and distal portions of the second zone 127b of the distal portion 126 of the shaft 122. In other embodiments, not shown, the balloon 142 can also include radiopaque markers 152 (e.g., made with radiopaque ink). In certain aspects, a portion of the atraumatic tip 150 (e.g., a coil wrapped around the core/wire) can be made from platinum and/or other radiopaque materials (e.g., platinum/iridium alloy).

With reference to FIG. 2, the shaft 122 and cooling assembly 130 can be sized to fit within a sheath 154 of 8 Fr or smaller (e.g., a 6 Fr guide sheath) to accommodate small renal arteries during delivery of the cooling assembly 130 to a treatment target site. In operation, the cooling assembly 130 is passed intravascularly to a target site in a vessel while in the delivery configuration (shown in FIG. 2). Referring to FIG. 3, the cooling assembly 130 and the sheath 154 are then moved relative to each other such that the cooling assembly 130 extends distally beyond the sheath 154 when deploying. For example, the sheath 154 can be pulled proximally and/or the cooling assembly 130 can be pushed distally (shown in FIG. 3).

Figure 4:
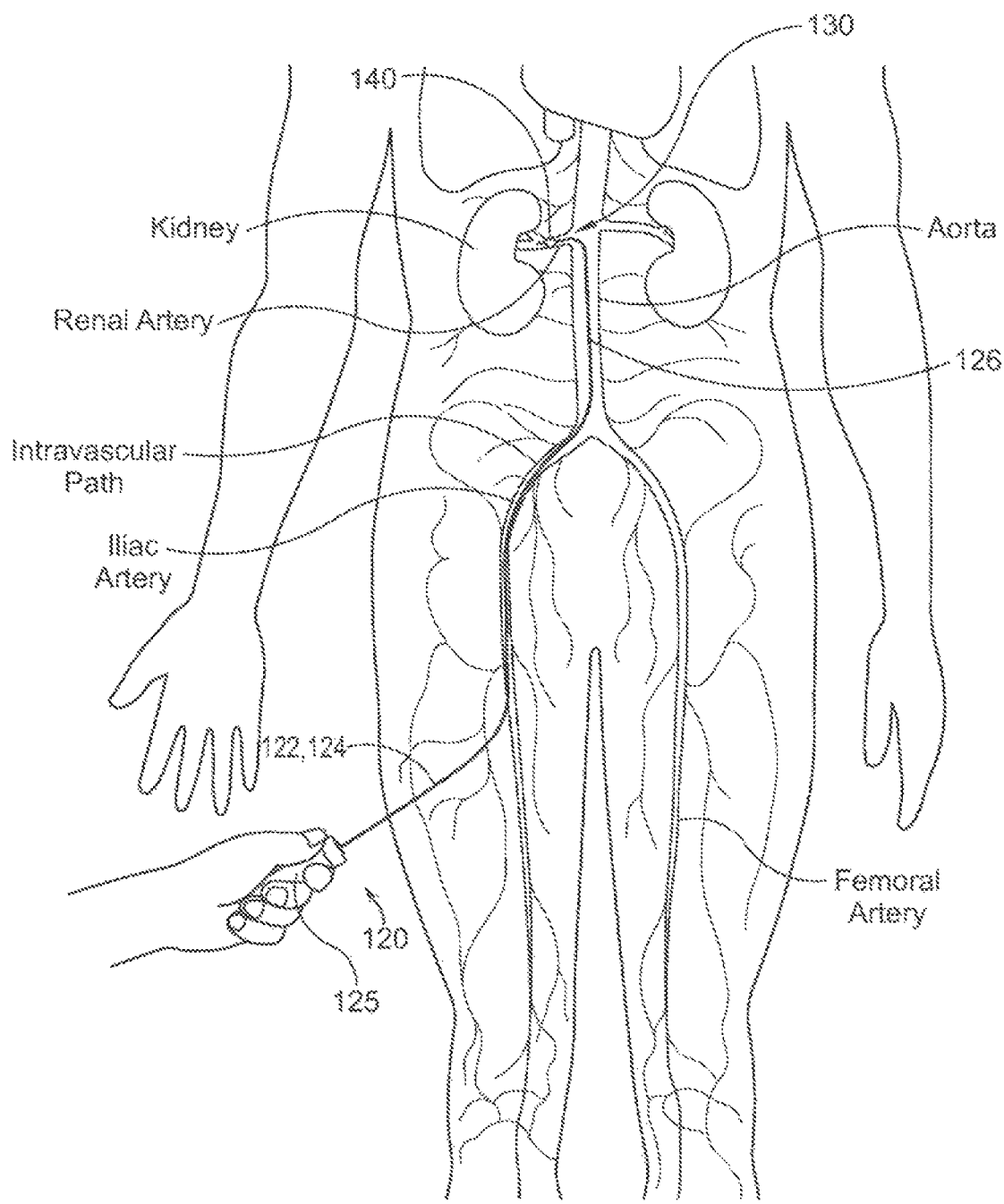
FIG. 4 illustrates cryogenically modulating renal nerves with a cryotherapeutic system in accordance with an embodiment of the technology.

FIG. 4 illustrates cryogenically modulating renal nerves with an embodiment of the system 100. The cryotherapeutic device 120 provides access to the renal plexus through an intravascular path P that leads to a respective renal artery. As illustrated, a section of the proximal portion 124 of the shaft 122 is exposed externally of the patient. By manipulating the proximal portion 124 of the shaft 122 from outside the intravascular path, the caregiver may advance the shaft 122 through the tortuous intravascular path (e.g., via the femoral artery or a radial artery) and remotely manipulate the distal portion 126 (e.g., with an actuator in the handle 125). For example, the shaft 122 may further include one or more pull-wires or other guidance devices to direct the distal portion 126 through the vasculature. Image guidance, e.g., CT, radiographic, IVUS, OCT or another suitable guidance modality, or combinations thereof, may be used to aid the medical provider's manipulation. After the cooling applicator 140 is adequately positioned in the renal artery or at the renal ostium, it can be expanded or otherwise deployed using the console 102 (FIG. 1), the handle 125 (FIG. 1), and/or another means until the applicator 140 contacts the inner wall of the renal artery. The purposeful application of cooling power from the applicator 140 is then applied to tissue to induce one or more desired neuromodulating effects on localized regions of the renal artery and adjacent regions of the renal plexus, which lay intimately within, adjacent to, or in close proximity to the adventitia of the renal artery. The purposeful application of the neuromodulating effects may achieve neuromodulation along all or a portion of the renal plexus.

The neuromodulating effects are generally a function of, at least in part, the temperature of the applicator 140, contact between the applicator 140 and vessel wall, dwell time of the applicator 140 while cooling, number of cooling cycles (e.g., one or more cooling cycles separated by a warming period), and blood flow through the vessel. Desired cooling effects may include cooling the applicator such that the temperatures of target neural fibers are below a desired threshold to achieve cryo alteration or ablation. For example, the refrigerant gas in the applicator 140 can be cooled to a temperature of about −88° C. to about −40° C., or in other embodiments the gas in the applicator 140 can have a temperature of about −80° C. to about −60° C., or from about −88° C. to about −60° C.

In various embodiments, neuromodulating effects can occur within 100 seconds (e.g., 90 seconds, 75 seconds, 60 seconds, 30 seconds, etc.) of applying the cooled applicator 140 to the renal artery or renal ostium in one or more cooling cycles. In one embodiment, the process can include two cooling cycles separated by a warming period, but in other embodiments the process can have more than two cooling cycles separated by warming periods. The cooling cycles can have the same duration or different durations, such as approximately 10 seconds to approximately 90 seconds each. The duration(s) of the warming periods can be sufficient to partially or completely thaw frozen matter at the cooling interface. In several embodiments, the duration(s) of the warming periods can be from about 5 seconds to about 90 seconds. Individual warming periods between cooling cycles may last for the same amount of time or for different amounts of time. The durations of the cooling and warming cycles can be predetermined and programmed into an algorithm, or the system can include an automatic control algorithm using a feedback loop based on the pressure and/or temperature within and/or on the external surface of the balloon. For example, the control algorithm can terminate a warming cycle and initiate a cooling cycle by assessing when the frozen matter has sufficiently thawed based on the pressure and/or temperature measurements. Depending upon the number and length of cooling cycles, the total procedure time from the deployment of the cooling assembly 130 (e.g., as shown in FIG. 3) to retraction of the cooling assembly to the delivery state (e.g., as shown in FIG. 2) can be less than five minutes (e.g., less than 3 minutes). When both renal arteries are treated, the total procedure time from the time of deployment of the cooling assembly 130 in the first renal artery, to repositioning, deployment, and retraction of the cooling assembly 130 in the second renal artery can be less than 12 minutes (e.g., 10 minutes, 6 minutes, etc.). In certain embodiments, the procedure time can be decreased by locating the applicator 140 around a full circumference of the renal artery (e.g., along the same plane or along parallel planes spaced laterally apart) and performing neuromodulation in a single application. In other embodiments, the applicator 140 can be applied to less than a full circumference of the renal artery and/or in more than one application.

Figure 5:
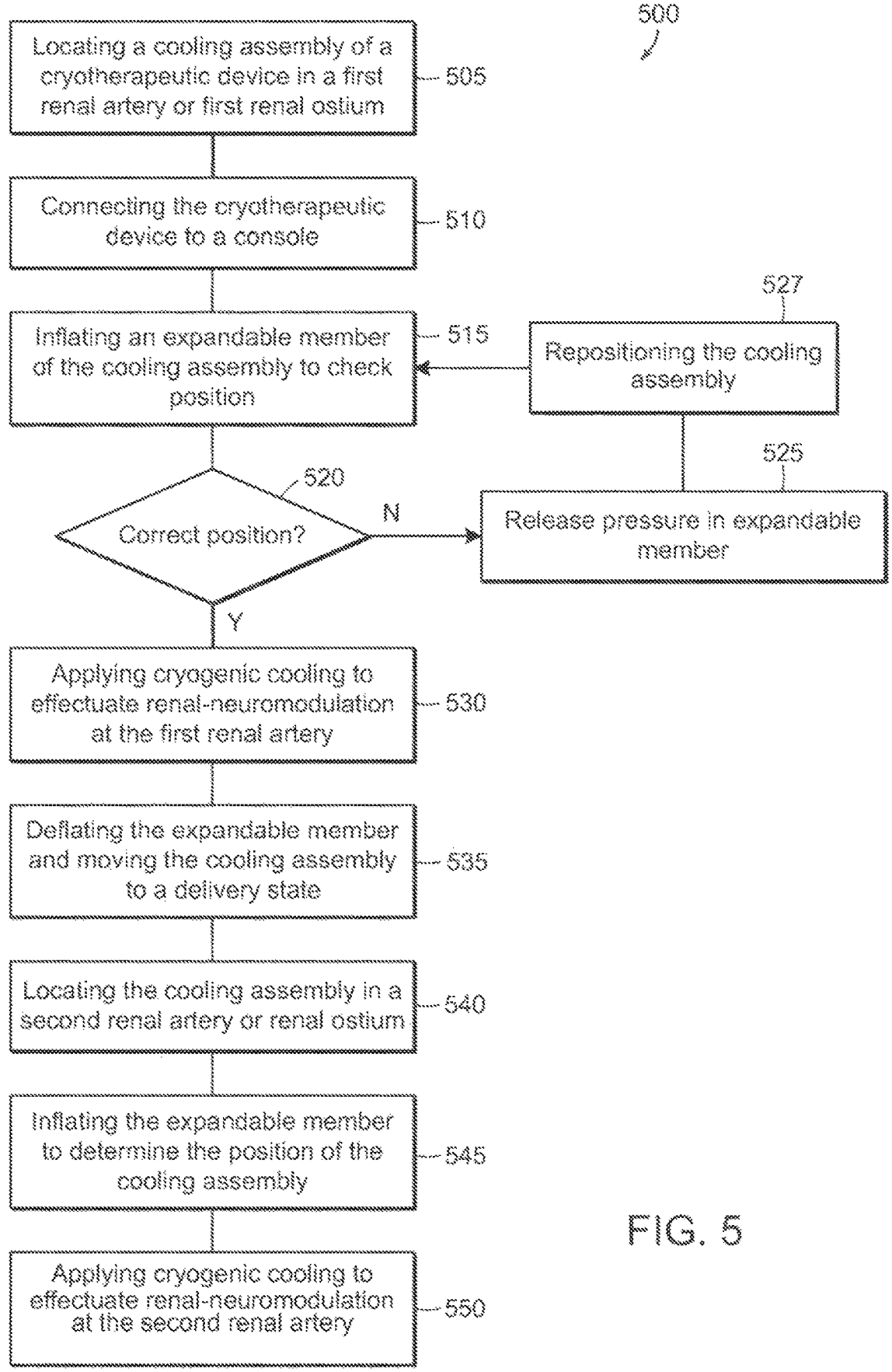
FIG. 5 is a block diagram illustrating a method of cryogenically modulating renal nerves in accordance with any embodiment of the present technology.

FIG. 5 is a block diagram illustrating a method 500 of cryogenically modulating renal nerves using the system 100 described above with reference to FIGS. 1-4. With reference to FIGS. 1-3 and FIG. 5 together, the method 500 can include intravascularly locating the cooling assembly 130 in a delivery state (e.g., as shown in FIG. 2) to a first target site in or near a first renal artery or first renal ostium (block 505). The cryotherapeutic device 120 and/or portions thereof (e.g., the cooling assembly 130) can be inserted into a guide catheter (e.g., the sheath 154 shown in FIGS. 2-3) to facilitate intravascular delivery of the cooling assembly 130. In certain embodiments, for example, the cryotherapeutic device 120 can be configured to fit within an 8 Fr guide catheter or smaller (e.g., 7 Fr, 6 Fr, etc.) to access small peripheral vessels. A guide wire (not shown) can be used to manipulate and enhance control of the shaft 122 and the cooling assembly 130 (e.g., in an over-the-wire or a rapid-exchange configuration). Radiopaque markers 152 and/or markings (shown in FIGS. 2-3) on the cryotherapeutic device 120 and/or the guide wire can facilitate placement of the cooling assembly 130 at the first target site. In some embodiments, a contrast material can be delivered distally beyond the cooling assembly 130, and fluoroscopy and/or other suitable imaging techniques can be used to aid in placement of the cooling assembly 130 at the first target site.

The method 500 can further include connecting the cryotherapeutic device 120 to the console 102 (block 510), and partially or fully inflating an expandable member of the cooling assembly 130 (e.g., the balloon 142) to determine whether the cooling assembly 130 is in the correct position at the target site and/or whether the balloon 142 has a leak (blocks 515 and 520). The balloon 142 can be inflated via the supply line 110 with refrigerant 106 from the supply container 104 at the console 102 and/or with other suitable fluids (e.g., air) from a secondary fluid supply reservoir in fluid communication the expansion chamber 143. In one example, the balloon 142 can be inflated with $N_2O$ to a pressure such as 30 or 50 psi, or in other embodiments, to a pressure of approximately 25-50 psi, to determine if there is a leak in the balloon or elsewhere within the applicator 140 or cooling assembly 130. Short bursts of applied pressure in the approximate range of 25-50 psi are insufficient to cause cooling of the applicator 140 or the surrounding tissue, however, leaks from holes, ruptures, or compromised bonds between components of the cryotherapeutic device 130 may be detected prior to applying cryotherapeutic treatment.

If the cooling assembly 130 is not in the desired location (e.g., as determined by detection of a radiopaque marker or some other visible detection marker), at least some of any remaining pressure in the balloon 142 from the leak test can be released (block 525). In certain embodiments, for example, the balloon 142 can be fully deflated by disconnecting the cryotherapeutic device 120 from the console 102 and using a syringe (not shown) to manually deflate the balloon 142 via a proximal end portion of the shaft 122. In other embodiments, the cryotherapeutic device 120 can remain attached to the console 102, and a syringe (e.g., a stopcock syringe), not shown, can be connected along the length of the shaft 122 to deflate the balloon 142. In further embodiments, the controller 118 at the console 102 can include algorithms for partially or fully deflating the balloon 142. Following the release of pressure in the balloon 142, a further step can include repositioning the cooling assembly (block 527) before optionally repeating the inflation step (block 515) and position determining step (block 520).

Once the cooling assembly 130 is properly located at the first target site and no leaks are detected, the console 102 can be manipulated to initiate cooling of the cooling assembly 130 and modulation of renal nerves at the first target site to cause partial or full denervation of the kidney associated with the first target site (block 530).

Cryogenic cooling can be applied for one or more cycles (e.g., for 30 second increments, 60 second increments, 90 second increments, etc.) in one or more locations along the circumference and/or length of the first renal artery or first renal ostium. The cooling cycles can be, for example, fixed periods or can be fully or partially dependent on detected temperatures (e.g., temperatures detected by a thermocouple (not shown) of the cooling assembly 130). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

In one particular embodiment, for example, two 90 second cycles may be used with a partial or complete thaw between the cryogenic cooling cycles. In such an example, the balloon 142 can be inflated with $N_2O$ to a pressure of 25 psi for 90 seconds. Following the first 90 second treatment, and in one embodiment, the $N_2O$ supply can be turned off or diminished and the balloon 142 can completely or partially deflate. The pump 111 (FIG. 1) may or may not be used to deflate the balloon 142 or otherwise assist in removing exhausted refrigerant 117. Prior to the second cooling cycle in this example, a second leak test may be performed and a warming period can be employed where blood flow warms an outside surface of the balloon 142 or applicator 140 to remove or prevent cryoadhesion between the outside surface of the balloon 142 and tissue at the target site. In other embodiments, the balloon 142 can remain fully or partially inflated to maintain the position of the cooling assembly 130 at the target site between cooling cycles. In other treatment scenarios, a single cooling cycle could be employed in which a second leak test and/or position confirmation would be unnecessary.

After renal-neuromodulation at the first renal artery or first target site, the method 300 can further include deflating the balloon 142 and retracting the cooling assembly 130 into the delivery state (block 535). The balloon 142 can be deflated manually by detaching the cryotherapeutic device 120 from the console 102 and connecting a syringe (not shown) or other suitable evacuation device to the proximal end of the shaft 122. In other embodiments, a syringe (not shown) can be connected along the length of the shaft 122 without detaching the cryotherapeutic device 120 from the console 102, or the balloon 142 can be deflated automatically (e.g., via the controller 118). In certain embodiments, the cooling assembly 130 can be withdrawn back into the guide catheter (e.g., the sheath 154) after the balloon 142 is deflated. Optionally, the cooling assembly 130 can be removed from the guide catheter during repositioning and temporarily stored in a sterile location outside of the body of the patient (e.g., in a saline solution).

The cooling assembly 130 can then be located at a second target site in or near a second renal artery or second renal ostium (block 540), and the balloon 142 can be expanded to confirm the position of the cooling assembly 130 (block 545). In selected embodiments, a contrast material can be delivered distally beyond the cooling assembly 130 and fluoroscopy and/or other suitable imaging techniques can be used to locate the second renal artery. If necessary, the used supply container 104 in the console 102 can be refilled or removed and replaced with a new supply container (e.g., a disposable refrigerant cartridge) to provide sufficient refrigerant for renal-neuromodulation at the second target site. In embodiments where the console 102 was detached from the cryotherapeutic device 120 during repositioning of the cooling assembly 130, the console 102 can be reconnected to the cryotherapeutic device 120 such that the method 500 continues by applying cryogenic cooling to effectuate renal-neuromodulation at the second target site to cause partial or full denervation of the kidney associated with the second target site (block 550).

In other embodiments, various steps in the method 500 can be modified, omitted, and/or additional steps may be added. For example, the console 102 can be turned on and loaded with the supply container 104 outside the sterile field in which the cryotherapy occurs, and positioned in a sterile bag or housing such that it can be brought into the sterile field. If the supply container 104 must be reloaded or refilled during cryotherapy, the console 102 can be removed from the sterile field, reloaded, and placed back into the sterile field (e.g., in a sterile bag or housing). In other embodiments, the empty supply container 104 can be removed from the console 102 and deposited within a sterile bag or housing surrounding the console 102, and a new supply container can be attached to the console 102 within the sterile bag or housing such that the console 102 does not leave the sterile field during a treatment procedure. In further embodiments, the console 102 can remain outside the sterile field and operated remotely. In another embodiment, the method 500 can have a delay between applying cryogenic cooling to a first target site at or near a first renal artery or first renal ostium and applying cryogenic cooling a second target site at or near a second renal artery or second renal ostium. For example, cryogenic neuromodulation of the first renal artery can take place at a first treatment session, and cryogenic neuromodulation of the second renal artery can take place a second treatment session at a later time.

Additional Embodiments of Cryotherapeutic Devices

Figure 6:
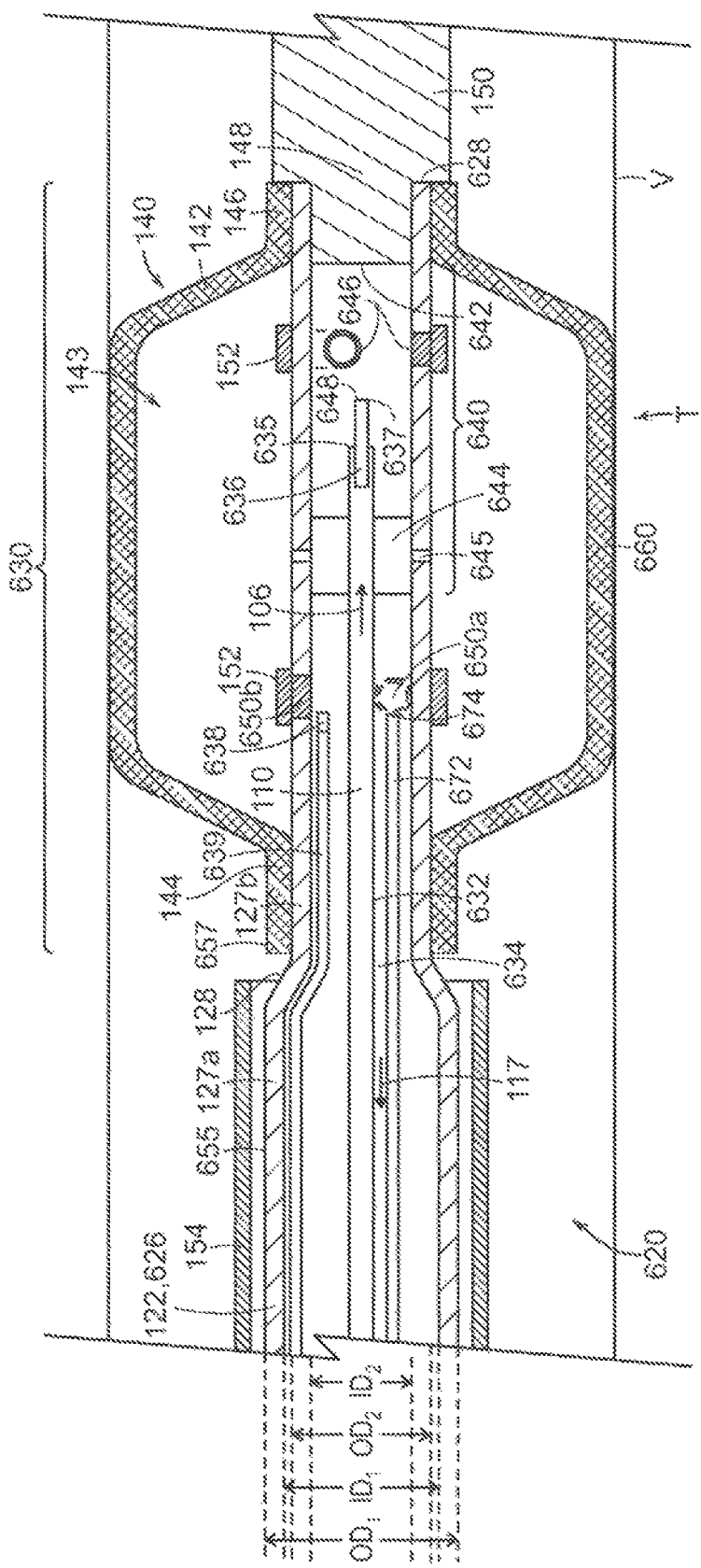
FIG. 6 is an enlarged cross-sectional view of a cryotherapeutic device having a distributor configured in accordance with another embodiment of the present technology.

FIG. 6 is an enlarged cross-sectional view of a distal portion 626 of a cryotherapeutic device 620 configured in accordance with an embodiment of the present technology. The cryotherapeutic device 620 includes features generally similar to the features of the cryotherapeutic device 120 described above with reference to FIGS. 1-3. For example, the cryotherapeutic device 620 includes the elongated shaft 122 and a cooling assembly 630 at the distal portion 626 of the shaft 122. The cooling assembly 630, shown here in a deployed state (e.g., expanded configuration), includes the applicator 140 having an expandable member, such as the balloon 142 or other suitable expandable member, that defines at least a portion of the expansion chamber 143 and receives the refrigerant 106 in a liquid, gas and/or liquid/gas mixture via the supply line 110. In the deployed state, the balloon 142 can be configured to fully occlude a renal artery or renal ostium.

The cryotherapeutic device 620 can also include a supply tube or lumen 632 and an exhaust passage or lumen 634 along at least a portion of the shaft 122. The supply lumen 632 can be a small tube configured to retain the refrigerant in a liquid state at a high pressure. The inner diameter of the supply lumen 632 is selected such that at least a portion of the refrigerant reaching the cooling assembly 630 is in a liquid state at a distal terminal opening 635 of the supply lumen 632. In one embodiment, the terminal opening 635 can have a diameter less than that of the supply lumen 632 to impede the flow of the refrigerant 106 into the cooling assembly 630, thereby increasing the pressure drop of the refrigerant 106 entering the expansion chamber 143 and concentrating the refrigeration power at the cooling assembly 630. In other embodiments, the supply lumen 632 may have a substantially constant inner diameter (e.g., 0.008 inch (0.203 mm), 0.009 inch (0.023 mm), 0.010 inch (0.254 mm), etc.) such that the terminal opening 635 has a diameter at least equal to that of the supply lumen 632. In some embodiments, the supply lumen 632 can be made from stainless steel, and in other embodiments, the supply lumen can be made from polyimide and/or one or more other polymers. In some arrangements, the supply lumen 632 can provide structural functionality to at least a portion of the shaft 122 such as pushability, and/or protect the shaft 122 from excessive bending (e.g., kinking) inside the vasculature during delivery or deployment of the cooling assembly 630.

The cooling assembly 630 can also include a capillary tube 636 positioned and/or inserted into the terminal opening 635 of the supply lumen 632. The capillary tube 636 and/or a distal tube end 637 of the capillary tube 636 can have a diameter less than that of the supply lumen 632 and/or the terminal opening 635 to impede the flow of refrigerant 106. The flow rate of the refrigerant 106 can also be manipulated by changing the lengths of the supply lumen 632 and the capillary tube 636 relative to one another. For example, in certain embodiments, the capillary tube 636 can be at most ⅓ the length of the supply lumen 632. In various embodiments, the capillary tube 636 can have a length between 2 inches (5.08 cm) and 30 inches (76.2 cm) and the supply lumen 632 can be sized accordingly. In other embodiments, the capillary tube 636 can be shorter or longer relative to the supply lumen 632 and/or the capillary tube 636 can be omitted.

The exhaust lumen 634 can provide an exhaust passage or path, and the supply lumen 632 can extend within the exhaust lumen 634 along at least the distal portion 626 of the shaft 122. As described in further detail below, several embodiments of the cryotherapeutic device 120 can further include one or more sensors, such as a temperature sensor 638 (e.g., thermocouple), coupled to the controller 118 (FIG. 1) by a lead 639. In several embodiments, the cryotherapeutic system 100 can be configured to verify the proper calibration of the temperature sensor 638 before a cryotherapeutic treatment. For example, the cryotherapeutic system 100 can automatically compare a measured temperature from a temperature sensor with room temperature as the cryotherapeutic system 100 initiates a power up cycle to check that the temperature sensor is functioning properly.

As shown in FIG. 6, the cryotherapeutic device 620 can further include a pressure monitoring lumen 672 coupled to the pressure sensor 105 (FIG. 1) via the pressure line 107 (FIG. 1). The pressure monitoring lumen 672 can extend through the shaft 122 and have a distal opening 674 in fluid communication with the expansion chamber 143 (e.g., defined by the balloon 142). The dimensions (e.g., cross-sectional area, inner diameter, and/or outer diameter) of the pressure monitoring lumen 672 can be large enough to sense a pressure reading within the expansion chamber 143 with substantial accuracy and response time, but small enough to reduce or prevent interference with the outflow of exhausted refrigerant 117 through the exhaust lumen 634. For example, the supply lumen 632 and the pressure monitoring lumen 672 together can have a first cross-sectional dimension (e.g., a first cross-sectional area) and the exhaust lumen 634 can have a second cross-sectional dimension (e.g., a second cross-sectional area) such that the ratio of the second cross-sectional dimension to the first cross-sectional dimension is between 4:1 and 10:1. In certain embodiments, the pressure monitoring lumen 672 can have an inner diameter of no more than 0.03 inch (0.762 mm; e.g., 0.015 inch (0.381 mm), 0.010 inch (0.762 mm), etc.) and an outer diameter of no more than 0.060 inch (1.52 mm; e.g., 0.02 inch (0.508 mm), 0.015 inch (0.381 mm), etc.), and the exhaust lumen 634 can be sized accordingly.

The pressure monitoring lumen 672, in the illustrated embodiment, has a length sufficient to intravascularly locate the opening 674 along with the cooling assembly 630 at the target site T (e.g., a renal artery or renal ostium via a femoral artery or a radial artery). For example, the pressure monitoring lumen 672 can have a length equivalent to the full length of the shaft 122 (e.g., at least 48 inches (122 cm)). In other embodiments, the pressure monitoring lumen 672 can have other suitable lengths and/or dimensions. In some embodiments, the pressure monitoring lumen 672 can be made from stainless steel, and in such arrangements, may be able provide structural functionality to at least a portion of the shaft 122. For example, if the shaft is formed of polyimide and/or one or more other polymers, a stainless steel pressure monitoring lumen can provide mechanical strength to the cryotherapeutic device 620 while moving the cooling assembly 630 through the vasculature.

In the embodiment shown in FIG. 6, the distal portion 626 of the shaft 122 can include the first zone 127a and the second zone 127b recessed inwardly relative to the first zone 127a at the step 128. In the illustrated embodiment, the second zone 127b extends axially through the expansion chamber 143 of the balloon 142 to the distal connector 148 and/or the atraumatic tip 150. In one embodiment, the proximal attachment region 144 and the distal attachment region 146 of the balloon 142 attach to the distal portion 626 of the shaft 122 at proximal and distal regions of the second zone 127b, respectively. The distal portion 626 and the attachment regions 144, 146 of the balloon 142 can be attached together using adhesives (e.g., thermal bonds), fasteners, and/or other suitable attachment mechanisms known in the art. In other arrangements not shown, the cooling assembly 630 can include proximal and distal intermediate connectors (e.g., collars, or other suitable retainers, not shown) to which proximal and distal portions of the balloon 142, respectively, may be attached. The intermediate connectors may be attached over the distal portion 626 of the shaft 122, thereby coupling the balloon 142 to the shaft 122. The intermediate connectors can be attached to the distal portion 626 of the shaft 122 using thermal bonds, adhesives, interlocking surfaces (e.g., threads), friction fit, snap fit, suction, and/or other suitable attachment mechanisms, or the intermediate connectors can be formed integrally with the distal portion 626.

The first zone 127a of the distal portion 626 can have a first outer cross-sectional dimension or diameter $OD_1$ and the second zone 127b distal to the step 128 can have a second outer cross-sectional dimension or diameter $OD_2$ less than the first outer cross-sectional dimension $OD_1$. The reduction in the outer dimension of the distal portion 626 at the step 128 forms an inward recess relative to the first zone 127a in which at least a portion of the proximal attachment region 144 can sit, thereby reducing the profile of the distal portion 626 of the shaft 122. In certain embodiments, the step 128 can be dimensioned such that an outer surface 655 of the first zone 127a is at least substantially flush with an outer surface 657 of the proximal attachment region 144. FIG. 6 illustrates an embodiment of the distal portion 626 where the first zone 127a and the second zone 127b are continuous. A continuous distal portion 626 having the step 128 can be formed with a mandrel having a portion with larger diameter (e.g., for forming the first zone 127a) and a second portion with smaller diameter (e.g., for forming the second zone 127b). One of ordinary skill will recognize other methods known in the art for forming a continuous distal portion 626 having varying diameters along the length of the distal portion 626. In another embodiment, not shown, the first zone could be a separate shaft portion from the second zone. In these arrangements, not shown, the first zone can be demarcated from the second zone by a step, such as a rabbet (e.g., an annular or other circumferential groove configured to be fitted with another member). The first zone can accordingly have a first outer dimension or first cross-sectional dimension (e.g., area or diameter), and the second zone can have a second outer dimension or second cross-sectional dimension less than the first dimension.

FIG. 6 also illustrates that the cross-sectional area of the exhaust lumen 634 (e.g., defined by the inner surface(s) of the shaft 122) decreases at the transition between the first zone 127a and the second zone 127b such that the distal portion 626 of the shaft 122 has a first inner cross-sectional dimension or diameter $ID_1$ at the first zone 127a and a lesser second inner cross-sectional dimension or diameter $ID_2$ at the second zone 127b. To avoid a build up of pressure in the expansion chamber 143 that may be caused by insufficient venting through the necked-down exhaust lumen 634, the second zone 127b can be positioned only at the distal-most end of the shaft 122 proximate the expansion chamber 143 where the density of the exhausted refrigerant 117 is the highest. Venting of the exhausted refrigerant 117 can also be adequate through the smaller inner diameter $ID_2$ of the second zone 127b without being jeopardized because the length of the exhausting path provided within the second zone 127b along the longitudinal axis of the shaft 122 can be relatively short. Accordingly, the smaller exhaust lumen 134 at the second zone 127b can transport primarily high density exhausted refrigerant 117 and can expel the exhausted refrigerant 117 into the larger exhaust lumen 134 at the first zone 127a as the exhausted refrigerant 117 decreases in density, thereby facilitating adequate venting through the smaller second inner diameter $ID_2$ of the second zone 127b. In other embodiments, the distal portion 626 of the shaft 122 does not include the stepped-down exhaust lumen 634 shown in FIG. 6 and, instead, may have a substantially uniform cross-sectional dimension. Such an exhaust lumen may relatively easily accommodate a guide wire lumen (e.g., not shown) through which a guide wire can be extended to locate the cooling assembly 630 at the target site T in the vessel V.

As shown in FIG. 6, the cooling assembly 630 can also include a distributor 640 positioned distally along the distal portion 626 of the shaft 122 near a shaft terminus 628 and configured to distribute refrigerant 106 from the supply lumen 632 to the expansion chamber 143. The distributor 640 can be formed or have a wall defined by a segment of the distal portion 626 of the shaft 122. The distributor 640 can include, for example, a distal seal 642 at or near the shaft terminus 628, an intermediate seal 644 (e.g., an intermediate plug), and a plurality of first orifices 646 (e.g., holes) positioned between the distal seal 642 and the intermediate seal 644. The first orifices 646 can be radially spaced apart from one another around the circumference of the shaft 122. The supply lumen 632 and/or the capillary tube 636 extends beyond or through the intermediate seal 644 such that the distributor 640 is in fluid communication with the terminal opening 635 of the supply lumen 632 and/or the distal tube end 637 of the capillary tube 636 such that refrigerant 106 can flow out of an inflow opening 648 into the distributor 640. Operatively, refrigerant 106 can flow from the inflow opening 648 into the distributor 640 and through the first orifices 646 in a radial pattern into the expansion chamber 143 of the balloon 142.

The second zone 127b can also include a plurality of second orifices 650 (e.g., holes) positioned proximate to the distributor 640 and the intermediate seal 644, such that the second orifices 650 are in fluid communication with the expansion chamber 143 and the exhaust lumen 634, thereby providing an exhaust path from the expansion chamber 143 to the proximal portion 124 (FIG. 1) of the shaft 122. The plurality of second orifices 650 can be radially spaced apart from one another around the circumference of the shaft 122. Further, the plurality of exhaust openings (e.g., second orifices 650) can promote exhaust flow and mitigate any flow restriction associated with the sizing of the distal portion 626. Thus, as discussed above, the relatively high density of expanded refrigerant entering the exhaust passage can allow the distal portion 626 to be sized down without necessarily causing an unsuitable increase in back pressure.

In one embodiment, the spacing between each of the individual first orifices 646 with respect to the other first orifices 646, can be equal. For example, the distributor 640 can include 3 first orifices 646 distributed radially around the circumference of the shaft 122, each first orifice 646 separated from neighboring orifices by 120°. In other embodiments, the spacing between each of the individual first orifices 646 with respect to the other first orifices 646 can vary or be unequal. Similarly, the spacing between each of the individual second orifices 650 with respect to the other second orifices 650, can be equal (e.g., each spacing being 180°, 120°, 90°, etc.) or the spacing can be unequal. While the embodiment shown in FIG. 6 and described above shows a plurality of first orifices 646 and a plurality of second orifices 650, one of ordinary skill in the art will recognize that the distributor 640 can be configured with a single first orifice 646 in the distal portion 626, and the exhaust path can be configured with a single second orifice 650 in the distal portion 626 proximate the first orifice 646. In some embodiments, the plurality of first orifices 646 can be radially off-set from the radially-spaced positions of the plurality of second orifices 650. The degree of off-set can be, for example, 60°. In other embodiments, the degree of off-set can be 90°, 45°, and 30°.

The first orifices 646 (e.g., inflow orifices) can be sized relative to the area and/or length of the exhaust lumen 634 at the distal portion 626 of the shaft 122 to provide a sufficient flow rate of refrigerant 106, produce a sufficient pressure drop in the expansion chamber 143, and allow for sufficient venting of the exhausted refrigerant 117 through the second orifices 650 (e.g., exhaust orifices). In one embodiment, the first orifices 646 can have a diameter of approximately 0.003 inch (0.076 mm) or more, such as about 0.004 inch (0.101 mm) to about 0.009 inch (0.229 mm). In various embodiments, the inner diameter and/or total cross-sectional area of the second orifices 650 and/or exhaust lumen 636 and the diameter and/or total cross-sectional area of the first orifices 646 can have a ratio between approximately 4:1 and 10:1. In one example, the exhaust lumen 636 can have an inner diameter between approximately 0.030 inch (0.762 mm) and approximately 0.050 inch (1.27 mm), and the first orifices 646 can have a diameter of approximately 0.003 inch (0.0762 mm) to approximately 0.008 inch (0.203 mm; e.g., 0.004 inch (0.101 mm)). In other embodiments, the second orifices 650, exhaust lumen 634 and the first orifices 646 can have other suitable dimensions. In further embodiments, the inflow opening 648 provided by the terminal opening 635 of the supply lumen 632 or the distal tube end 637 of the capillary tube 636, if present, can be sized to provide a sufficient flow rate of refrigerant 106. In these embodiments, the first orifices 646 may not need to be sized to control a flow rate of the refrigerant 106, but may provide directionality to the inflow of refrigerant 106 from the distributor 640 to the expansion chamber 143.

As shown in FIG. 6, the distal opening 674 of the pressure monitoring lumen 672 can be cross-sectionally aligned or positioned proximate (e.g., near) to a second orifice 650a such that the pressure monitoring lumen 672 is in fluid communication with the expansion chamber 143 through the opening created by the second orifice 650a. Likewise, the temperature sensor 638 (e.g., a thermocouple) can be cross-sectionally aligned or positioned proximate (e.g., near) to a second orifice 650b such that the temperature sensor is in fluid communication with the expansion chamber 143 through the opening created by the second orifice 650b. In one embodiment, second orifices 650a and 650b can be different second orifices. In another embodiment, the distal opening 674 and the temperature sensor 638 can be cross-sectionally aligned and or proximate (e.g., near) to the same second orifice 650.

The distal seal 642 located at the shaft terminus 628 can be provided by the distal connector 148 as shown in FIG. 6. For example, the distal connector 148 can be made of a suitable material (e.g., polyurethane, nylon, or stainless steel, alone or in combination) and attached to the shaft terminus 628 such that refrigerant 106 is prevented from flowing out through the shaft terminus 628. In another embodiment, the distal seal 642 can be a sealing member (not shown) or material separate from the distal connector 148. For example, a membrane, foam, plug, or other suitable sealing barrier such as those made with a polymer material (e.g., urethane) or metallic material (e.g., stainless steel) may be adhered to the shaft terminus 628 or to another position intermediate the shaft terminus 628 and the first orifices 646 to provide the distal seal 642.

The intermediate seal 644 can include a plug, for example, formed by injecting a polymer (e.g., urethane) into small injection holes 645 located longitudinally along the side of the shaft 122 at a desirable location between the first and second orifices 646, 650. The injectable material can be injected into the shaft 122 and around an outer surface of the supply lumen 632 (or capillary tube 636) such that when the material cures or otherwise adheres to the inner surface of the shaft 122 and the outer surface of the supply lumen 632 (or capillary tube 636), the inflowing refrigerant 106 cannot mix with exhausted refrigerant 117 in the shaft 122, or the intermediate seal 644 otherwise prevents back-flow of inflowing refrigerant 106. One of ordinary skill in the art will recognize other suitable sealing barriers or partitions for creating an intermediate seal 644 between the first and second orifices 646, 650. For example, a preformed plug can be positioned within the shaft 122 and around the supply lumen 632 and/or capillary tube 636 during manufacturing of the cooling assembly 630.

Optionally, the cooling assembly 630 can be configured with reinforcement structures to prevent unwanted bending or kinking of the assembly in the deployed state, for example. In accordance with one embodiment of the present technology, portions of the shaft 122 (e.g., the distal portion 626) can be configured with shaft supports. In the example illustrated in FIG. 6, radiopaque markers 152 are applied to portions of the shaft 122 that are cross-sectionally aligned with the first and second orifices 646, 650 such that the orifices 646, 650 extend through the radiopaque material. The radiopaque markers 152 made with platinum/iridium alloy, for example, can be fixed to or applied to the outside surface of the shaft 122 providing additional support in these regions of the cooling assembly 630. In one embodiment the shaft support (e.g., radiopaque markers 152) can be positioned circumferentially around the shaft 122 in a plane perpendicular to the shaft 122 and circumjacent to at least one of the first orifices 646 and second orifices 650. Other suitable reinforcement materials or structures known in the art can be applied or fastened in desirable locations along the shaft 122 to provide additional support during deployment of the cooling assembly 630. For example, an open pitch coil support (not shown) can wrap around at least a segment of the shaft at the distal portion 626, wherein the coil does not interfere with or does not otherwise occlude an undesirable area of the first and second orifices 646, 650. For example, the open pitch coil can be a round or flattened wire having a diameter less than a first or second orifice diameter.

In operation, the refrigerant 106 passes through the supply lumen 632, through the inflow opening 648 into the distributor 640, and into the expansion chamber 143 defined by the balloon 142 via the plurality of first orifices 646. As the refrigerant 106 passes through the inflow opening 648 and first orifices 646, at least a portion of it expands into a gaseous phase, thereby at least partially inflating the balloon 142 and causing a significant temperature drop in the expansion chamber 143. The portion of the applicator 140 contacting the tissue at the target T can be a heat-transfer region 660 or heat-transfer zone that, together with the refrigerant 106 in the expansion chamber 143, causes therapeutically-effective, cryogenic renal-nerve modulation. Exhausted refrigerant 117 passes in a proximal direction through the plurality of second orifices 650 into the exhaust passage defined by the exhaust lumen 634. In various embodiments, the length of shaft 122 can be minimized to decrease the losses (e.g., friction losses) of the refrigerant 106 flowing through the supply lumen 632 and through the exhaust lumen 634, thereby enhancing the refrigeration potential and the efficiency of the cooling assembly 630. Accordingly, the shaft 122 can be configured to have a total overall length of less than 90 cm (e.g., 80 cm to 85 cm, 70 cm to 80 cm, etc.). In other embodiments, the shaft 122 can be longer and/or include additional features to enhance the refrigeration power at the cooling assembly 630.

The embodiment of the cooling assembly 630 illustrated in FIG. 6 fully occludes the vessel V and produces a full-circumferential treatment at the target site T (i.e., a continuous cooled region extending completely around the inner circumference of the vessel V in a plane that is perpendicular or otherwise transverse relative to a longitudinal direction of the vessel V at the target T). Fully occluding the vessel V limits blood flow from heating the heat-transfer region 660 such that the cooling power of the refrigerant can be more efficiently applied to the target T. Although occlusion of the renal blood vessel for an excessive period of time can potentially cause ischemia of a kidney, it has been found that renal blood flow can be fully occluded for a period of time sufficient to complete cryotherapy at the target T (e.g., 1-5 minutes, or longer in some embodiments).

Figure 7A:
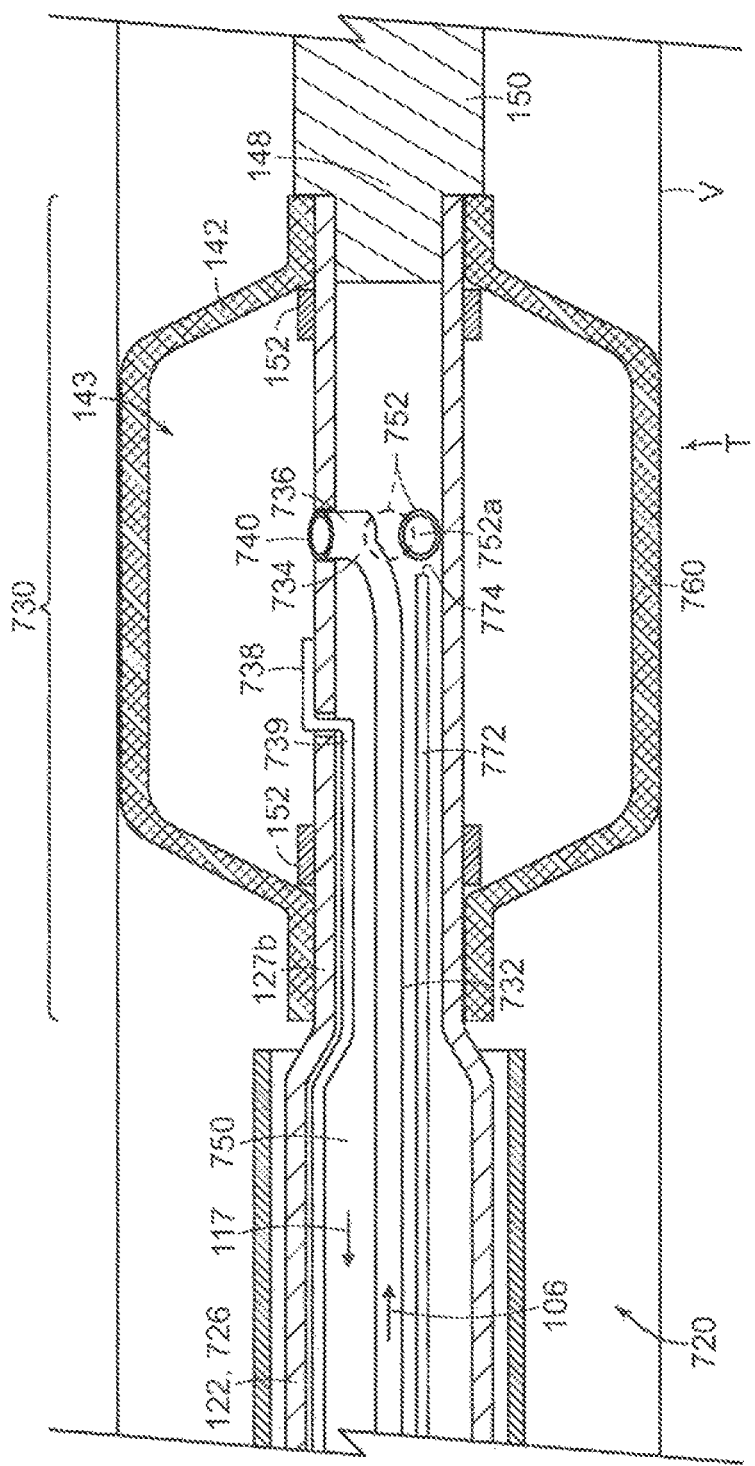
FIG. 7A is an enlarged cross-sectional view of a distal portion of a shaft and a cooling assembly in a deployed state in accordance with an embodiment of the present technology.

FIGS. 7A-7B illustrate a distal portion 726 of cryotherapeutic device 720 configured in accordance with additional embodiments of the present technology. FIG. 7A is an enlarged cross-sectional view and FIG. 7B is an enlarged side view of a distal portion 726 of a cryotherapeutic device 720 that includes features generally similar to the features of the cryotherapeutic device 620 described above with reference to FIG. 6. For example, the second zone 127b of the distal portion 726 of the shaft 122 extends axially through the expansion chamber 143 of the balloon 142 to the distal connector 148 and/or the atraumatic tip 150. However, in the embodiment shown in FIG. 7A, the second zone 127b does not include a distributor 640 (FIG. 6) having the intermediate seal 644 (FIG. 6) separating an inflow orifice 740 from one or more exhaust orifices 752 positioned along the shaft 122 and in fluid communication with the expansion chamber 143.

In the embodiment illustrated in FIG. 7A, a supply lumen 732 transports refrigerant 106 along the shaft 122 to the distal portion 726. The supply lumen 732 can have an angled portion 734 such that a distal end 736 of the supply lumen 732 can meet or otherwise connect to the inflow orifice 740. In one embodiment, the inflow orifice 740 can have a diameter less than that of the supply lumen 732 to impede the flow of the refrigerant 106 into the cooling assembly 730, thereby increasing the pressure drop of the refrigerant 106 entering the expansion chamber 143 and concentrating the refrigeration power at the cooling assembly 730. In other embodiments, the angled portion 734 and/or the distal end 736 of the supply lumen 732 can have one or more diameters less than the diameter of the supply lumen 732 to increase the pressure drop of the inflowing refrigerant 106. In another embodiment, the supply lumen 732 may have a substantially constant inner diameter (e.g., 0.005 inch (0.127 mm) to 0.009 inch (0.229 mm), etc.) such that the distal end 736 has a diameter at least equal to that of the supply lumen 732.

The cooling assembly 730 also includes an exhaust passage 750 extending from the one or more exhaust orifices 752 along at least a portion of the shaft 122 from the distal portion 726 to the proximal portion 124 (FIG. 1). The exhaust orifices 752 are sized to allow for adequate venting of the refrigerant 106 from the expansion chamber 143 into the exhaust passage 750. In one embodiment, the inflow orifice 740 and the one or more exhaust orifices 752 can be cross-sectionally and radially aligned around the circumference of the second zone 127b of the distal portion 726, as illustrated in FIGS. 7A and 7B. In other arrangements, however, the inflow orifice 740 and the exhaust orifices 752 can be proximally or distally arranged with respect to each other orifice 740, 752 along the shaft at the second zone 127b. In one embodiment, the distal portion 726 can include a single exhaust orifice 752. In other embodiments, the distal portion 726 can include two or more exhaust orifices 752 spaced apart from each other and radially distributed around the circumference of the shaft 122. The spacing between each of the individual exhaust orifices 752 with respect to the other exhaust orifices 752, can be equal (e.g., each spacing being 180°, 120°, 90°, etc.) or the spacing can be unequal.

The cryotherapeutic device 720 can also include a pressure monitoring lumen 772 extending along at least a portion of the shaft 122 to the distal portion 726. The pressure monitoring lumen 772 can have a distal opening 774 in fluid communication with the expansion chamber 143 and/or the exhausted refrigerant 117, wherein the distal opening 774 is proximal (e.g., near) to the exhaust orifice 752a. In one embodiment, the distal opening 774 can be cross-sectionally aligned with the exhaust orifice 752a.

In certain embodiments, the cryotherapeutic device 720 can include a temperature sensor, such as a thermocouple 738, located within the distal portion 726 of the shaft 122 (e.g., adjacent to the exhaust orifice 752), or alternatively, and as shown in FIGS. 7A and 7B, located outside the shaft 122 and within the expansion chamber 143. In one embodiment, and as shown in FIG. 7A, a thermocouple lead 739 can transect a wall of the shaft 122 such that the temperature sensing portion of the thermocouple 738 can be positioned outside of the distal portion 726 of the shaft 122 and within the expansion chamber 143 of the balloon 142. In another embodiment illustrated in the enlarged side view of the distal portion 726 shown in FIG. 7B, the lead 739 can cross the wall of the shaft 122 via an exhaust orifice 752b.

Optionally, the cooling assembly 730 can be configured with reinforcement structures to prevent unwanted bending or kinking of the assembly 730 in the deployed state, for example. In one embodiment, a radiopaque marker 152 can be placed circumjacent to the inflow and exhaust orifices (shown in FIG. 7B). In another embodiment, not shown, an open pitch coil can be configured to helically wrap around at least a segment of the shaft 122 at the distal portion 726. In this embodiment, the coil can be a round or flattened wire or other thin material having a diameter or width less than a first or second orifice diameter such that the coil does not interfere with or does not otherwise occlude an undesirable area of the inflow and exhaust orifices 740, 752.

In operation, the refrigerant 106 passes through the supply lumen 732, through the distal end 736, through the inflow orifice 740, and into the expansion chamber 143 defined by the balloon 142. As the refrigerant 106 passes through the distal end 736 and the inflow orifice 740, it expands into a gaseous phase, thereby inflating the balloon 142 and causing a significant temperature drop in the expansion chamber 143. The portion of the applicator 140 contacting the tissue at the target T can be a heat-transfer region 760 which, when operating with flowing refrigerant 106 in the expansion chamber 143, causes therapeutically-effective, cryogenic renal neuromodulation. Exhausted refrigerant 117 passes through the one or more exhaust orifices 752 in the distal portion 626 of the shaft 122 and in a proximal direction into the exhaust passage 750.

Figure 8B:
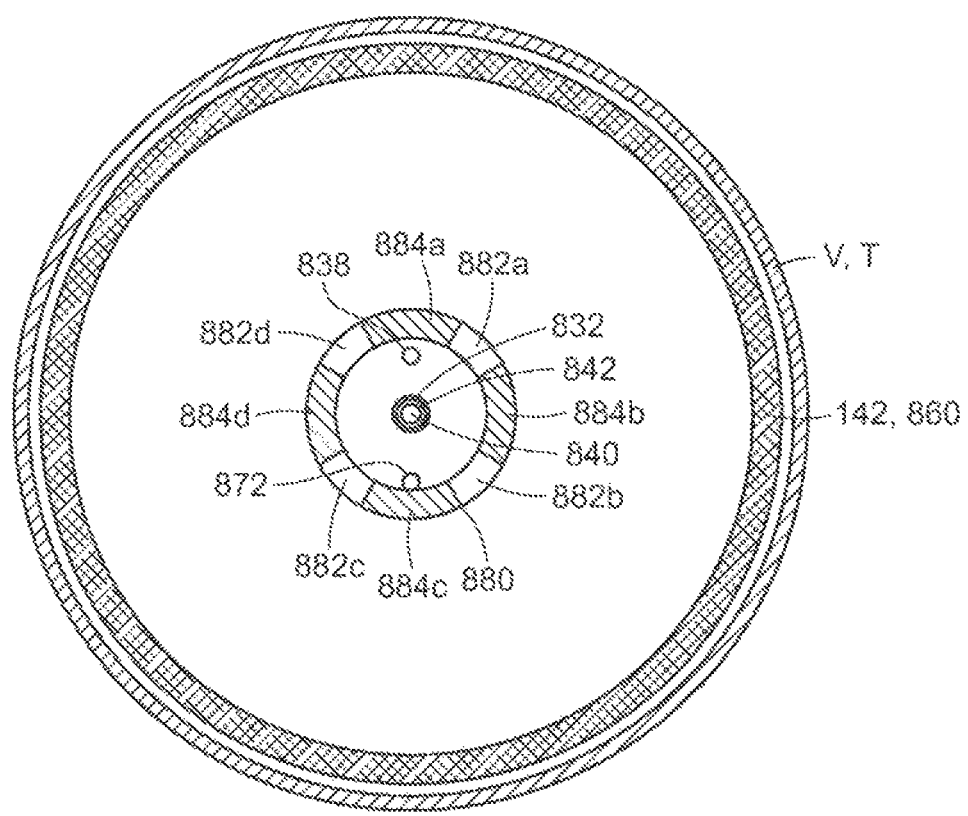

FIGS. 8A-8B illustrate a distal portion 826 of a cryotherapeutic device 820 configured in accordance with additional embodiments of the present technology. FIG. 8A is an enlarged cross-sectional view of the distal portion 826 that includes features generally similar to the features of the cryotherapeutic devices 620, 720 described above with reference to FIGS. 6-7B. For example, the second zone 127b of the distal portion 826 of the shaft 122 extends axially through the expansion chamber 143 of the balloon 142 to the distal connector 148 and/or the atraumatic tip 150. However, in the embodiment shown in FIG. 8A, the second zone 127b includes a plurality of apertures 880 formed longitudinally along the distal portion 826 of the shaft 122 to provide openings 882 through which refrigerant 106 can flow freely to the expansion chamber 143 from a supply lumen 832 and through which exhausted refrigerant 117 can flow freely from the expansion chamber 143 to an exhaust passage 850.

FIG. 8B is an enlarged cross-sectional view of the distal portion 826 of the cryotherapeutic device 820 of FIG. 8A at plane line 8B-8B. In looking proximally with respect to the shaft 122, and with reference to FIG. 8B, one or more leg portions 884 (individually identified in FIG. 8B as 884a-d) of the shaft 122 are created by the apertures 880, wherein around a circumference of the shaft, each opening 882 (individually identified in FIG. 8B as 882a-d) is flanked by a leg portion 884 of the shaft 122. For example, opening 882a is flanked by leg portions 884a and 884b. The leg portions 884 that extend through the expansion chamber 143 to the distal connector 148 and/or atraumatic tip 150 can provide support for the tip 150 and/or brace the balloon 142 during delivery and deployment phases.

Referring back to FIG. 8A, the leg portions 884 extending through the expansion chamber 143 can be further reinforced with a shaft support, such as an open pitch coil 890 (shown in dotted lines) wrapped around at least a portion of the leg portions 884 and/or other regions of the distal portion 826 of the shaft 122. In one embodiment, the coil 890 is suitable to maintain flexibility and torqueability of the cooling assembly 830 as it moves through the vasculature V to the target site T. Additionally, the coil 890 can prevent the leg portions 884 from bowing or kinking under pressure when the balloon 142 is inflated. As the balloon 142 inflates during deployment, the leg portions 884, alone or in combination with the coil 890, can provide tip support and added strength to the cooling assembly 830. In some embodiments, the coil 890 can be a round or flattened wire or other thin support material that does not interfere with or does not otherwise occlude the openings 882.

The supply lumen 832 can include an inflow opening at a distal end 836 for directing the refrigerant 106 into the distal portion 826 of the shaft 122. In another embodiment, the cryotherapeutic device 820 can include a capillary tube 842 which can be similar to the capillary tube 636 (FIG. 6). In this embodiment, an inflow opening 840 can be located at a distal tube end 844 of the capillary tube 842. As described above, the capillary tube 842 can be positioned and/or inserted into the supply lumen 832. The capillary tube 842 and/or a distal tube end 844 of the capillary tube 842 can have a diameter less than that of the supply lumen 832 to impede the flow of refrigerant 106 and/or increase a cooling effect within the expansion chamber 143. For example, the supply lumen 832, the capillary tube 842 and/or the inflow opening 840 can all be configured, alone or in combination, to direct expansion (e.g., into a gaseous phase) of refrigerant 106 toward the applicator 140 (e.g., through the openings 882), thereby inflating the balloon 142 and causing a significant temperature drop in the expansion chamber 143 and at a heat-transfer region 860 in contact with the vascular tissue at the target T for delivering cryotherapy.

The cryotherapeutic device 820 can also include a pressure monitoring lumen 872 with distal portion 874, a temperature sensor or thermocouple 838, and a thermocouple lead 839 coupled to the thermocouple 838. The distal portion 874 and the thermocouple 838 can be configured and suitably positioned within the distal portion 826 of the shaft 122 to be in fluid communication with the expansion chamber 143. In one embodiment, the distal portion 874 of the pressure monitoring lumen 872, the thermocouple 838 and a distal end 836 of the supply lumen 832 can partially extend into the distal portion 826 of the shaft 122 encompassed by the expandable chamber 143. In one arrangement, and as shown in FIG. 8A, one or more of the distal portion 874 of the pressure monitoring lumen 872, the thermocouple 838 and/or the distal end 836 of the supply lumen 832 can be proximal to the openings 882 along the shaft 122. In another arrangement, not shown, one or more of the distal portion 874 of the pressure monitoring lumen 872, the thermocouple 838 and/or the distal end 836 of the supply lumen 832 can extend along the distal portion 826 of the shaft 122 into cross-sectional alignment with one or more of the openings 882.

While the embodiment illustrated in FIGS. 8A-8B illustrates a plurality of leg portions 884 for supporting the atraumatic tip 150, it will be understood by those in the art that one leg portion 884 can be suitable for supporting the tip 150 and/or the cooling assembly 830. Further, it will be understood that the tip support need not be formed from a portion of the distal portion 826 of the shaft 122. For example, one or more support members (not shown) that extend from the shaft 122 axially through the balloon 142 to the distal connector 148 or atraumatic tip 150 can be configured to axially support the cooling assembly 830 during delivery and deployment phases. In yet further embodiments (not shown), a guide wire lumen (not shown) can extend distally through at least a portion of the shaft 122 and be configured to extend through the balloon 142 to the distal connector 148 or atraumatic tip 150 to provide support for the cooling assembly 830 during delivery and/or deployment configurations.

FIG. 9A is an enlarged cross-sectional view of proximal 924 and distal portions 926 of a cryotherapeutic device 920 and FIG. 9B is a top plan view of the proximal 924 and distal portions 926 shown in FIG. 9B configured in accordance with yet another embodiment of the present technology. As shown in FIGS. 9A and 9B, the cryotherapeutic device 920 includes a shaft 922 having a proximal portion 924 and an independent distal portion 926 separate from the proximal portion 924. The proximal portion 924 and the independent distal portion 926 can be joined at a junction 940. Referring to FIG. 9A, the proximal portion 924 can also include a neck region 952 adjacent to a terminal end 925. The neck region 952 can have an outer diameter $OD_1$ less than an outer diameter $OD_2$ of the remainder of the proximal region 924. As shown, the outer diameter $OD_1$ of the neck region 952 is less than an inner diameter $ID_1$ of the independent distal portion 926 such that the independent distal portion 926 can slide over the neck region 952. The independent distal portion 926 can be attached (e.g., via thermal bonding, adhesives, or some other suitable attachment mechanism known in the art) to the neck region 952 of the proximal portion 924. When joined, the outer diameter $OD_2$ of the proximal portion 924 can be substantially the same as an outer diameter of the independent distal portion such that the shaft 922 has substantially the same outer profile. In other embodiments the outer or inner diameters of the proximal portion 924, the neck region 952 and the independent distal portion 926 could be different than described here. For example, the independent distal portion 926 could have an overall lower profile than the proximal portion.

The cryotherapeutic device 920 further includes a guide wire lumen 931 through which a guide wire 933 can be received to guide the distal portion 926 of the shaft 922 through the vasculature. In the embodiment illustrated in FIG. 9A, the guide wire lumen 931 extends through only a portion of the shaft 922 in a rapid exchange (RX) configuration. RX guide wires can also be used to manipulate and enhance control of the shaft 922 and the cooling assembly 130 (FIG. 1).

In the illustrated embodiment, the proximal end 977 of the guide wire lumen 976 is shown extending through a sidewall of the shaft 922 at the junction 940 between the proximal portion 924 and the independent distal portion 926 of the shaft 922. Referring to FIG. 9B, the proximal portion 924 includes a passage 950 (e.g., a slot, a channel, an opening, an aperture, a recessed portion, or another suitable structure) at or in a terminal end 925 of the proximal portion 924. The passage 950 can have an opening 956 configured to receive the proximal end 977 of the guide wire lumen 976. When connected to the proximal portion 926, a proximal end 929 of the distal portion 926 seals access (e.g., the opening 956 is not accessible at the junction) to the passage 950 at the terminal end 925 creating an access space 954 configured and sized to accommodate the guide wire lumen 976. In some embodiments, the access space 954 can also include an additional seal or bonding material (not shown) to seal the inner lumen of the shaft 922 from the surrounding sheath 154 (FIGS. 2-3) or the surrounding environment (e.g., the vessel and/or bodily fluid). In further embodiments, not shown, the junction 940 could be configured differently, for example, by including the neck portion 952 and/or the passage 950 on the independent distal portion 926.

The length of the proximal portion 924 and the length of the independent distal portion 926 are relative to the total length of the shaft 922 (e.g., at least 48 inches (122 cm)) and it is understood that the proximal end 977 of the guide wire lumen 976 can be accessible anywhere between the proximal and distal ends of the shaft 122. Accordingly, while it is described, with reference to FIG. 9A, that the junction 940 is located at a point where the proximal portion 924 and the independent distal portion 926 are joined, one of ordinary skill in the art will recognize that the junction 940 can be placed anywhere along the length of the shaft 922 proximal to the cooling assembly 130 (FIG. 1). In some arrangements, the junction 940 can be located proximally adjacent to the cooling assembly 130 (FIG. 1), in which the length the independent distal portion 926 would be less than the length of the proximal portion 924.

In another embodiment, not shown, the junction 940 could be located entirely within a distal portion (e.g., distal portion 126, FIGS. 2-3) of the shaft 922. For example, the first zone 127a and the second zone 127b (FIGS. 2-3) could be independent distal portion components that, when joined, could create a junction having the passage 950 and access space 954 as described through which a guide wire lumen and guide wire could extend. The guide wire lumen 976 and the junction 940 having the passage 950 shown in FIGS. 9A-9B, or variations thereof, may be included in various embodiments described herein to facilitate navigation through the vasculature. Suitable RX guide wire configurations are disclosed in, U.S. Patent Publication No. 2003/0040769, filed Aug. 23, 2001, and U.S. Patent Publication No. 2008/0171979, filed Oct. 17, 2006, each of which is incorporated herein by reference in its entirety.

Some features of the cryotherapeutic device 920 and the shaft 922 are not shown in FIGS. 9A-9B for simplicity. However, one of ordinary skill will understand that the shaft 922 can house components of the systems and devices described above with reference to FIGS. 1-8B. For example, the cryotherapeutic device 920 can include a supply lumen (not shown) and an exhaust lumen (not shown) extending along at least a portion of the shaft 922 and through the junction 940. The cryotherapeutic device 920 may also include a pressure monitoring lumen (not shown) and a temperature sensor (e.g., thermocouple) lead (not shown) along at least a portion of the shaft 922 and through the junction 940. These described features are exemplary in nature and are not meant to be a complete list of all cryotherapeutic device 920 and system 100 components that may be housed in the shaft 922 and/or extend through the junction 940.

In one embodiment, the proximal portion 924 and/or the independent distal portion 926 of the shaft 922 can include one or more polymers, such as polyimide, which can provide flexibility and pushability qualities to the shaft 922 when in operation (e.g., when positioning the cooling assembly 130 (FIG. 1) in a renal artery or renal ostium (as described in FIGS. 4-5)). In one embodiment, the proximal portion 924 and/or the independent distal portion 926 can include a braided polyimide material for providing increased torqueability and/or, in some instances, protect the shaft 922 from bending (e.g., kinking) inside the vasculature during delivery and/or during deployment of the cooling assembly 130 (FIGS. 1-3). In other embodiments, a skilled artisan will recognize that the proximal and distal portions 924, 926 can be made of a variety of suitable materials, such as nylon, polyamide (e.g., GRILAMID® L25) and polyether block amide (Pebax® polyether block amide), among others. In some embodiments the proximal and independent distal portions 924, 926 can be made from the same material, and in other embodiments, the portions 924, 926 can be made from different materials. In one embodiment, the shaft 922 can be made from polyimide or braided polyimide and the guide wire lumen 976 can be made from polyamide, polyimide or a GRILAMID® trilayer (GRILAMID® TR55, L25, L20). In another embodiment, the distal portion 926 can be Pebax and/or GRILAMID® L20, L25, and the proximal portion can be braided polyimide and or Braided GRILAMID® (GRILAMID® TR55, L25, L20). The supply lumen (not shown) and/or the pressure monitoring lumen (not shown) can be made from stainless steel, or in other embodiments, polyimide.

Figure 10A:
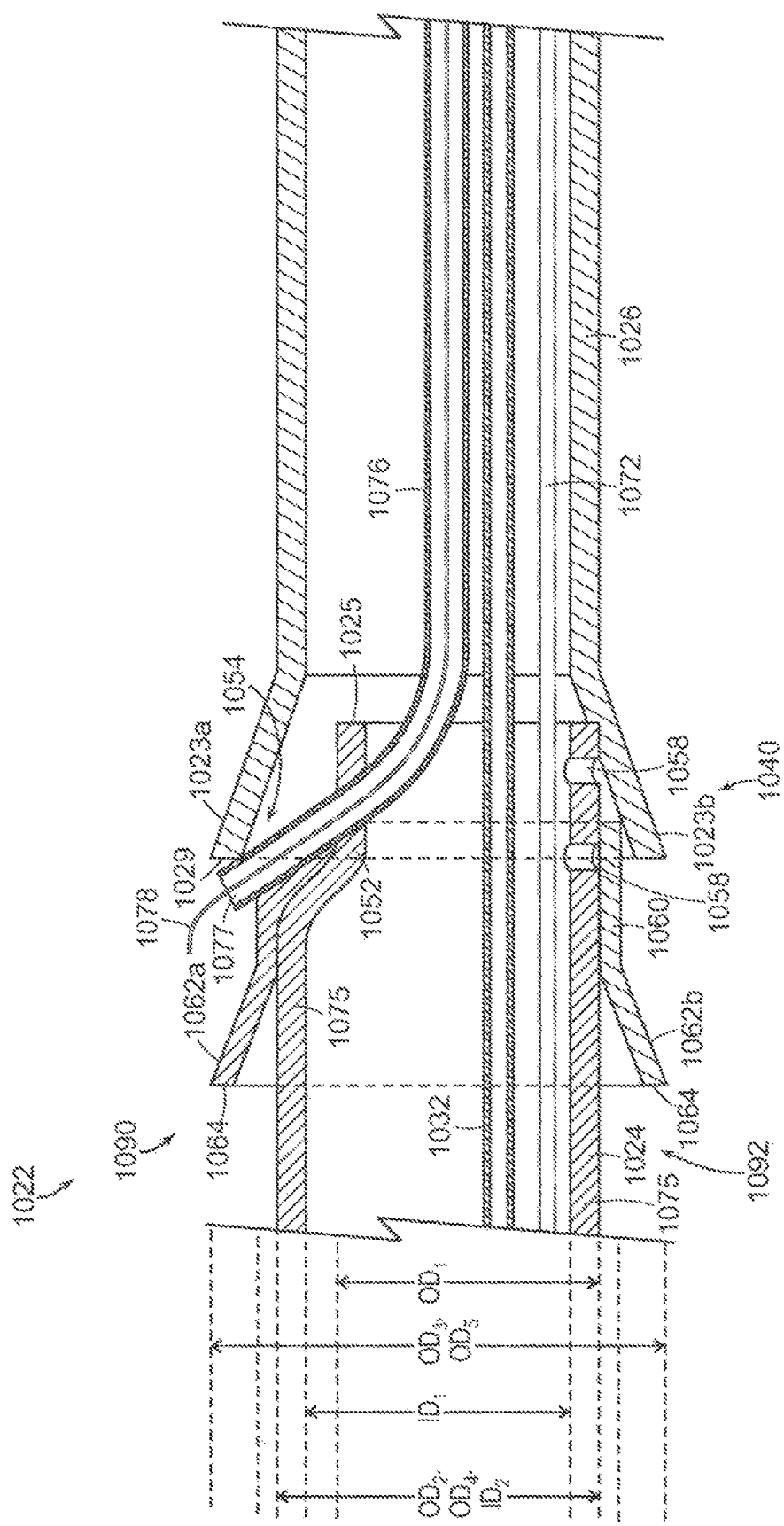

FIGS. 10A-10B are enlarged cross-sectional views of a proximal portion 1024 and an independent distal portion 1026 of a cryotherapeutic device 1020 configured in accordance with yet another embodiment of the present technology and showing an intermediate manufacturing state (FIG. 10A) and a state configured for use in a system (FIG. 10B) such as the cryotherapeutic system 100 (FIG. 1). The proximal 1024 and independent distal portions 1026 of the cryotherapeutic device 1020 include features generally similar to the features of the cryotherapeutic device 920 described above with reference to FIGS. 9A-9B. For example, and in reference to FIG. 10A, the cryotherapeutic device 1020 includes a shaft 1022 having the proximal portion 1024 with a passage (similar to passage 950, FIG. 9B) at a terminal end 1025, and having the independent distal portion 1026 separate from the proximal portion 1024. However, in the embodiment shown in FIGS. 10A and 10B, the shaft 1022 also includes an intermediate portion 1060 that is initially separate from the proximal 1024 and independent distal portions 1026. The proximal portion 1024, the intermediate portion 1060 and the independent distal portion 1026 can be joined at a junction 1040 at a position along the shaft 1022 where a guide wire lumen 1076 can extend through a sidewall 1075 of the shaft 1022 in a rapid exchange (RX) configuration. As described above with respect to FIGS. 9A-9B, the guide wire lumen 1076 can be configured to receive a guide wire 1078 for guiding the distal portion 1026 of the shaft 1022 through the vasculature. RX guide wires can also be used to manipulate and enhance control of the shaft 1022 and the cooling assembly 130 (FIG. 1).

As shown in FIG. 10A, and at an intermediate manufacturing step, the proximal portion 1024 includes a neck down region 1052 on a first area 1090 of the proximal portion 1024 adjacent to a terminal end 1025. The proximal portion 1024 can also include one or more holes 1058 disposed in the sidewall 1075 of the proximal portion 1024 at a second area 1092, the second area 1092 positioned apart from the first area 1090. The neck down region 1052 can change the diameter of the shaft 1022. For example, the outer diameter of the necked down region 1052 can have an outer diameter $OD_1$ less than an outer diameter $OD_2$ of the remainder of the proximal region 1024. As shown, the outer diameter $OD_1$ of the neck region 1052 is less than an inner diameter $ID_1$ of the independent distal portion 1026 such that the independent distal portion 1026 can slide over the neck down region 1052. The distal portion 1026 can include a set of first flares 1023 (identified individually as 1023a-b) at a proximal end 1029 of the distal portion 1026. An outer diameter $OD_3$ of the first flares 1023a-b, is greater than the outer diameter $OD_2$ of the proximal region 1024, the outer diameter $OD_1$ of the necked down region 1052, and an outer diameter $OD_4$ of the remainder of the distal region 1026.

In one embodiment, the intermediate portion 1060 includes a set of second flares 1062 (identified individually as 1062*a-b*) at a proximal end 1064 of the intermediate portion 1060. The intermediate portion 1060 has an inner diameter $ID_2$ that is approximately the same as or greater than the outer diameter $OD_2$ of the proximal portion 1024 such that the intermediate portion 1060 can slide over the neck down region 1052 to a position proximal to the passage (not shown in FIG. 10A side view) and guide wire lumen 1076 extending from the passage (not shown). The second flares 1062*a-b* have an outer diameter $OD_5$ greater than the outer diameter $OD_2$ of the proximal portion 1024. As stated above, and during manufacturing of the shaft 1022 (FIG. 10A), the intermediate portion 1060 slides over the terminal end 1025 to a position proximal to the passage (not shown in side view).

Also, during manufacturing of the shaft 1022, the independent proximal portion 1026 slides over the terminal end 1025 to a point at which the proximal end 1029 of the distal portion 1026 is adjacent the guide wire lumen 1076 extending through the sidewall 1075 of the shaft 1022 at an access space 1054 created by the passage (such as passage 950, FIG. 9B). The flare 1023*b* may also surround a portion of the intermediate portion 1060 on the second side 1092 of the shaft 1022.

Following the positioning of the proximal portion 1024, at least a portion of the shaft 1022 at the junction 1040 can be covered with heat shrink and heat bonded, for example, to shrink the intermediate portion 1060 with flares 1062*a-b* and the proximal end 1029 of the independent distal portion having flares 1023*a-b* to form a plurality of seals 1080, 1082, 1084 and 1086 at the junction 1040. As shown in FIG. 10B, the seals 1080, 1082, 1084 and 1086 can seal the inner lumen of the shaft 1022 from the surrounding sheath 154 (FIGS. 2-3) or the surrounding environment (e.g., the vessel and/or bodily fluid) as well as prevent exhausted refrigerant 117 from leaking from the inner lumen of the shaft 1022. For example, the flare portion 1023*a* (FIG. 10A) can be heat bonded to form the seal 1080 distal and adjacent to the guide wire lumen 1076 (FIG. 10B). Likewise, flare 1062*a* can be heat bonded to form the seal 1082 proximal and adjacent to the guide wire lumen 1076. As shown in FIGS. 10A-10B, flare 1062*b* and flare 1023*b* can be heat bonded to form seals 1084 and 1086, respectively. In some embodiments containing the holes 1058 as shown in FIGS. 10A-10B, the heat sealing process can allow material from the independent portion 1060 and the independent distal portion 1026 to melt into the holes 1058 disposed in the proximal portion 1024 such that the bond strength at the junction 1040 is increased.

As shown in FIG. 10B, thermal bonding of the proximal portion 1024, the intermediate portion 1060, and the independent distal portion 1026 can effectively join these components in a manner that creates a strong but flexible bond across the junction 1040 while allowing the guide wire lumen to access the inner lumen of the shaft 1022 in an RX configuration as described above. It is understood that other mechanisms known in the art (e.g., laser bonding, adhesives, or some other suitable attachment mechanism known in the art) can be used to join and seal the proximal, intermediate and distal portions together.

In some embodiments, the proximal portion 1024, the intermediate portion 1060 and/or the independent distal portion 1026 of the shaft 1022 can include one or more polymers, such as polyimide, which can provide flexibility and pushability qualities to the shaft 1022 when in operation. In certain embodiments, the portions 1024, 1060, 1026 can include a braided polyimide material for providing increased torqueability and/or, in some instances, protect the shaft 1022 from bending (e.g., kinking) inside the vasculature during delivery and/or during deployment of the cooling assembly 130 (FIGS. 1-3). In some embodiments, the proximal portion 1024 can be polyamide (e.g., GRILAMID® polyamide), braided polyimide and/or braided GRILAMID® polymer (GRILAMID® TR55, L25, L20). The independent distal portion 1026 can include polyether block amide (Pebax® polyether block amide) and/or GRILAMID® polymer (e.g., GRILAMID® L25, L20). In some embodiments the intermediate portion 1060 can include the same materials as the independent distal portion 1026 (e.g., polyether block amide (Pebax® polyether block amide) and/or GRILAMID® polymer (e.g., GRILAMID® L25, L20)). In other embodiments, a skilled artisan will recognize that the proximal, distal and intermediate portions 1024, 1026, 1060 can be made of a variety of suitable materials (e.g., nylon) used for extruded medical tubing. In one embodiment, the shaft 1022 can be made from polyimide, polyamide, braided polyamide, braided polyimide and/or polyether block amide (e.g., Pebax® polymer) and the guide wire lumen 1076 can be made from polyamide, polyimide or a GRILAMID® trilayer (GRILAMID® TR55, L25, L20). The supply lumen 1032 and/or the pressure monitoring lumen 1072 can be made from stainless steel, or in other embodiments, polyimide.

Figure 11A:
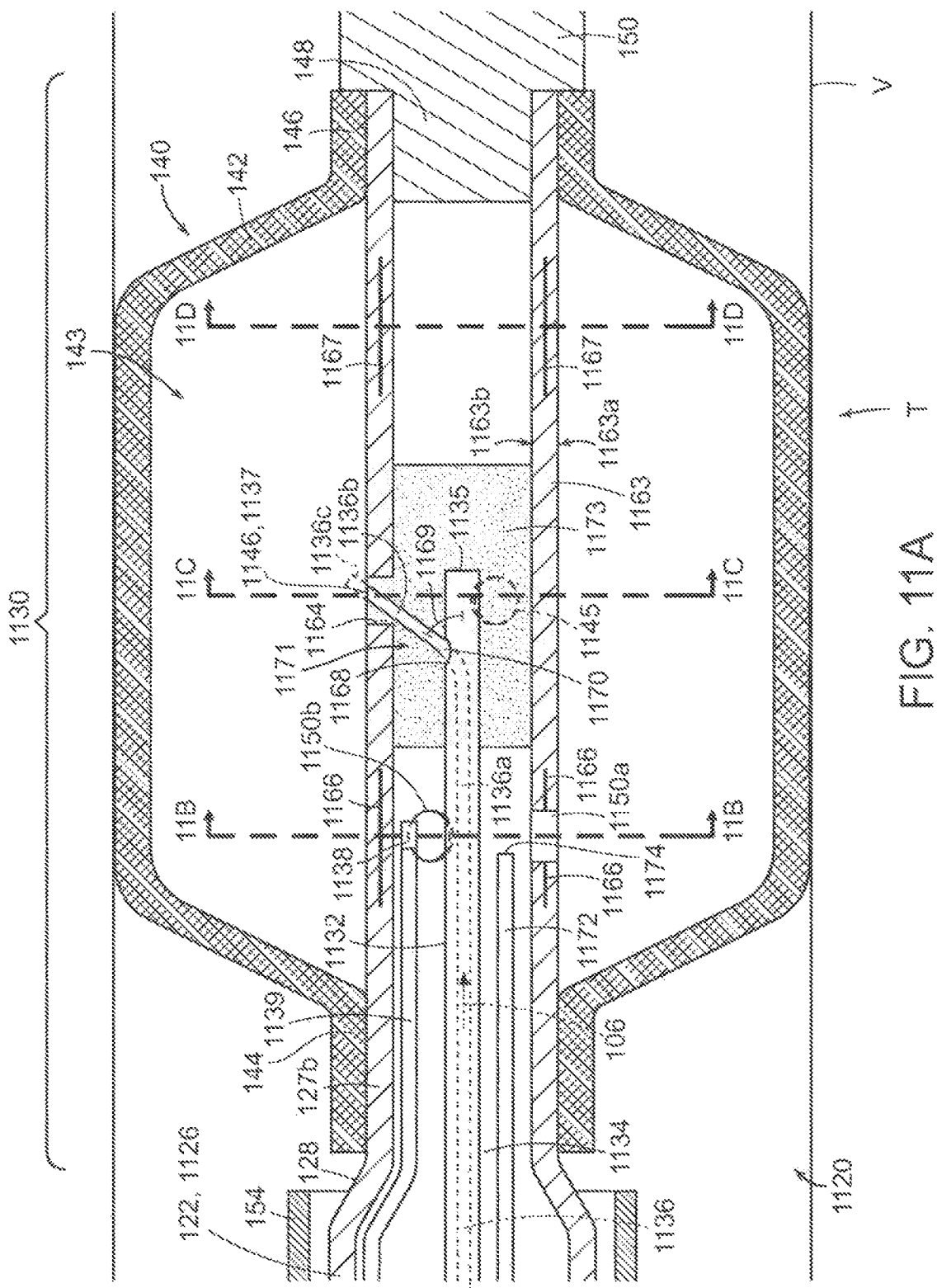
FIG. 11A is a side cross-sectional view of a cryotherapeutic device having a plug configured in accordance with another embodiment of the present technology.
Figure 11B:
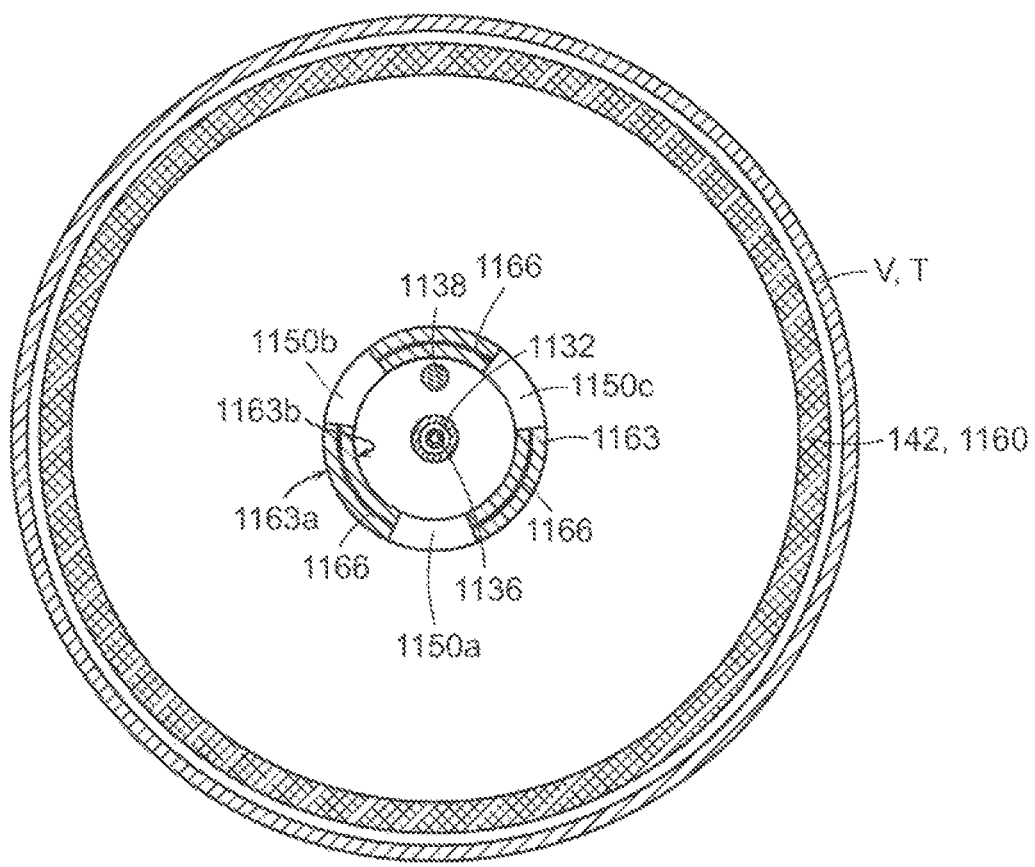
FIGS. 11B-11D are cross-sectional views of the cryotherapeutic device shown in FIG. 11A taken along the lines 11B-11B, 11C-11C, and 11D-11D, respectively.
Figure 11C:
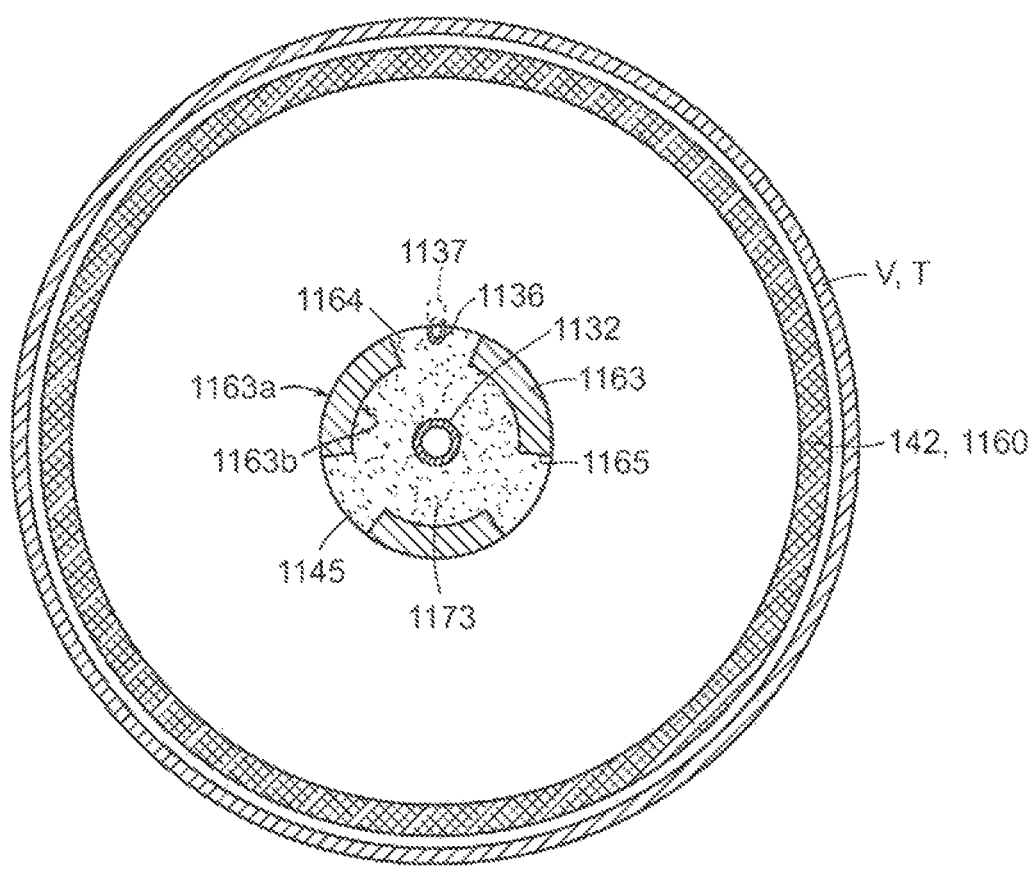
Figure 11D:
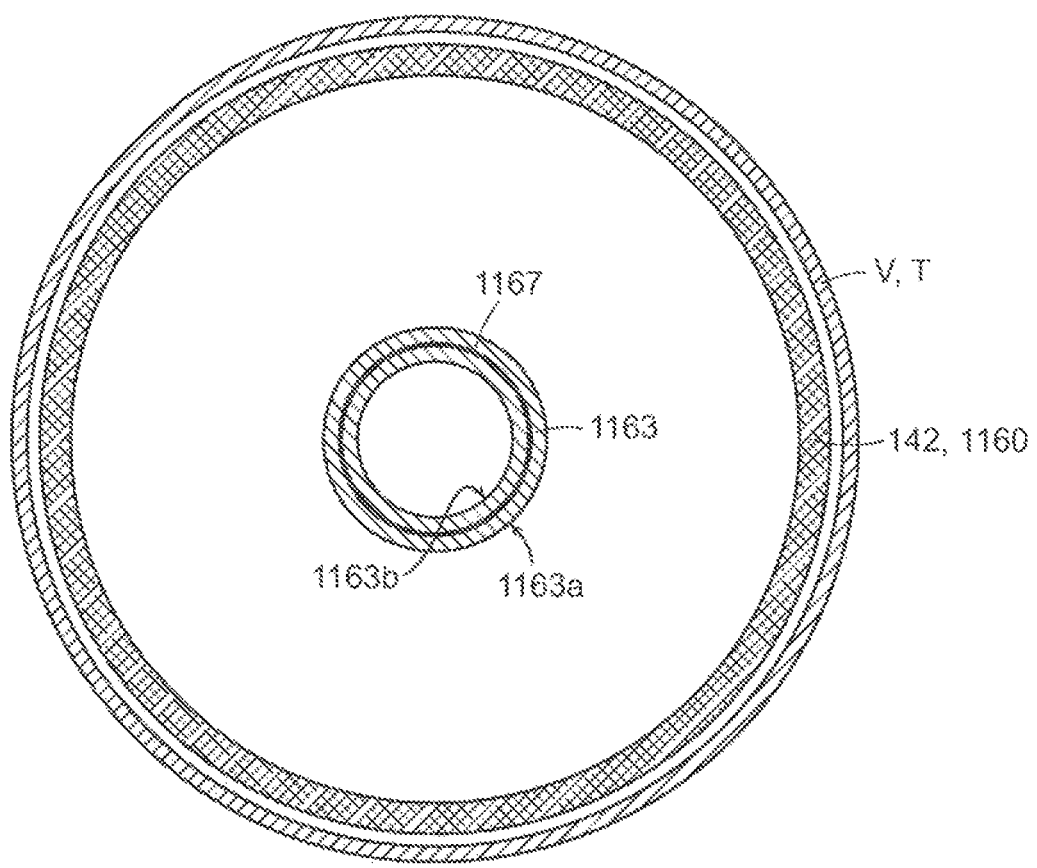

FIG. 11A is a side cross-sectional view of a cryotherapeutic device 1120 configured in accordance with an embodiment of the present technology. FIGS. 11B-11D are cross-sectional views of the cryotherapeutic device 1120 shown in FIG. 11A taken along the lines 11B-11B, 11C-11C, and 11D-11D, respectively. As shown in FIG. 11A, the cryotherapeutic device 1120 can include several features generally similar to the features of the cryotherapeutic device 120 described above with reference to FIGS. 1-3. For example, the cryotherapeutic device 1120 can include the shaft 122, the applicator 140, the balloon 142, the expansion chamber 143, the proximal attachment region 144, the distal attachment region 146, the distal connector 148, and the atraumatic tip 150 of the cryotherapeutic device 120 described above with reference to FIGS. 1-3. With reference again to FIG. 11A, the cryotherapeutic device 1120 can include a cooling assembly 1130 at a distal portion 1126 of the shaft 122. The cooling assembly 1130 can include the applicator 140, which can include an expandable member, such as the balloon 142 or another suitable expandable member. The expandable member can define at least a portion of the expansion chamber 143 and can have a delivery state (e.g., a collapsed configuration) and a deployed state (e.g., an expanded configuration), with the deployed state shown in FIGS. 11A-11D.

The device 1120 can further include a supply tube 1132 housed within at least a portion of the shaft 122. The supply tube 1132 can be configured to transport refrigerant 106 within the shaft 122 to the distal portion 1126. At the distal portion 1126, the device 1120 can include an orifice 1146 through which the refrigerant 106 can flow into the expansion chamber 143. The distal portion 1126 can include a wall 1163 having an outer surface 1163*a* toward the expansion chamber 143 and an inner surface 1163*b* opposite the outer surface 1163*a*. The distal portion 1126 can further include a first lateral opening 1164 through the wall 1163. In some embodiments, the first lateral opening 1164 can be generally centered along the length of the distal portion 1126 within the expansion chamber 143. The device 1120 can be configured such that refrigerant 106 flows into the expansion chamber 143 via the first lateral opening 1164. Accordingly, positioning the first lateral opening 1164 centrally within the expansion chamber 143 can be useful in some cases to promote more even distribution or to otherwise control distribution of the refrigerant 106 within the expansion chamber 143. In other embodiments, the first lateral opening 1164 can have other suitable positions.

As shown in FIG. 11A, the device 1120 can further include a capillary tube 1136 having a first portion 1136a within the supply tube 1132 and a second portion 1136b extending from the supply tube 1132 to the first lateral opening 1164. For example, the supply tube 1132 can include a second lateral opening 1168 and the capillary tube 1136 can include a transition region 1171 between the first and second portions 1136a, 1136b of the capillary tube 1136 proximate the second lateral opening 1168. In other embodiments, the capillary tube 1136 can extend from a terminal opening 1135 of the supply tube 1132 and the transition region 1171 can be proximate the terminal opening 1135. In still other embodiments, the device 1120 can include more than one capillary tube 1136. For example, the device 1120 can include two, three, four, or a greater number of capillary tubes 1136 extending from the terminal opening 1135, the second lateral opening 1168, and/or other openings (not shown) of the supply tube 1132. Such additional capillary tubes 1136 can extend from the supply tube 1132 to other lateral openings (not shown) of the distal portion 1126 of the shaft 122 (e.g., other lateral openings radially spaced apart around the circumference of the shaft 122). Multiple capillary tubes 1136 can be useful, for example, when the device 1120 includes multiple balloons 142.

With reference to FIGS. 11A and 11B, the capillary tube 1136 can be more flexible than the supply tube 1132, such as when the capillary tube 1136 has thinner walls than the supply tube 1132 and/or is made from a different material than the supply tube 1132. Accordingly, in some cases, it can be challenging to form a sufficient bend in the supply tube 1132 that allows the supply tube 1132 to directly deliver the refrigerant 106 to the first lateral opening 1164 because of the stiffness of the supply tube 1132. Instead of or in addition to bending the supply tube 1132, the more flexible capillary tube 1136 can include a sufficiently angled elbow 1170 proximate the transition region 1171. The elbow 1170 can define a suitable angle 1169 relative to the supply tube 1132 such that the second portion 1136b of the capillary tube 1136 can extend from the supply tube 1132 to the first lateral opening 1164 at the angle 1169.

In some embodiments, one or more features of the transition region 1171 can be selected to reduce flow impedance within the capillary tube 1136. This can increase the efficiency of the device 1120 (e.g., by reducing heat-absorbing expansion of the refrigerant 106 before the refrigerant 106 reaches the expansion chamber 143). As shown in FIG. 11A, the elbow 1170 can be rounded and/or the angle 1169 can be less than about 80° (e.g., from about 25° to about 75°). In other embodiments, the elbow 1170 can have other suitable configurations. The supply tube 1132 can be sealed around the capillary tube 1136 so that the refrigerant 106 within the supply tube 1132 is forced through the capillary tube 1136. The capillary tube 1136 can further include a distal end 1137 that defines the orifice 1146. As shown in FIG. 11A, the distal end 1137 and the orifice 1146 can be generally flush with the outer surface 1163a and non-perpendicular (e.g., bias cut) relative to the length of the second portion 1136b. In other embodiments, the distal end 1137 and the orifice 1146 can have other suitable configurations. For example, the second portion 1136b can project beyond the outer surface 1163a causing the distal end 1137 and the orifice 1146 to be spaced apart from the outer surface 1163a.

In some embodiments, generally all expansion of the refrigerant 106 can occur as the refrigerant 106 exits the orifice 1146. In other embodiments, an intervening distributor (e.g., the distributor 640 shown in FIG. 6) can be used. Under certain process conditions, an intervening distributor may cause the refrigerant 106 to evaporate and then recondense before entering the expansion chamber 143. For example, with reference to FIG. 6, flow impedance associated with exiting the distributor 640 via the orifices 646 can cause the refrigerant 106 to recondense within the distributor 640 after exiting the capillary tube 636. Furthermore, relative to the embodiment shown in FIG. 6, the device 1120 can reduce the possibility and/or degree to which the refrigerant 106 pools within and/or near the expansion chamber 143. Such pooling can be disadvantageous, for example, because pooled refrigerant can cause uneven cooling of the balloon 142. For example, portions of the balloon 142 adjacent to the pooled refrigerant can be warmer than other portions of the balloon 142, and, accordingly, may not reach temperatures desirable for cryotherapy. The presence of pooled refrigerant can also increase the total quantity of the refrigerant 106 within the cooling assembly 1130 during use, and thus increase the amount of the refrigerant 106 potentially released into the vessel (V) in the event of a failure of the balloon 142. Such a release can be difficult to prevent even if the supply of the refrigerant 106 is immediately terminated after the failure occurs. With reference to FIG. 11A, routing the capillary tube 1136 through the wall 1163 of the distal portion 1126 can facilitate rapid expansion of the refrigerant 106 with little or no pooling. In some cases, however, pooling of the refrigerant 106 can be acceptable or even desirable. For example, even distribution of the refrigerant 106 within the expansion chamber 143 and/or other benefits of intervening structures (e.g., the distributor 640 shown in FIG. 6) can, in some cases, outweigh any disadvantages of pooling.

With reference to FIGS. 11A and 11C, the device 1120 can include a plug 1173 within the distal portion 1126 that extends around the second portion 1136b of the capillary tube 1136. As shown in FIG. 11A, the plug 1173 can extend into the first lateral opening 1164 around the second portion 1136b of the capillary tube 1136. In some embodiments, generally all of the capillary tube 1136 can be within a combination of the supply tube 1132 and the plug 1173. The distal portion 1126 can further include an injection hole 1145 and a vent 1165 through the wall 1163 proximate the plug 1173. The first lateral opening 1164, the injection hole 1145, and the vent 1165 (FIG. 11C) can be circumferentially spaced apart in a first plane perpendicular to a length of the distal portion 1126. The injection hole 1145 and the vent 1165 can be useful in some methods for making the device 1120 in accordance with embodiments of the present technology, as described in greater detail below. In some embodiments, the plug 1173 can provide structural support to the second portion 1136b of the capillary tube 1136, form a barrier within the distal portion 1126, serve as a radiopaque marker, and/or serve one or more other functions.

With reference to FIGS. 11A and 11B, the refrigerant 106 can exit the expansion chamber 143 via an exhaust path 1134 extending from the expansion chamber 143 along at least a portion of the shaft 122. The exhaust path 1134 can include exhaust openings (individually identified as 1150a-c) circumferentially spaced apart from each other in a second plane perpendicular to the length of the distal portion 1126 and proximal to the plug 1173. In some embodiments, the circumferential positions of the first lateral opening 1164, the injection hole 1145, and the vent 1165 in the first plane can be offset relative to the circumferential positions of the exhaust openings 1150a-c in the second plane. This can enhance the structural integrity of the distal portion 1126 and/or facilitate manufacturing, among other benefits.

As shown in FIG. 11A, the device 1120 can include a temperature sensor 1138 within the distal portion 1126 proximate the exhaust openings 1150a-c and a lead 1139 extending proximally from the temperature sensor 1138. Similarly, the device 1120 can include a pressure-monitoring tube 1172 having a distal opening 1174 proximate the exhaust openings 1150a-c. The exhaust path 1134 can extend along the shaft 122 through a space around the lead 1139, the pressure-monitoring tube 1172, and the supply tube 1132. During operation, the temperature of the refrigerant 106 can increase and the pressure of the refrigerant 106 can decrease as the refrigerant 106 moves proximally from the exhaust openings 1150a-c. Thus, positioning the temperature sensor 1138 and the distal opening 1174 of the pressure-monitoring tube 1172 as close as possible to the exhaust openings 1150a-c can facilitate more accurate measurement of the temperature and pressure within the expansion chamber 143. The distance between the distal opening 1174 of the pressure-monitoring tube 1172 and the plug 1173 can be, for example, from about 0.5 millimeter to about 2 millimeters, from about 1 millimeter to about 1.5 millimeters, or within another suitable range.

In some embodiments, the distal portion 1126 can include at least one reinforcing member 1166 and the exhaust openings 1150a-c can extend through the reinforcing member 1166 to reduce or prevent unwanted bending or kinking of the distal portion 1126 in the region of the exhaust openings 1150a-c. The reinforcing member 1166 can be a first reinforcing member proximally spaced apart from the first lateral opening 1164, and the distal portion 1126 can further include at least one second reinforcing member 1167 distally spaced apart from the first lateral opening 1164. The first and second reinforcing members 1166, 1167 can be radiopaque bands that also serve as markers. In some embodiments, the first and second reinforcing members, respectively, can be spaced apart from the first lateral opening 1164 by generally equal distances. As shown in FIGS. 11A, 11B, and 11D, the first and second reinforcing members 1166, 1167 can be embedded in the wall 1163 of the distal portion 1126. For example, the wall 1163 can include multiple layers (not shown), and the first and second reinforcing members 1166, 1167 can be positioned between two of the layers (e.g., laminated between layers of the wall 1163).

A method for making the device 1120 in accordance with an embodiment of the present technology can include positioning the capillary tube 1136 such that the first portion 1136a of the capillary tube 1136 is within the supply tube 1132 and the second portion 1136b of the capillary tube 1136 extends from the second lateral opening 1168 of the supply tube 1136. The supply tube 1136 can then be sealed around the first portion 1136a of the capillary tube 1136. For example, an annular space between an outer wall of the first portion 1136a of the capillary tube 1136 can be bonded (e.g., with adhesive) to an inner wall of the supply tube 1132. The supply tube 1132 and the capillary tube 1136 can be assembled before or after being introduced into the shaft 122. In some embodiments, the method can include directing the capillary tube 1136 to the first lateral opening 1164 and supporting the second portion 1136b of the capillary tube 1136 with the wall 1163 of the distal portion 1126 at the first lateral opening 1164. This can be useful, for example, to maintain the capillary tube 1136 at a desired position before forming the plug 1173.

The plug 1173 can be formed by introducing an adhesive material through the injection hole 1145. The amount of adhesive material injected and/or the position of the injection hole 1145 can be selected such that the adhesive material does not flow proximally far enough to interfere with the exhaust openings 1150a-c, the temperature sensor 1138, and/or the distal opening 1174 of the pressure-monitoring tube 1172. The vent 1165 can allow displaced air to escape as the adhesive material is introduced into the shaft 122. After the adhesive material is introduced, the solidity of the adhesive material can be increased, e.g., the adhesive material can be partially or fully cured. In some embodiments, increasing the solidity of the adhesive material can include exposing the adhesive material to ultraviolet light. As shown in FIG. 11A, the capillary tube 1136 can include an excess portion 1136c (shown in dashed lines) extending beyond the outer surface 1163a of the wall 1163. After increasing the solidity of the adhesive material, the excess portion 1136c of the capillary tube 1136 can be removed to form the distal end 1137. For example, the capillary tube 1136 can be cut at an angle less than about 80° (e.g., from about 25° to about 75°) relative to the length of the capillary tube 1136 proximate the excess portion 1136c. After removing the excess portion 1136c of the capillary tube 1136, the method can include attaching the balloon 142 to the distal portion 1126 such that the distal portion 1126 extends axially through the balloon 142 and the first lateral opening 1164 is within the balloon 142.

Figure 12A:
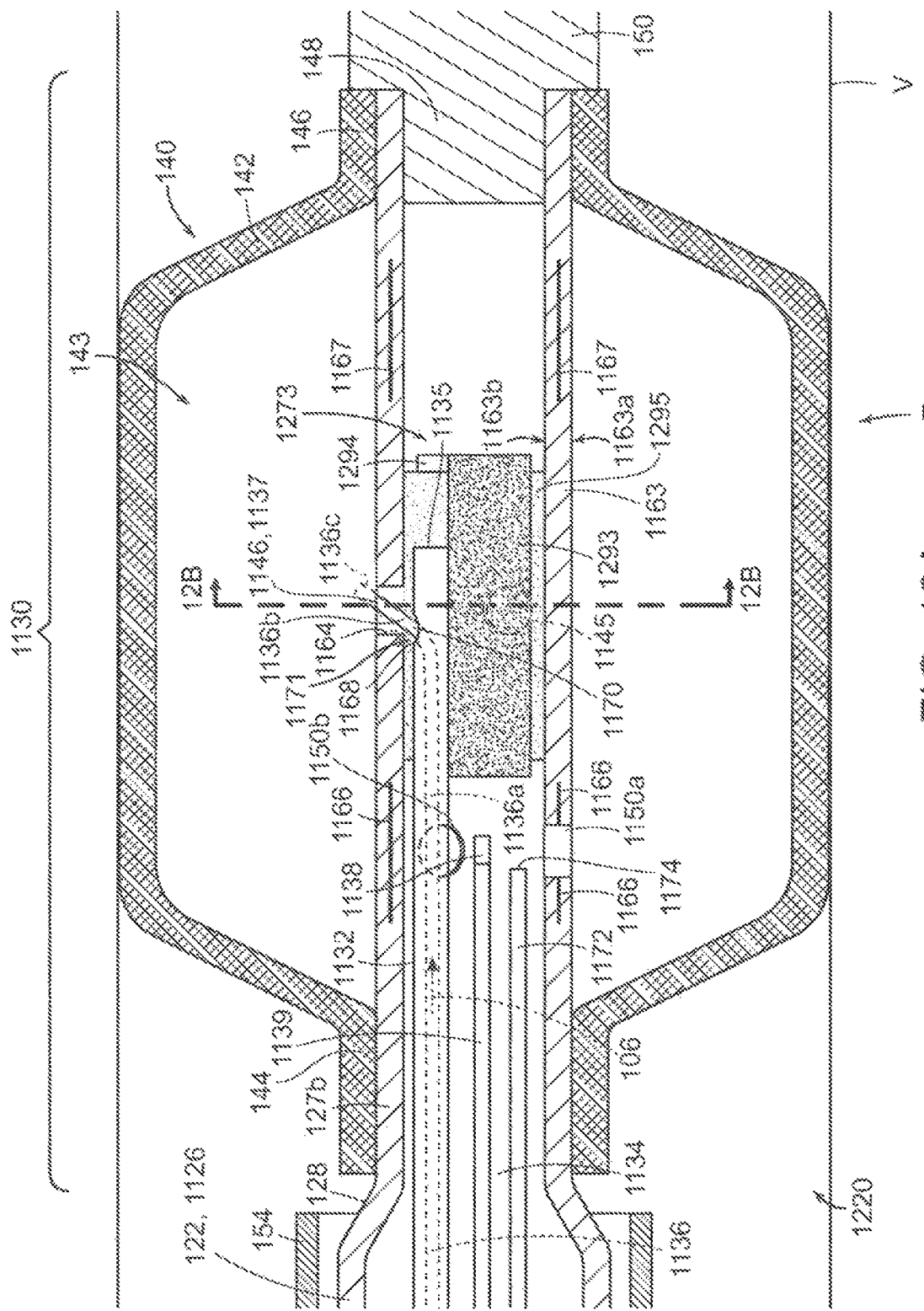
FIG. 12A is a side cross-sectional view of a cryotherapeutic device having a plug configured in accordance with another embodiment of the present technology.
Figure 12B:
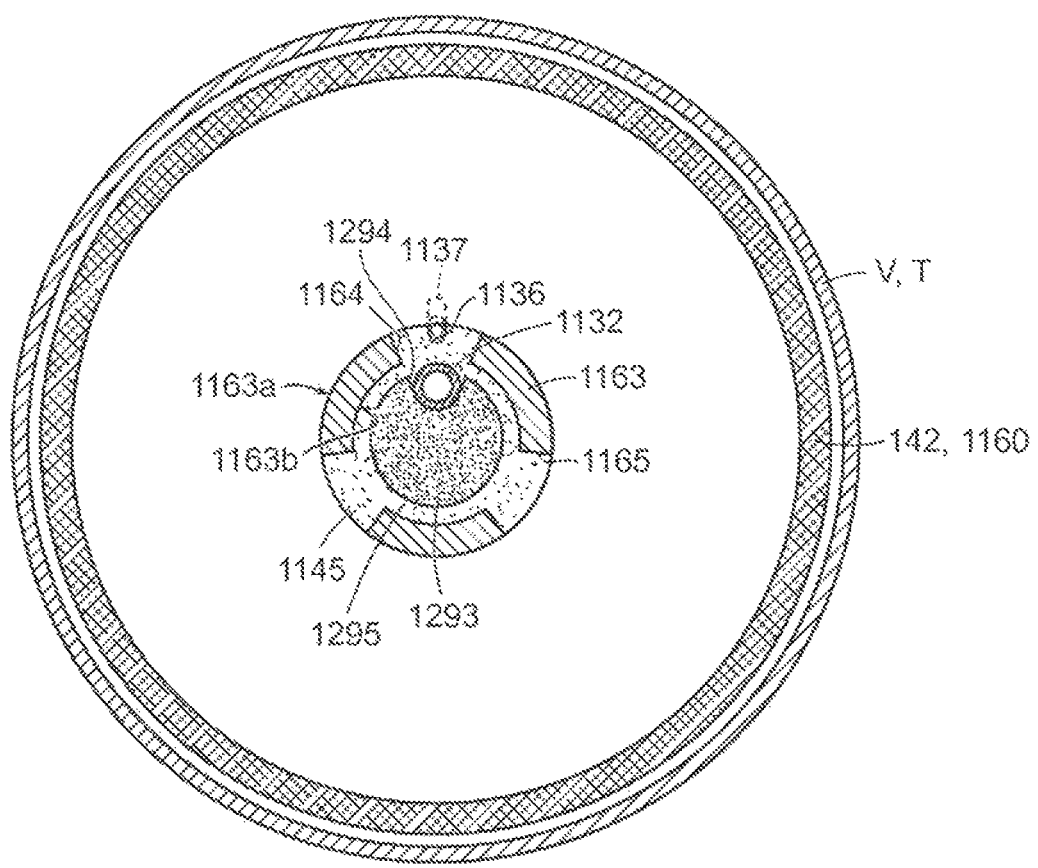
FIG. 12B is a cross-sectional view of the cryotherapeutic device shown in FIG. 12A taken along the line 12B-12B in FIG. 12A.

FIG. 12A is a side cross-sectional view of a cryotherapeutic device 1220 configured in accordance with another embodiment of the present technology. FIG. 12B is a cross-sectional view of the cryotherapeutic device 1220 taken along the line 12B-12B in FIG. 12A. With reference to FIGS. 12A and 12B together, the cryotherapeutic device 1220 can include a plug 1273 having a preformed portion 1293 with a generally cylindrical shape and a diameter less than the inner diameter of the distal portion 1126 of the shaft 122. In some embodiments, the preformed portion 1293 can be configured to be assembled with the supply tube 1132 outside the shaft 122. For example, the preformed portion 1293 can include a channel 1294 configured to at least partially receive the supply tube 1132. In some cases, the preformed portion 1293, the supply tube 1132, and the capillary tube 1136 can be assembled outside the shaft 122 and then pushed or pulled through the shaft 122 until the preformed portion 1293 is at or near the first lateral opening 1164 of the distal portion 1126. The preformed portion 1293 can also be positioned such that the channel 1294 faces the first lateral opening 1164 and the second lateral opening 1168 of the supply tube 1132 is generally aligned with the first lateral opening 1164. The capillary tube 1136 can be pushed or pulled through the second lateral opening 1168 toward (e.g., through) the first lateral opening 1164. In other embodiments, the capillary tube 1136 can be pushed or pulled through the terminal opening 1135 of the supply tube 1132 toward (e.g., through) the first lateral opening 1164.

The plug 1273 can further include adhesive material 1295 (e.g., cured or partially cured adhesive material) extending between the preformed portion 1293 and the inner surface 1163b of the wall 1163. During assembly, the adhesive material 1295 can be introduced (e.g., injected) through the injection hole 1145 and then at least partially cured (e.g., using ultraviolet light) to secure the preformed portion 1293 within the distal portion 1126. The adhesive material 1295 can extend partially or completely around the circumference of the preformed portion 1293. In some embodiments, capillary action can contribute to the distribution of the adhesive material 1295 around the preformed portion 1293. Accordingly, the uncured viscosity of the adhesive material 1295 can be selected, at least in part, to facilitate capillary distribution. The adhesive material 1295 can also extend into the channel 1294, into the terminal opening 1135 of the supply tube 1132, and/or into the first lateral opening 1164 of the distal portion 1126 around the capillary tube 1136. In addition to securing the plug 1273 within the distal portion 1126, the adhesive material 1295 can secure the supply tube 1132 to the preformed portion 1273, secure the supply tube 1132 to the distal portion 1126, support the capillary tube 1136 between the supply tube 1132 and the first lateral opening 1164, and/or support the capillary tube 1136 within the first lateral opening 1164.

Figure 12C:
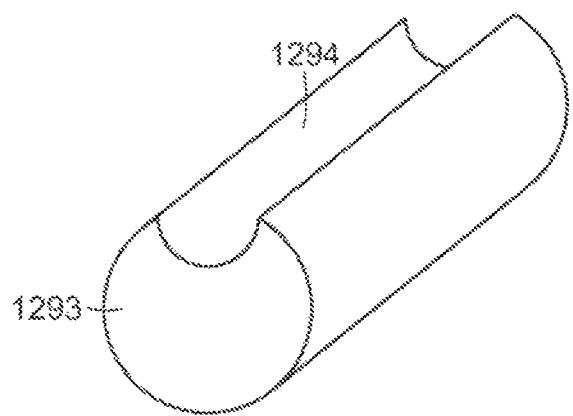
FIG. 12C is a perspective view of a preformed portion of the plug of the cryotherapeutic device shown in FIGS. 12A-12B.
Figure 12D:
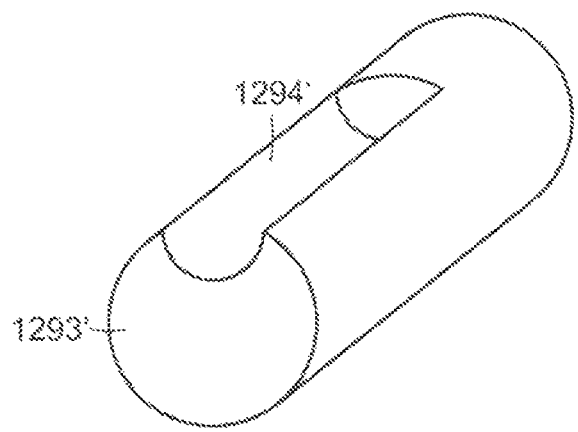
FIGS. 12D and 12E are perspective views of preformed portions of plugs configured in accordance with additional embodiments of the present technology.
Figure 12E:
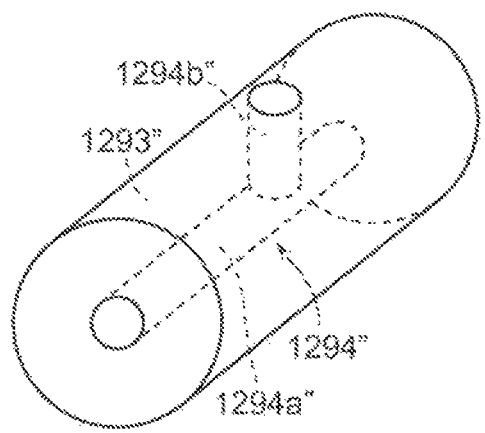

FIG. 12C is a perspective view of the preformed portion 1293 in isolation. As shown in FIG. 12C, the channel 1294 can extend from one end of the preformed portion 1293 to the opposite end along a path generally parallel to the length of the preformed portion 1293. In other embodiments, the preformed portion 1293 can have other suitable configurations. FIGS. 12D and 12E are perspective views of preformed portions 1293', 1293" of plugs configured in accordance with additional embodiments of the present technology. As shown in FIG. 12D, the preformed portion 1293' can include a channel 1294' extending only partially along the length of the preformed portion 1293'. This configuration, for example, can facilitate consistent positioning of the supply tube (not shown) relative to the preformed portion 1293', e.g., when the terminal opening of the supply tube abuts the distal end of the channel 1294'. As shown in FIG. 12E, the preformed portion 1293" can include a channel 1294" having a first portion 1294a" that extends internally through all or a portion of the length of the preformed portion 1293" and is configured to receive the supply tube (not shown), and a second portion 1294b" extending laterally from the first portion 1294a" and configured to receive the capillary tube (not shown). This configuration, for example, can facilitate central positioning of the supply tube within the distal portion of the shaft. A variety of other suitable configurations of preformed portions are also possible.

In some embodiments, the preformed portion 1293 can facilitate device manufacturing. For example, preformed portion 1293 can support and/or position the capillary tube 1136 to facilitate pulling the capillary tube 1136 toward (e.g., through) the first lateral opening 1164. Use of the preformed portion 1293 in this manner can reduce the likelihood that manipulating the capillary tube 1136 will cause the capillary tube 1136 to collapse. Furthermore, with reference to FIG. 11A, in some cases, it can be useful to position the pressure-monitoring tube 1172 prior to introducing adhesive material to form the plug 1173. This can make it difficult, however, to control the spacing between the distal opening 1174 of the pressure-monitoring tube 1172 and the plug 1173. In contrast, with reference again to FIGS. 12A-12B, the adhesive material 1295 can be generally contained within the space between the preformed portion 1293 and the inner surface 1163b of the wall 1163. Thus, introducing the adhesive material 1295 after positioning the pressure-monitoring tube 1172 can have little or no effect on the spacing between the distal opening 1174 of the pressure-monitoring tube 1172 and the plug 1273.

Additional Embodiments

Features of the cryotherapeutic-device components described above and illustrated in FIGS. 1-12E can be modified to form additional embodiments configured in accordance with the present technology. For example, the cryotherapeutic device 820 illustrated in FIGS. 8A-8B and other cryotherapeutic devices described above and illustrated in FIGS. 1-7B without guide members can include guide members that extend near or through distal portions of balloons. Similarly, the cryotherapeutic devices described above and illustrated in FIGS. 1-8B can include control members configured to receive control wires (e.g., pull wires). A control wire can be used, for example, to control (e.g., deflect, angle, position, or steer) a cooling assembly, an applicator, or another cryotherapeutic-device component from outside the vasculature.

Features of the cryotherapeutic-device components described above also can be interchanged to form additional embodiments of the present technology. For example, the open pitch coil 890 of the cooling assembly 830 illustrated in FIG. 8A can be incorporated into the cooling assembly 630 shown in FIG. 6 or into the cooling assembly 730 shown in FIGS. 7A-7B.

Related Anatomy and Physiology

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system, although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

1. The Sympathetic Chain

Figure 13:
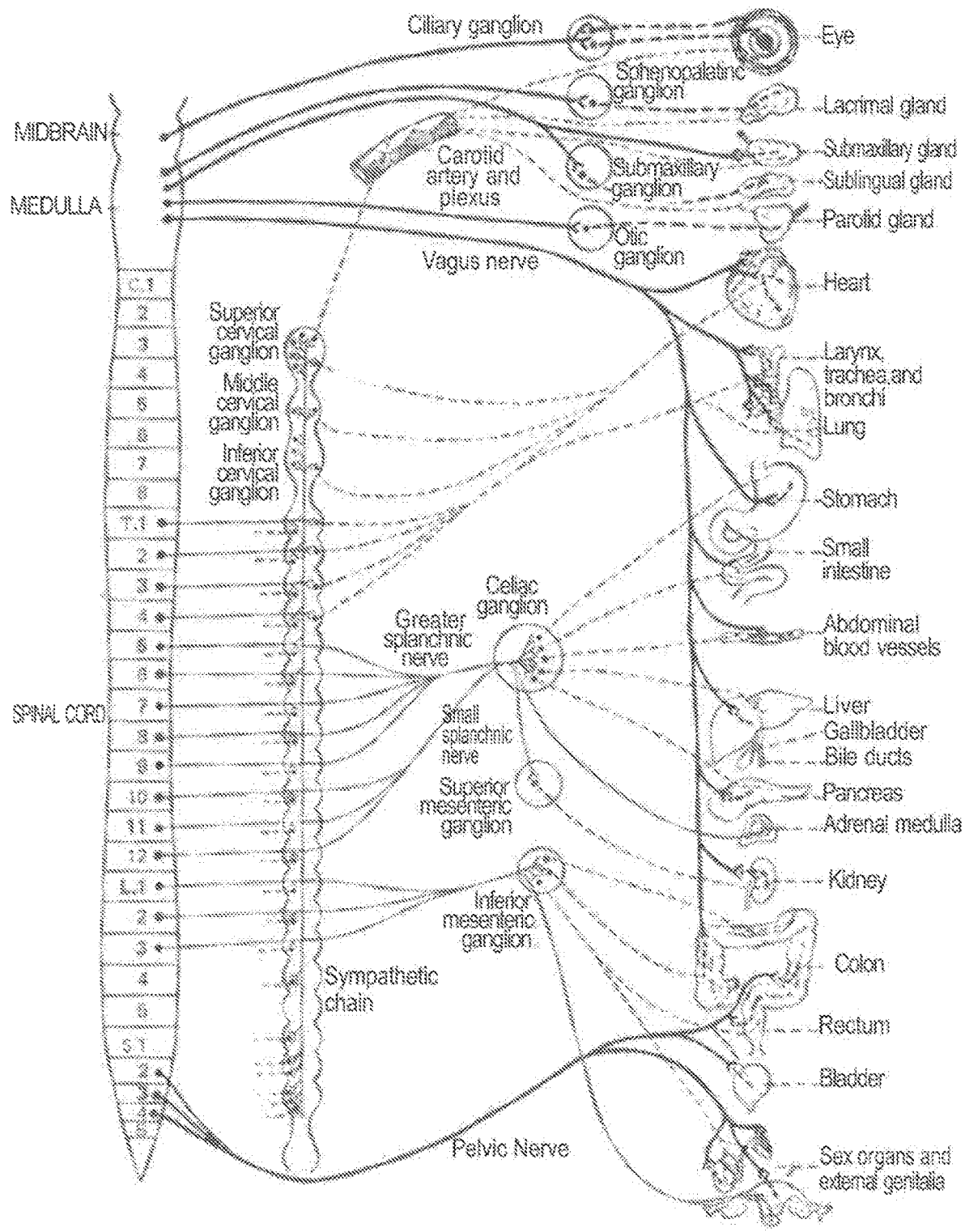
FIG. 13 is a conceptual illustration of the sympathetic nervous system (SNS) and how the brain communicates with the body via the SNS.

As shown in FIG. 13, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 14:
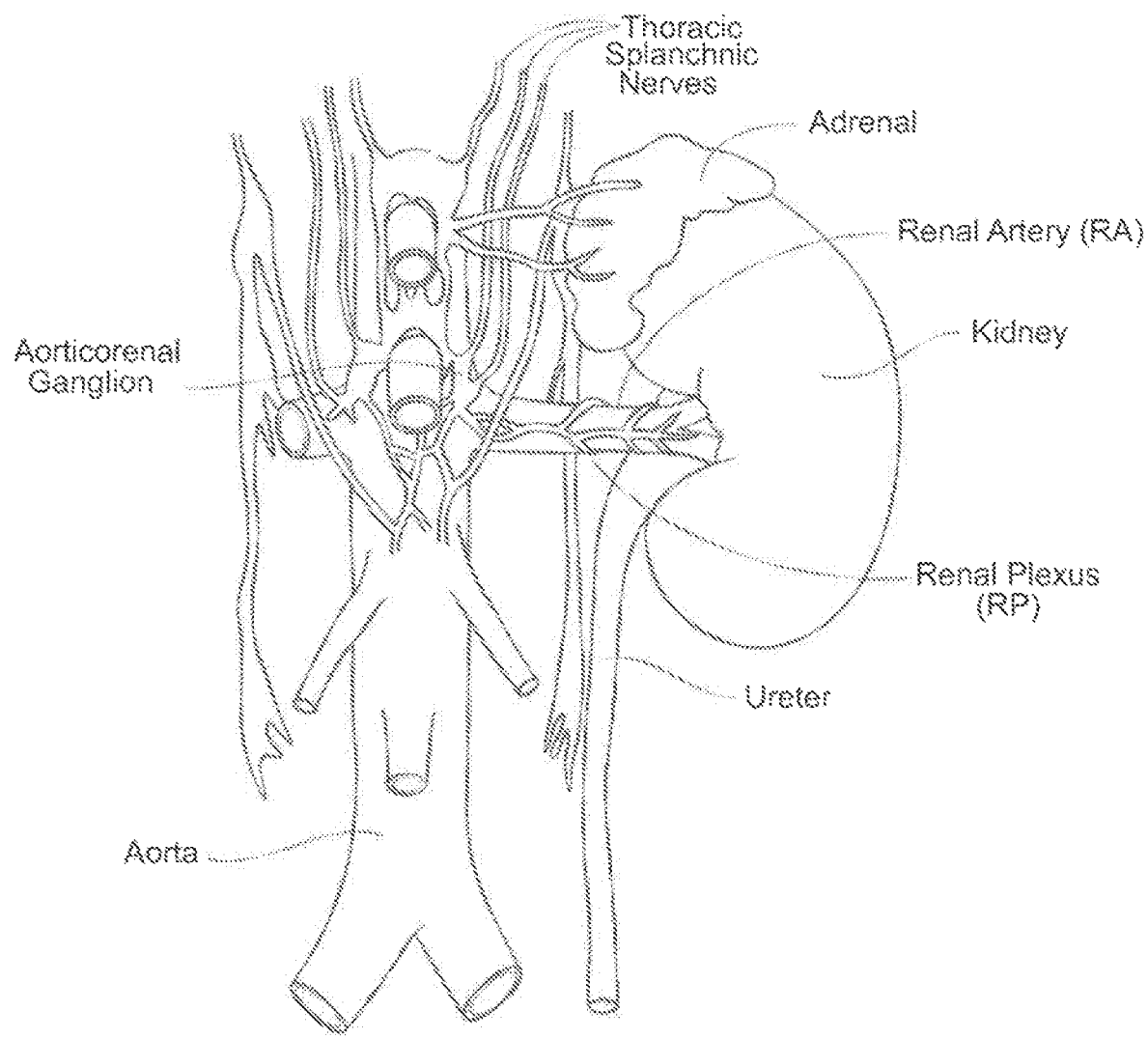
FIG. 14 is an enlarged anatomic view of nerves innervating a left kidney to form the renal plexus surrounding the left renal artery.

As FIG. 14 shows, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the SNS may accelerate heart rate; widen bronchial passages; decrease motility (movement) of the large intestine; constrict blood vessels; increase peristalsis in the esophagus; cause pupil dilation, cause piloerection (i.e., goose bumps), cause perspiration (i.e., sweating), and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing overactivity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine (NE) from the kidneys to plasma revealed increased renal NE spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced SNS overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group. This facilitates the occurrence of the well known adverse consequences of chronic sympathetic overactivity, such as hypertension, left ventricular hypertrophy, ventricular arrhythmias, sudden cardiac death, insulin resistance, diabetes, and metabolic syndrome.

(i) Renal Sympathetic Efferent Nerve Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 15A:
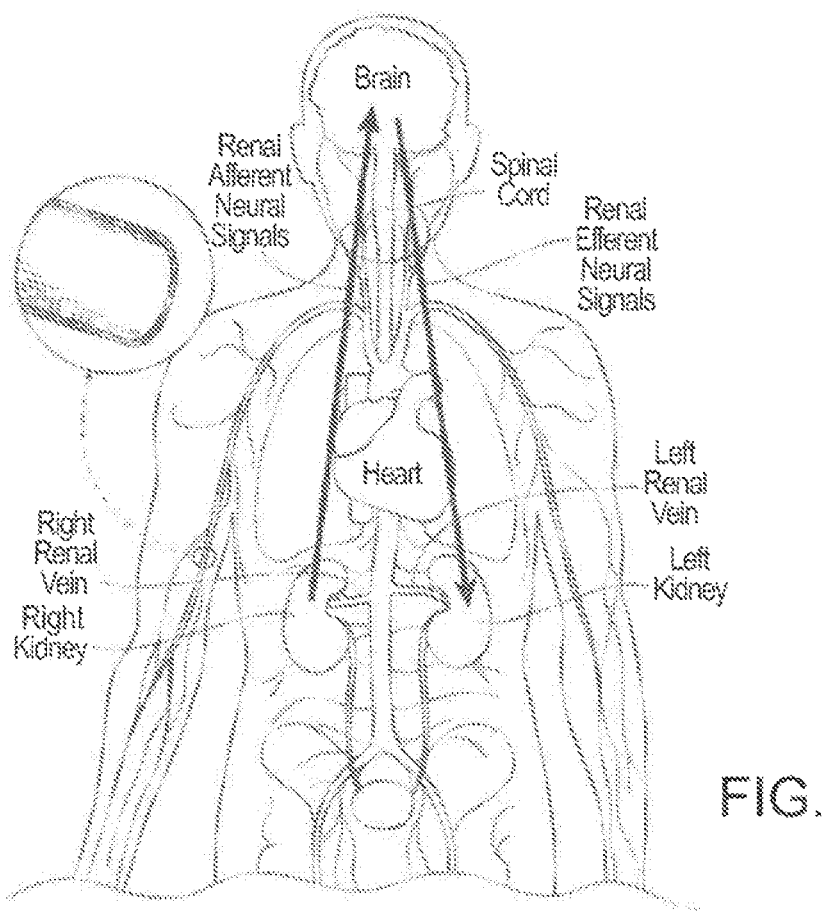
FIGS. 15A and 15B are anatomic and conceptual views, respectively, of a human body depicting neural efferent and afferent communication between the brain and kidneys.
Figure 15B:
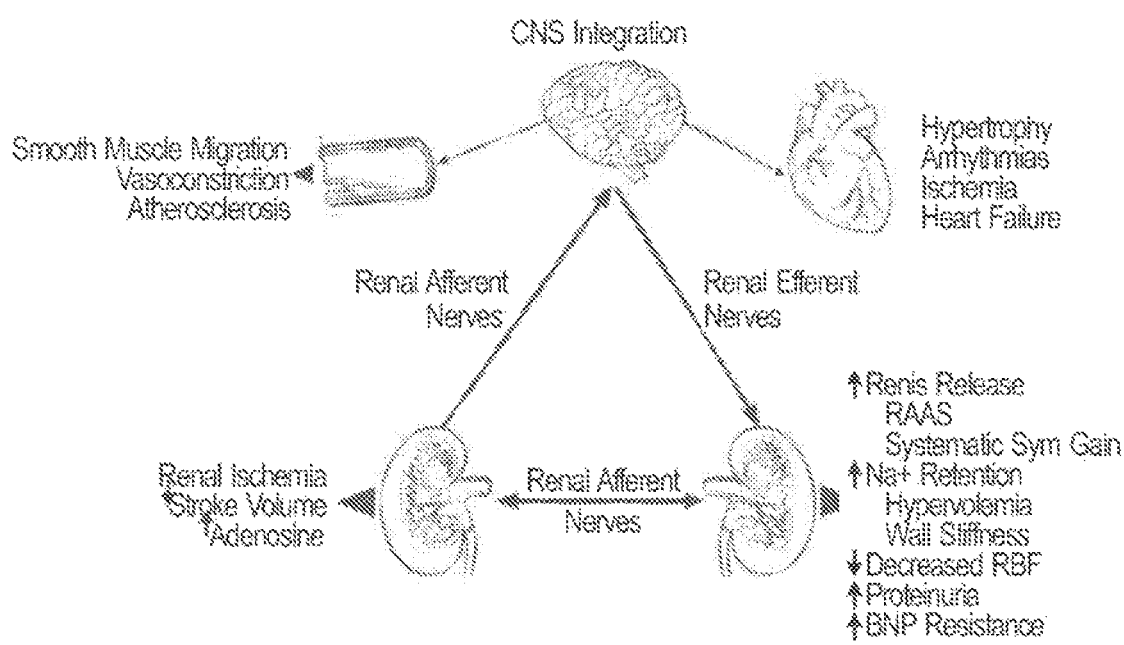

The kidneys communicate with integral structures in the CNS via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 15A and 15B, this afferent communication might be from the kidney to the brain or might be from one kidney to the other kidney (via the CNS). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 13. For example, as previously discussed, a reduction in central sympathetic drive may reduce the insulin resistance that afflicts people with metabolic syndrome and Type II diabetes. Additionally, patients with osteoporosis are also sympathetically activated and might also benefit from the down regulation of sympathetic drive that accompanies renal denervation.

C. Achieving Intravascular Access to the Renal Artery

Figures 16A, 16B:
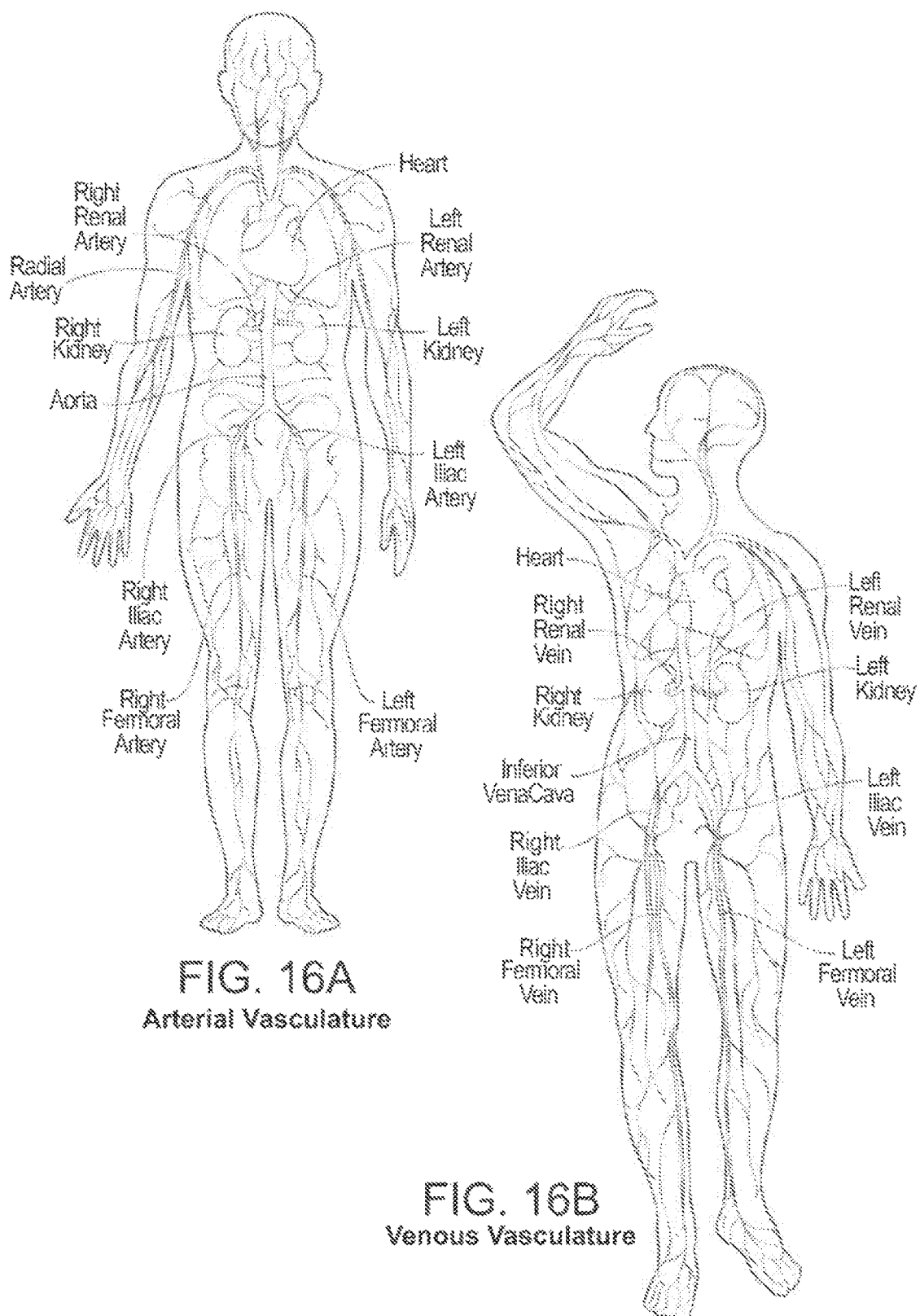
FIGS. 16A and 16B are anatomic views of the arterial vasculature and venous vasculature, respectively, of a human.

In accordance with the present technology, neuromodulation of a left and/or right renal plexus RP, which is intimately associated with a left and/or right renal artery, may be achieved through intravascular access. As FIG. 16A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 16B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with embodiments of the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access can account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes a cryotherapeutic device, consistent positioning, appropriate contact force applied by the cryotherapeutic device to the vessel wall, and adhesion between the cryo-applicator and the vessel wall can be important for predictability. However, navigation can be impeded by the tight space within a renal artery, as well as tortuosity of the artery. Furthermore, establishing consistent contact can be complicated by patient movement, respiration, and/or the cardiac cycle because these factors may cause significant movement of the renal artery relative to the aorta, and the cardiac cycle may transiently distend the renal artery (i.e. cause the wall of the artery to pulse).

After accessing a renal artery and facilitating stable contact between neuromodulatory apparatus and a luminal surface of the artery, nerves in and around the adventitia of the artery can be modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy can be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery can be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus can also be configured to allow for adjustable positioning and repositioning of an energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the cryotherapeutic devices and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery can also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the takeoff angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery can conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite intima-media thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment can be important to reach the target neural fibers, the treatment typically is not be too deep (e.g., the treatment can be less than about 5 mm from inner wall of the renal artery) so as to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as four inches cranially with respiratory excursion. This may impart significant motion to the renal artery connecting the aorta and the kidney. Accordingly, the neuromodulatory apparatus can have a unique balance of stiffness and flexibility to maintain contact between a cryo-applicator or another thermal treatment element and the vessel wall during cycles of respiration. Furthermore, the takeoff angle between the renal artery and the aorta may vary significantly between patients, and also may vary dynamically within a patient (e.g., due to kidney motion). The takeoff angle generally may be in a range of about 30°-135°.

The foregoing embodiments of cryotherapeutic devices are configured to accurately position the cryo-applicators in and/or near the renal artery and/or renal ostium via a femoral approach, transradial approach, or another suitable vascular approach. In any of the foregoing embodiments described above with reference to FIGS. 1-12E, single balloons can be configured to be inflated to diameters of about 3 mm to about 8 mm, and multiple balloons, if present, can collectively be configured to be inflated to diameters of about 3 mm to about 8 mm, and in several embodiments 4 mm to 8 mm. Additionally, in any of the embodiments shown and described herein with reference to FIGS. 1-12E, the balloons can individually and/or collectively have a length of about 3 mm to about 15 mm, and in several embodiments about 5 mm. For example, several specific embodiments of the devices shown in FIGS. 1-12E can have a 5 mm long balloon that is configured to be inflated to a diameter of 4 mm to 8 mm. The shaft of the devices described above with reference to any of the embodiments shown in FIGS. 1-12E can be sized to fit within a 6 Fr sheath, such as a 4 Fr shaft size.

EXAMPLES

1. A cryotherapeutic device, comprising:
an elongated shaft having a distal portion wherein the shaft is configured to locate the distal portion intravascularly at a treatment site in or otherwise proximate a renal artery or renal ostium;
a supply lumen housed within at least a portion of the shaft and configured to transport refrigerant along the shaft to the distal portion, the supply lumen having a terminal opening through which refrigerant can flow from the supply lumen into the distal portion;
a cooling assembly at the distal portion of the shaft, the cooling assembly having a delivery state and a deployed state, and the cooling assembly including—
an applicator having an expansion chamber wherein the distal portion extends axially through the expansion chamber; and
a distributor positioned at a distal end of the cooling assembly, wherein the distributor is in fluid communication with the terminal opening, and wherein the distributor includes a plurality of first orifices radially spaced apart from one another around the shaft and through which refrigerant can flow from the terminal opening into the expansion chamber;
an exhaust path extending from the expansion chamber along at least a portion of the shaft, the exhaust path including a plurality of second orifices proximate the first orifices and radially spaced apart from one another around the shaft and through which refrigerant can flow from the expansion chamber; and an internal barrier configured to seal the shaft at a position intermediate the terminal opening and the plurality of second orifices.

2. The cryotherapeutic device of example 1, wherein the plurality of first orifices are radially off-set from the plurality of second orifices.

3. The cryotherapeutic device of example 2, wherein the off-set is one of 90°, 60°, 45° and 30°.

4. The cryotherapeutic device of any of examples 1-3 further comprising a distal seal at a shaft terminus.

5. The cryotherapeutic device of any of examples 1-3 further comprising an atraumatic tip at a shaft terminus.

6. The cryotherapeutic device of any of examples 1-5 further comprising a shaft support at the distal portion.

7. The cryotherapeutic device of example 6, wherein the shaft support is positioned circumferentially around the shaft in a plane perpendicular to the shaft and circumjacent to at least one of the first orifices and second orifices.

8. The cryotherapeutic device of example 6 or example 7, wherein the shaft support includes radiopaque material and wherein at least one of the first and second orifices extends through the radiopaque material.

9. The cryotherapeutic device of example 6 or example 7, wherein the shaft support includes an open pitch coil support surrounding a portion of the distal portion, and wherein the portion includes at least one of the first and second orifices.

10. The cryotherapeutic device of example 9, wherein the first orifices have a first diameter and the second orifices have a second diameter, and wherein the open pitch coil support is a wire having a wire diameter less than the first and second diameters.

11. The cryotherapeutic device of any of examples 1-10 further comprising a pressure monitoring lumen extending along at least a portion of the shaft and having a distal opening in fluid communication with the expansion chamber, wherein the distal opening is cross-sectionally aligned with at least one of the second orifices.

12. The cryotherapeutic device of any of examples 1-11 further comprising a temperature monitoring sensor cross-sectionally aligned with at least one of the second orifices.

13. The cryotherapeutic device of example 12, wherein the temperature monitoring sensor is a thermocouple, and wherein the thermocouple has a distal portion cross-sectionally aligned with at least one of the second orifices and wherein a thermocouple lead extends along at least a portion of the shaft.

14. The cryotherapeutic device of any of examples 1-13 further comprising a capillary tube having a proximal tube end and distal tube end, the capillary tube positioned at the terminal opening of the supply lumen, wherein the capillary tube is configured to receive refrigerant through the proximal tube end from the terminal opening and release refrigerant through the distal tube end into the distal portion of the shaft.

15. The cryotherapeutic device of example 14, wherein terminal opening has a terminal diameter and wherein the distal tube end has a tube end diameter less than the terminal diameter.

16. The cryotherapeutic device of any of examples 1-15, wherein the distributor has an outer wall defined by a segment of the distal portion of the shaft within the applicator.

17. A cryotherapeutic device, comprising:
   an elongated shaft having a proximate portion and a distal portion, the distal portion having a first orifice and a second orifice proximate the first orifice, wherein the shaft is configured to locate the distal portion intravascularly at a treatment site;
   a supply lumen configured to transport refrigerant along the shaft to the distal portion, the supply lumen having a distal end and an inflow opening at the distal end, the inflow opening intermediate the first orifice and the second orifice;
   a cooling assembly at the distal portion of the shaft, the cooling assembly having a delivery state and a deployed state, and the cooling assembly including an applicator, wherein the distal portion extends axially through the applicator, and wherein the applicator is in fluid communication with the first orifice and the second orifice;
   an exhaust passage extending from the second orifice along at least a portion of the shaft, the exhaust passage configured to transport exhausted refrigerant away from the cooling assembly; and
   a partition located within the shaft between the first orifice and the second orifice and surrounding the supply lumen, the partition configured to seal the shaft between the first and second orifice.

18. The cryotherapeutic device of example 17, wherein the first orifice includes a plurality of first orifices radially spaced apart from one another around the shaft, and wherein the second orifice includes a plurality of second orifices radially spaced apart from one another around the shaft.

19. The cryotherapeutic device of example 18 wherein the plurality of first orifices are radially off-set from the plurality of second orifices. 20. The cryotherapeutic device of any of examples 17-19 wherein the partition includes a plug formed by injecting a barrier material around the supply lumen.

21. The cryotherapeutic device of any of examples 17-20 further comprising a pressure monitoring lumen extending along at least a portion of the shaft and having a distal opening in fluid communication with the applicator, wherein the distal opening is cross-sectionally aligned with the second orifice.

22. The cryotherapeutic device of any of examples 17-20 further comprising a temperature monitoring sensor cross-sectionally aligned with the second orifice.

23. The cryotherapeutic device of example 22, wherein the temperature monitoring sensor is a thermocouple, and wherein the thermocouple has a distal portion cross-sectionally aligned with the second orifice and wherein a thermocouple lead extends along at least a portion of the shaft.

24. The cryotherapeutic device of any of examples 17-23 further comprising a capillary tube, the capillary tube positioned at the distal end of the supply lumen, wherein the capillary tube is configured to receive refrigerant through a first end from the inflow opening and release refrigerant through a second inflow opening at a second end into the distal portion of the shaft.

25. The cryotherapeutic device of example 24, wherein supply lumen has a lumen diameter and wherein the second end has a second end diameter less than the lumen diameter.

26. The cryotherapeutic device of any of examples 17-25 further comprising a shaft support at the distal portion.

27. The cryotherapeutic device of any of examples 17-26 further comprising a distal seal at a shaft terminus.

28. The cryotherapeutic device of any of examples 17-26 further comprising an atraumatic tip at a shaft terminus. 29. The cryotherapeutic device of any of examples 17-28, wherein the applicator includes a balloon.

30. A cryotherapeutic device, comprising:
   an elongated shaft having a proximate portion and a distal portion, the distal portion having—
      a terminal opening;
      a distal seal at the terminal opening;
      a plurality of separate first holes spaced apart from each other and radially distributed around the shaft;
      a plurality of separate second holes spaced apart from each other and radially distributed around the shaft, wherein the plurality of second holes is proximate to the plurality of first holes along the distal portion; and
      an intermediate seal positioned along the shaft between the first and second holes;
   a supply tube configured to transport refrigerant along the shaft through the intermediate seal to the first holes;
   a cooling assembly at the distal portion of the shaft, the cooling assembly having a delivery state and a deployed state, and the cooling assembly including an applicator having an expandable member, wherein the distal portion extends axially through the expandable member, and wherein the expandable member is in fluid communication with the first and second holes; and
   an exhaust passage extending proximally from the intermediate seal along at least a portion of the shaft, the exhaust passage configured to transport exhausted refrigerant away from the cooling assembly; and
   wherein, in the deployed state, the applicator is configured to receive refrigerant through the first holes into the expandable member and exhaust refrigerant through the second holes into the exhaust passage.

31. The cryotherapeutic device of example 30, wherein at least one of the proximal portion and the distal portion is made of polyimide.

32. The cryotherapeutic device of example 30 or example 31, wherein at least one of the proximal portion and the distal portion is made of polyamide.

33. The cryotherapeutic device of any of examples 30-32, wherein the supply tube is stainless steel.

34. A cryotherapeutic device, comprising:
   an elongated shaft having a proximal portion and a distal portion wherein the shaft is configured to locate the distal portion intravascularly at a treatment site in or otherwise proximate a renal artery or renal ostium, and wherein the distal portion includes— a first zone having a first outer diameter and a first inner diameter; and a second zone distal to the first zone, the second zone having a second outer diameter and a second inner diameter; and wherein the first outer diameter is greater than the second outer diameter and the first inner diameter is greater than the second inner diameter; and wherein the second zone includes a plurality of proximal orifices and a plurality of distal orifices; and a cooling assembly at the second zone, the cooling assembly having a delivery state and a deployed state, the cooling assembly including— an applicator having a balloon wherein the second zone extends axially through the balloon;

an intermediate barrier in the second zone intermediate the proximal and distal orifices; and wherein, the applicator is configured to receive refrigerant through the distal orifices into the balloon and exhaust refrigerant through the proximal orifices.

35. A cryotherapeutic device, comprising:

an elongated shaft having a proximal portion and a distal portion wherein the shaft is configured to locate the distal portion intravascularly at a treatment site in or otherwise proximate a renal artery or renal ostium, and wherein the distal portion includes— a first zone having a first outer diameter and a first inner diameter; and a second zone distal to the first zone, the second zone having a second outer diameter and a second inner diameter; and wherein the first outer diameter is greater than the second outer diameter and the first inner diameter is greater than the second inner diameter; and a cooling assembly at the second zone, the cooling assembly having a delivery state and a deployed state, the cooling assembly including— an applicator having an expandable member; and a plurality of orifices through which refrigerant can flow, the orifices being arranged with respect to the applicator to direct flows of refrigerant to provide cryogenic cooling to the treatment site and exhaust refrigerant from the cooling assembly.

36. The cryotherapeutic device of example 35, wherein the second zone includes a plurality of proximal orifices and a plurality of distal orifices, and wherein the second zone extends axially through the expandable member.

37. The cryotherapeutic device of example 36 further comprising an intermediate barrier in the second zone between the proximal and distal orifices, and wherein the applicator is configured to receive refrigerant through the distal orifices into the expandable member and exhaust refrigerant through the proximal orifices.

38. The cryotherapeutic device of any of examples 35-37, wherein the plurality of orifices includes an inflow orifice, and wherein the cryotherapeutic device further comprises a supply lumen configured transport refrigerant along the shaft to the distal portion, the supply lumen having a distal end connected to the inflow orifice providing a refrigerant path from the supply lumen to the expandable member.

39. The cryotherapeutic device of any of examples 35-38 further comprising:

a flexible tip at a terminal end of the cryotherapeutic device; and a tip support extending through the expandable member from the distal portion to the flexible tip.

40. A cryotherapeutic device, comprising:

an elongated shaft having a distal portion, the distal portion having a terminal end, an inflow orifice, and an exhaust orifice, wherein the inflow and exhaust orifices are proximate to the terminal end, and wherein the shaft is configured to locate the distal portion intravascularly at a treatment site;

a cooling assembly at the distal portion of the shaft, the cooling assembly including an applicator having an expansion chamber, wherein the distal portion extends axially through the expansion chamber, and wherein the expansion chamber is in fluid communication with the inflow and exhaust orifices;

a supply lumen configured to transport refrigerant along the shaft to the distal portion, the supply lumen having a distal end connected to the inflow orifice providing a refrigerant path from the supply lumen to the expansion chamber; and an exhaust passage extending from the exhaust orifice along at least a portion of the shaft, the exhaust passage configured to transport exhausted refrigerant away from the cooling assembly.

41. The cryotherapeutic device of example 40 further comprising a pressure monitoring lumen extending along at least a portion of the shaft to the distal portion and having a distal opening in fluid communication with the expansion chamber, wherein the distal opening is proximal to the exhaust orifice.

42. The cryotherapeutic device of example 40 further comprising a temperature monitoring sensor in communication with the expansion chamber.

43. The cryotherapeutic device of example 42, wherein the temperature monitoring sensor is a thermocouple having a thermocouple lead extending along at least a portion of the shaft, and wherein the thermocouple extends through a shaft wall into the expansion chamber.

44. The cryotherapeutic device of example 42, wherein the temperature monitoring sensor is a thermocouple, and wherein the thermocouple has a distal portion cross-sectionally aligned with the exhaust orifice and wherein a thermocouple lead extends along at least a portion of the shaft.

45. The cryotherapeutic device of any of examples 40-44, wherein the exhaust orifice includes a plurality of separate exhaust orifices spaced apart from each other and radially distributed around the shaft.

46. The cryotherapeutic device of any of examples 40-45, wherein the distal portion includes a first exhaust orifice and a second exhaust orifice, the first exhaust orifice radially spaced 180° apart from the second exhaust orifice around the shaft.

47. The cryotherapeutic device of any of examples 40-46 further comprising an atraumatic tip at the terminal end.

48. A cryotherapeutic device, comprising:

an elongated shaft having a distal portion, wherein the shaft is configured to locate the distal portion intravascularly at a treatment site;

a flexible atraumatic tip;

a cooling assembly at the distal portion of the shaft, the cooling assembly including an applicator having an expandable member, wherein the expandable member is connected to the distal portion of the shaft at a proximal end and connected to the atraumatic tip at the proximal end;

a tip support extending through the expandable member from the distal portion to the atraumatic tip; and a supply lumen configured to transport refrigerant along the shaft to the distal portion, the supply lumen having a distal end and in inflow opening at the distal end, wherein the inflow opening is in fluid communication with the expandable member.

49. The cryotherapeutic device of example 48, wherein the tip support can include a plurality of tip supports extending through the expandable member from the distal portion to the atraumatic tip.

50. The cryotherapeutic device of example 48, wherein the tip support includes a distal portion of the shaft extending through the expandable member, and wherein the distal portion includes apertures formed longitudinally along the shaft to provide openings through which refrigerant can flow to the expandable member.

51. The cryotherapeutic device of example 50 further comprising a shaft support at the distal portion, wherein the shaft support includes an open pitch coil surrounding at least a portion of the tip support.

52. The cryotherapeutic device of any of examples 48-51, wherein the tip support includes a guide wire lumen extending along at least a portion of the shaft and through the expandable member to the atraumatic tip.

53. The cryotherapeutic device of example 52 further comprising an open pitch coil support surrounding at least a portion of the guide wire lumen within the expandable member.

54. The cryotherapeutic device of any of examples 48-53 further comprising a pressure monitoring lumen extending along at least a portion of the shaft to the distal portion and having a distal opening in fluid communication with the expandable member.

55. The cryotherapeutic device of any of examples 48-54 further comprising a temperature monitoring sensor in communication with the expandable member.

56. The cryotherapeutic device of example 55, wherein the temperature monitoring sensor is a thermocouple having a thermocouple lead extending along at least a portion of the shaft, and wherein the thermocouple is in fluid communication with the expandable member.

57. The cryotherapeutic device of any of examples 48-56 further comprising a capillary tube having a proximal tube end and distal tube end, the capillary tube positioned at the distal end of the supply lumen, wherein the capillary tube is configured to receive refrigerant through the proximal tube end from the inflow opening and release refrigerant through the distal tube end into the expandable member.

58. The cryotherapeutic device of any of examples 48-57, wherein the supply lumen partially extends into the expandable member.

59. The cryotherapeutic device of any of examples 48-58 further comprising an exhaust passage extending from the expandable member along at least a portion of the shaft and configured to exhaust refrigerant away from the treatment site.

60. A cryotherapeutic device, comprising:
an elongated shaft configured to locate a distal cooling assembly intravascularly at a treatment site in or otherwise proximate a renal artery or renal ostium, the shaft having—
a proximal portion, the proximal portion including a passage having an opening at a distal terminal end; and
an independent distal portion connected to the distal terminal end at a junction;
wherein the junction is transverse to the opening;
wherein the opening is not accessible at the junction;
wherein the passage is configured to receive a guide wire lumen extending through the distal portion; and
a guide wire lumen positioned in the passage and extending through the distal portion of the shaft, wherein the guide wire lumen is accessible from outside of the shaft; and
wherein the cooling assembly is connected to the shaft distal to the junction.

61. The cryotherapeutic device of example 60, wherein at least one of the proximal portion and the distal portion are made of polyimide.

62. The cryotherapeutic device of example 60 or example 61, wherein at least one of the proximal portion and the distal portion are made of polyamide.

63. The cryotherapeutic device of any of examples 60-62, wherein the proximal portion has a neck region adjacent to the terminal end, the neck region having an outer diameter less than an inner of the distal portion, and wherein the distal portion is configured to receive the neck region at the junction.

64. The cryotherapeutic device of any of examples 60-63 further comprising an intermediate portion at the junction.

65. The cryotherapeutic device of example 64, wherein the intermediate portion and the independent distal portion provide one or more seals at the junction.

66. A cryotherapeutic device, comprising:
an elongated shaft having a distal portion with a wall and a lateral opening extending through the wall;
a supply tube housed within at least a portion of the shaft and configured to transport refrigerant along the shaft to the distal portion;
a cooling assembly at the distal portion, the cooling assembly having a delivery state and a deployed state, the cooling assembly including—
an applicator having an expansion chamber, the distal portion extending axially through the expansion chamber, and
an orifice through which refrigerant can flow into the expansion chamber;
an exhaust path extending from the expansion chamber along at least a portion of the shaft, the exhaust path including an exhaust opening through which refrigerant can flow from the expansion chamber, the exhaust opening extending through the wall of the distal portion;
a capillary tube including a first portion within the supply tube and a second portion extending from the supply tube to the lateral opening, the capillary tube defining the orifice; and
a plug within the distal portion distal to the exhaust opening, the plug extending around the second portion of the capillary tube.

67. The cryotherapeutic device of example 66 wherein the shaft is configured to locate the distal portion intravascularly at a treatment site in or otherwise proximate a renal artery or renal ostium.

68. The cryotherapeutic device of example 66 or example 67 wherein generally all of the capillary tube is within a combination of the supply tube and the plug.

69. The cryotherapeutic device of any of examples 66-68 wherein the plug extends into the lateral opening around the second portion of the capillary tube.

70. The cryotherapeutic device of any of examples 66-69 wherein the second portion of the capillary tube extends from the supply tube to the lateral opening at an angle relative to the supply tube from about 25° to about 75°.

71. The cryotherapeutic device of any of examples 66-70 wherein:
- the wall of the distal portion has an outer surface toward the expansion chamber and an inner surface opposite the outer surface; and
- the capillary tube has a distal end that defines the orifice and is generally flush with the outer surface of the wall of the distal portion.

72. The cryotherapeutic device of example 71 wherein the distal end of the capillary tube is not perpendicular to a length of the second portion of the capillary tube.

73. The cryotherapeutic device of any of examples 66-72 wherein;
- the lateral opening is a first lateral opening;
- the supply tube includes a second lateral opening; and
- the capillary tube further includes a transition region between the first and second portions of the capillary tube proximate the second lateral opening.

74. The cryotherapeutic device of example 73 wherein the capillary tube includes a rounded elbow proximate the transition region.

75. The cryotherapeutic device of example 74 wherein the rounded elbow defines an angle between the first and second portions of the capillary tube from about 25° to about 75°.

76. The cryotherapeutic device of any of examples 66-75 wherein the plug includes an adhesive material.

77. The cryotherapeutic device of example 76 wherein the distal portion further includes an injection hole through the wall of the distal portion proximate the plug.

78. The cryotherapeutic device of example 77 wherein the distal portion further includes a vent through the wall of the distal portion proximate the plug.

79. The cryotherapeutic device of example 78 wherein the lateral opening, the injection hole, and the vent are circumferentially spaced apart from each other in a plane perpendicular to a length of the distal portion.

80. The cryotherapeutic device of example 79 wherein:
- the plane is a first plane;
- the exhaust opening is a first exhaust opening;
- the exhaust path further includes a second exhaust opening and a third exhaust opening through which refrigerant can flow from the expansion chamber;
- the first, second, and third exhaust openings are circumferentially spaced apart from each other in a second plane perpendicular to the length of the distal portion; and
- circumferential positions of the lateral opening, the injection hole, and the vent in the first plane are offset relative to circumferential positions of the first, second, and third exhaust openings in the second plane.

81. The cryotherapeutic device of any of examples 66-80 wherein:
- the distal portion includes a reinforcing member; and
- the exhaust opening extends through the reinforcing member.

82. The cryotherapeutic device of example 81 wherein the reinforcing member is embedded in the wall of the distal portion.

83. The cryotherapeutic device of example 82 wherein the reinforcing member is radiopaque.

84. The cryotherapeutic device of example 83 wherein:
- the reinforcing member is a first reinforcing member;
- the distal portion further includes a second reinforcing member embedded in the wall of the distal portion;
- the second reinforcing member is radiopaque; and
- the first and second reinforcing members are, respectively, proximally and distally spaced apart from the lateral opening generally equal distances.

85. The cryotherapeutic device of example 84 wherein the lateral opening is generally centered along a length the distal portion within the expansion chamber.

86. A method for making a cryotherapeutic device, comprising:
- directing a capillary tube to a lateral opening through a wall of a distal portion of a shaft;
- introducing an adhesive material through an injection hole of the distal portion such that the adhesive material extends around the capillary tube proximate the lateral opening;
- increasing a solidity of the adhesive material;
- removing an excess portion of the capillary tube after increasing the solidity of the adhesive material, the excess portion projecting beyond an outer surface of the wall; and
- attaching a balloon to the distal portion such that the distal portion extends axially through the balloon and the lateral opening is within the balloon.

87. The method of example 86, wherein removing the excess portion of the capillary tube includes cutting the capillary tube at an angle from about 25° to about 75° relative to a length of the capillary tube proximate the excess portion.

88. The method of example 86 or example 87, wherein the lateral opening is a first lateral opening, and the method further comprises:
- positioning the capillary tube such that a first portion of the capillary tube is within a supply tube and a second portion of the capillary tube extends from a second lateral opening of the supply tube; and
- sealing the supply tube around the first portion of the capillary tube.

89. The method of example 88, further comprising supporting the second portion of the capillary tube with the wall of the distal portion at the first lateral opening before introducing the adhesive material.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A cryotherapeutic device, comprising:
    a shaft having a distal end portion configured to be advanced intravascularly toward a treatment site within a renal artery of a human patient, wherein the distal end portion of the shaft has a wall defining a lumen;
    a balloon extending circumferentially around the distal end portion of the shaft, wherein the balloon is transformable between a low-profile delivery state and an expanded deployed state;
    a supply tube carried by the shaft, wherein the supply tube is configured to carry refrigerant flowing distally toward the balloon, and wherein the supply tube includes a lateral opening within the lumen;
    a supply opening extending laterally through the wall of the shaft within the balloon;
    an exhaust opening extending laterally through the wall of the shaft within the balloon, wherein the exhaust opening is proximal to the supply opening;
    a capillary tube including a first portion within the supply tube and a second portion extending from an interior of the supply tube toward the supply opening via the lateral opening of the supply tube; and
    a plug within the lumen, wherein the plug extends around the second portion of the capillary tube within the lumen.

2. The cryotherapeutic device of claim 1 wherein the capillary tube is entirely within a combination of the supply tube and the plug.

3. The cryotherapeutic device of claim 1 wherein the plug extends into the supply opening around the second portion of the capillary tube.

4. The cryotherapeutic device of claim 1 wherein the second portion of the capillary tube extends from the interior of the supply tube toward the supply opening at an angle relative to the supply tube from 25° to 75°.

5. The cryotherapeutic device of claim 1 wherein:
    the wall of the distal end portion of the shaft has an outer surface spaced apart from the lumen and an inner surface opposite the outer surface; and
    the capillary tube has a distal end defining an orifice flush with the outer surface of the wall of the distal end portion of the shaft.

6. The cryotherapeutic device of claim 5 wherein the distal end of the capillary tube is not perpendicular to a length of the second portion of the capillary tube.

7. The cryotherapeutic device of claim 1 wherein the capillary tube includes a rounded elbow between the first and second portions of the capillary tube.

8. The cryotherapeutic device of claim 7 wherein the rounded elbow defines an angle from 25° to 75°.

9. The cryotherapeutic device of claim 1 wherein the plug includes an adhesive material.

10. The cryotherapeutic device of claim 9, further comprising an injection opening extending laterally through the wall of the shaft, wherein the plug extends into the injection opening.

11. The cryotherapeutic device of claim 10 wherein the supply opening and the injection opening are circumferentially spaced apart from one another in a plane perpendicular to a length of the distal end portion of the shaft.

12. The cryotherapeutic device of claim 11 wherein:
    the plane is a first plane;
    the exhaust opening is a first exhaust opening;
    the cryotherapeutic device further comprises a second exhaust opening extending laterally through the wall of the shaft within the balloon;
    the first and second exhaust openings are circumferentially spaced apart from one another in a second plane perpendicular to the length of the distal end portion of the shaft; and
    respective circumferential positions of the supply opening and the injection opening in the first plane are circumferentially offset relative to respective circumferential positions of the first and second exhaust openings in the second plane.

13. The cryotherapeutic device of claim 1 wherein:
    the distal end portion of the shaft includes a reinforcing member; and
    the exhaust opening extends through the reinforcing member.

14. The cryotherapeutic device of claim 13 wherein the reinforcing member is embedded in the wall of the distal end portion of the shaft.

15. The cryotherapeutic device of claim 14 wherein the reinforcing member is radiopaque.

16. The cryotherapeutic device of claim 1 wherein the supply opening is centered along a length the distal end portion of the shaft within the balloon.

* * * * *